(12) United States Patent
Mineau

(10) Patent No.: US 10,723,772 B2
(45) Date of Patent: *Jul. 28, 2020

(54) FOLLISTATIN IN TREATING DUCHENNE MUSCULAR DYSTROPHY

(71) Applicant: Shire Human Genetic Therapies, Inc., Lexington, MA (US)

(72) Inventor: Rochelle Mineau, Lexington, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/951,929

(22) Filed: Apr. 12, 2018

(65) Prior Publication Data

US 2018/0305421 A1 Oct. 25, 2018

Related U.S. Application Data

(63) Continuation of application No. 14/762,373, filed as application No. PCT/US2014/012996 on Jan. 24, 2014, now Pat. No. 9,957,309.

(60) Provisional application No. 61/915,733, filed on Dec. 13, 2013, provisional application No. 61/756,996, filed on Jan. 25, 2013.

(51) Int. Cl.
| | | |
|---|---|---|
| *A61P 21/06* | (2006.01) | |
| *A61K 38/17* | (2006.01) | |
| *C07K 14/47* | (2006.01) | |
| *C07K 19/00* | (2006.01) | |
| *C07H 21/04* | (2006.01) | |
| *C12N 15/63* | (2006.01) | |
| *A61K 38/00* | (2006.01) | |

(52) U.S. Cl.
CPC .......... *C07K 14/47* (2013.01); *A61K 38/1709* (2013.01); *C07H 21/04* (2013.01); *C07K 14/4703* (2013.01); *C07K 14/4708* (2013.01); *C07K 19/00* (2013.01); *C12N 15/63* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 6,277,375 B1 | 8/2001 | Ward |
| 7,572,763 B2 | 8/2009 | Hill et al. |
| 8,012,476 B2 | 9/2011 | Dall'Acqua et al. |
| 8,163,881 B2 | 4/2012 | Ober |
| 2012/0232021 A1 | 9/2012 | Martini et al. |
| 2015/0158923 A1 | 6/2015 | Sherman et al. |
| 2015/0337032 A1 | 11/2015 | Mader et al. |

FOREIGN PATENT DOCUMENTS

| | | |
|---|---|---|
| EP | 1748069 A1 | 1/2007 |
| WO | WO-2005/033134 A2 | 4/2005 |
| WO | WO-2008/030367 A2 | 3/2008 |
| WO | WO-2009/158015 A2 | 12/2009 |
| WO | WO-2009/158025 A2 | 12/2009 |
| WO | WO-2011/031901 A1 | 3/2011 |
| WO | WO 2014/043344 A1 | 3/2014 |
| WO | WO-2014/187807 A1 | 11/2014 |
| WO | WO 2015/187977 A1 | 12/2015 |
| WO | WO 2016/057975 A2 | 4/2016 |

OTHER PUBLICATIONS

Altschul, S. et al., Basic Local Alignment Search Tool, J. Mol. Biol., 215(3):403-410 (1990).
Altschul, S. et al., Gapped BLAST and PSI-BLAST: a new generation of protein database search programs, Nucleic Acids Res., 25(17):3389-3402 (1997).
Altschul, S. et al., Local alignment statistics, 266:460-80, Methods in Enzymology., 1996.
Baxevanis, A. et al., Bioinformatics: A Practical Guide to the Analysis of Genes and Proteins, Wiley (1998).
Bork, P., "Powers and pitfalls in sequence analysis: the 70% hurdle", Genome Research,10: 398-400 (2000).
Brenner, SE, "Errors in genome annotation", Trends in Genetics, 15(4): 132-3 (1999).
Datta-Mannan, A. et al., An Engineered Human Follistatin Variant: Insights into the Pharmacokinetic and Pharmocodynamic Relationships of a Novel Molecule with Broad Therapeutic Potential, The Journal of Pharmacology and Experimental Therapeutics, 344:616-623 (2013).
Datta-Mannan, A., et al., Insights into the Impact of Heterogeneous Glycosylation on the Pharmacokinetic Behavior of Follistatin-Fc-Based Biotherapeutics, Drug Metab Dispos, 43(12):1882-1890 (2015).
Dennler, S. et al., Direct binding of Smad3 and Smad4 to critical TGF beta-inducible elements in the promoter of human plasminogen activator inhibitor-type 1 gene, EMBO J, 17(11):3091-3100 (1998).
Doerks et al., "Protein annotation: detective work for function prediction", Trends in Genetics, 14(6): 248-50 (1998).
Haidet, et al., Long-term Enhancement of Skeletal Muscle Mass and Strength by Single Gene Administration of Myostatin Inhibitors, PNAS, vol. 105, No. 11, Mar. 18, 2008, pp. 4318-4322.
Gilson, H. et al., Follistatin Induces Muscle Hypertropohy Through Satellite Cell Proliferation and Inhibition of Both Myostatin and Activin, Journal of Physiology Endrocrinology, 297(1):E157-E164 (2009).
Graham et al., Characteristics of a human cell line transformed by DNA from human adenovirus type 5, J. Gen Virol., 36(1): 59-74, 1977.

(Continued)

*Primary Examiner* — Zachary C Howard
(74) *Attorney, Agent, or Firm* — Proskauer Rose LLP; Fangli Chen

(57) ABSTRACT

The present invention provides, among other things, methods and compositions for treating muscular dystrophy, in particular, Duchenne muscular dystrophy (DMD). In some embodiments, a method according to the present invention includes administering to an individual who is suffering from or susceptible to DMD an effective amount of a recombinant follistatin protein such that at least one symptom or feature of DMD is reduced in intensity, severity, or frequency, or has delayed onset.

10 Claims, 25 Drawing Sheets

Specification includes a Sequence Listing.

(56) References Cited

OTHER PUBLICATIONS

International Search Report for PCT/US2014/012996, 5 pages (dated Jun. 2, 2015).

Keutmann, H. et al., The Role of Follistatin Domains in Follistatin Biological Action, Molecular & Endocrinology, 18(1):228-240 (2004).

Korchynskyi, O. and Ten Dijke, P., Identification and functional characterization of distinct critically important bone morphogenetic protein-specific response elements in the Id1 promoter, J Biol Chem, 277(7):4883-4891 (2002).

Lee, S. et al., Regulation of Muscle Mass by Follistatin and Activins, Molecular Endocrinology, 24(10):1998-2008 (2010).

Mather et al., Culture of Testicular Cells in Hormone-Supplemented Serum-Free Medium, Annals New York Acad. Sci., 383:44-68 (1982).

Mather, Establishment and characterization of two distinct mouse testicular epithelial cell lines, Biol. Reprod., 23: 243-251, 1980.

Misener, S. and Krawetz, S., Bioinformatics Methods and Protocols, Methods in Molecular Biology, 132, Humana Press (1999).

Ngo et al (1994) "The Protein Folding Problem and Tertiary Structure Prediction, Chapter 14: Computational Complexity Protein Structure Prediction, and the Levinthal Paradox" pp. 433-440 and 492-495 only.

pcDNA3 (Invitrogen) <URL:http://www2.kumc.edu/soalab/LabLinks/vectors/pcdna3_mcs.pdf>.

Sidis, Y. et al., Heparin and Activin-Binding Determinants in Follistatin and FSTL3, Endocrinology, 146(1):130-136 (2005).

Skolnick et al. "From genes to protein structure and function: novel applications of computational approaches in the genomic era", Trends in Biotech., 18(1): 34 (2000).

Tsuchida, K., "Myostatin inhibition by a follistatin-derived peptide ameliorates the pathophysiology of muscular dystrophy model mice", Acta Myologica, 27: 14-18 (2008).

Urlaub and Chasin, Isolation of Chinese hamster cell mutants deficient in dihydrofolate reductase activity, Proc. Natl. Acad. Sci. USA, 77(7): 4216-4220, 1980.

Wells, JA et al. "Additivity of mutational effects in proteins", Biochemistry 29(37): 8509-8517 (1990).

Written Opinion for PCT/US2014/012996, 7 pages (dated Jun. 2, 2015).

Yaden, B. et al., Follistatin: A Novel Therapeutic for the Improvement of Muscle Regeneration, The Journal of Pharmacology and Experimental Therapeutics, 349:355-371 (2014).

Zhu, J. et al., Follistatitin Improves Skeletal Muscle Healing After Injury and Disease Through an Interaction with Muscle Regeneration, Angiogenesis and Fibrosis, The American Journal of Pathology—Musculoskeletal Pathology, 179(2):915-930 (2011).

Injected Muscles

(A) 
(B)

Distal Muscles

(C) 
(D) 
(E)

Injected Muscles

(A) 
(B)

Distal Muscles

(C) 
(D) 
(E)

A)

B)

A)

B)

FOLLISTATIN IN TREATING DUCHENNE MUSCULAR DYSTROPHY

CROSS-REFERENCE TO RELATED APPLICATIONS

This application is a continuation application of U.S. Ser. No. 14/762,373, filed on Jul. 21, 2015, now U.S. Pat. No. 9,957,309, which is a U.S. National Stage Application filed under 35 U.S.C. § 371 based on International Application No. PCT/US2014/012996, filed Jan. 24, 2014, which claims priority to U.S. provisional patent application Ser. No. 61/756,996, filed Jan. 25, 2013, and U.S. provisional patent application Ser. No. 61/915,733, filed Dec. 13, 2013, the disclosures of each of which are hereby incorporated in their entirety.

INCORPORATION-BY-REFERENCE OF SEQUENCE LISTING

The instant application contains a Sequence Listing which has been submitted electronically in ASCII format and is hereby incorporated-by-reference in its entirety. The ASCII copy, created on Apr. 9, 2018 is named SHR-1093US2_ST25.txt and is 52 KB in size.

BACKGROUND

Duchenne muscular dystrophy (DMD) is a recessive X-linked form of muscular dystrophy, which results in muscle degeneration and eventual death. The disorder is caused by a mutation in the dystrophin gene, located on the human X chromosome, which codes for the protein dystrophin, an important structural component within muscle tissue that provides structural stability to the dystroglycan complex (DGC) of the cell membrane. Dystrophin links the internal cytoplasmic actin filament network and extracellular matrix, providing physical strength to muscle fibers. Accordingly, alteration or absence of dystrophin results in abnormal sarcolemmal membrane function. While persons of both sexes can carry the mutation, boys typically have a severe phenotype with early disability and mortality, whereas females carrying a mutation typically exhibit a much milder phenotype.

Presently, there is no known cure for DMD. Many therapeutic avenues have been investigated including gene therapy and various administration protocols of corticosteroids. While some of these treatments may delay certain signs and symptoms, there is presently no satisfactory therapeutic option for DMD patients.

SUMMARY OF THE INVENTION

The present invention provides, among other things, improved methods and compositions for treating muscular dystrophy, in particular, Duchenne muscular dystrophy (DMD) and/or Becker Muscular Dystrophy, based on follistatin protein therapy. As described herein, including in the Examples below, the present inventors demonstrated, for the first time, that systemic administration of a recombinant follistatin protein (e.g., a follistatin-Fc recombinant fusion protein) into a DMD animal model resulted in effective muscle growth in various tissues throughout the body and reduced muscle fibrosis and/or necrosis, characteristic symptoms of DMD. In addition, the present inventors have also demonstrated that follistatin-Fc fusion proteins according to the present invention have extended serum half-life of up to about 5 days. Without wishing to be bound by any theory, it is contemplated that the unexpectedly long serum half-life may have contributed to the superior in vivo efficacy. Indeed, prior to the present invention, follistatin was known to be a modulator of myostatin and activin, both of which are important negative regulators of muscle growth. However, prior to the present invention, it was reported that follistatin has a particularly short serum half-life, which constituted a significant hurdle for developing follistatin as a protein therapeutic. For example, a typical commercially available wild-type follistatin (FS315) protein has a serum half-life of about an hour. Fc-fusion protein had been used to extend the serum half-life of follistatin. However, due to the large size of the Fc domain and the relatively smaller size of the follistatin protein, it was thought that a direct fusion of the Fc domain to the follistatin protein may interfere with the normal structure and function of a wild-type follistatin protein. The reported poor pharmacokinetic/pharmacodynamic (PK/PD) properties of follistatin and uncertainty associated with follistatin-Fc fusion protein had discouraged scientists and clinicians from further developing follistatin as a protein therapy for DMD or other muscular dystrophy. Indeed, prior to the present invention, gene therapy has been the focus of follistatin based therapy for DMD. The unexpectedly superior in vivo efficacy and half-life shown by the present inventors establishes for the first time that follistatin can be an effective protein therapeutic for treatment of DMD.

In one aspect, the present invention provides methods of treating Duchenne Muscular Dystrophy (DMD) including administering to an individual who is suffering from or susceptible to DMD an effective amount of a recombinant follistatin protein such that at least one symptom or feature of DMD is reduced in intensity, severity, or frequency, or has delayed onset. In some embodiments, at least one symptom or feature of DMD is selected from the group consisting of muscle wasting, muscle weakness, muscle fragility, joint contracture, skeletal deformation, fatty infiltration of muscle, replacement of muscle with non-contractile tissue (e.g., muscle fibrosis), muscle necrosis, cardiomyopathy, impaired swallowing, impaired bowel and bladder function, muscle ischemia, cognitive impairment function (e.g., learning difficulties, higher risk of neurobehavioral disorders, cognitive defects), behavioral dysfunction, socialization impairment, scoliosis, and impaired respiratory function.

In some embodiments, a recombinant follistatin protein suitable for the present invention includes an amino acid sequence at least 50% (e.g., at least 55%, 60%, 65%, 70%, 75%, 80%, 85%, 90%, 95%, 96%, 97%, 98%, 99%, or 100%) identical to the wild-type human Follistatin protein (SEQ ID NO: 1)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEW.

In some embodiments, the recombinant follistatin protein includes an amino acid sequence at least 70% identical to the wild-type human Follistatin protein SEQ ID NO: 1. In some embodiments, the recombinant follistatin protein includes an amino acid sequence at least 80% identical to the wild-type human Follistatin protein SEQ ID NO: 1. In some embodiments, the recombinant follistatin protein includes an amino acid sequence at least 90% identical to the wild-type human Follistatin protein SEQ ID NO: 1. In some embodiments, the recombinant follistatin protein includes an amino acid sequence at least 95% identical to the wild-type human Follistatin protein SEQ ID NO: 1. In some embodiments, the recombinant follistatin protein includes an amino acid sequence identical to the wild-type human Follistatin protein SEQ ID NO:1.

In some embodiments, the recombinant follistatin protein comprises one or more deletions, mutations or insertions as compared to the wild-type human Follistatin protein. In some embodiments, the recombinant follistatin protein comprises a deletion of amino acids residues 212-288 of SEQ ID NO:1 (which corresponds to domain 3). In some embodiments, the recombinant follistatin protein comprises the heparin binding site.

In some embodiments, the present invention provides methods of treating Duchenne Muscular Dystrophy (DMD) including administering to an individual who is suffering from or susceptible to DMD an effective amount of a recombinant follistatin protein such that at least one symptom or feature of DMD is reduced in intensity, severity, or frequency, or has delayed onset, wherein the recombinant follistatin protein comprises an amino acid sequence at least 50% (e.g., at least 55%, 60%, 65%, 70%, 75%, 80%, 85%, 90%, 95%, 96%, 97%, 98%, 99%, or 100%) identical to

```
                                          (SEQ ID NO: 2)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCISISEDTEEEEEDEDQDYSFPISSILEW.
```

In some embodiments, the recombinant follistatin protein includes an amino acid sequence at least 70% identical to SEQ ID NO:2. In some embodiments, the recombinant follistatin protein includes an amino acid sequence at least 80% identical to SEQ ID NO:2. In some embodiments, the recombinant follistatin protein includes an amino acid sequence at least 90% identical to SEQ ID NO:2. In some embodiments, the recombinant follistatin protein includes an amino acid sequence at least 95% identical to SEQ ID NO:2. In some embodiments, the recombinant follistatin protein includes an amino acid sequence identical to SEQ ID NO:2.

In some embodiments, the at least one symptom or feature of DMD is selected from the group consisting of muscle wasting, muscle weakness, muscle fragility, muscle hypertrophy, muscle pseudohypertrophy, joint contracture, skeletal deformation, cardiomyopathy, impaired swallowing, impaired bowel and bladder function, muscle ischemia, cognitive impairment, behavioral dysfunction, socialization impairment, scoliosis, and impaired respiratory function.

In some embodiments, the recombinant follistatin protein is fused to an Fc domain. In some embodiments, an Fc domain suitable for the present invention comprises an amino acid sequence at least 50% (e.g., at least 55%, 60%, 65%, 70%, 75%, 80%, 85%, 90%, 95%, 96%, 97%, 98%, 99%, or 100%) identical to

```
                                          (SEQ ID NO: 3)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK;
or
                                          (SEQ ID NO: 4)
KTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGN

VFSCSVMHEALHNHYTQKSLSLSPGK;
or
                                          (SEQ ID NO: 14)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

In some embodiments, the Fc domain comprises an amino acid sequence at least 80% identical to SEQ ID NO: 3, 4, or 14. In some embodiments, the Fc domain comprises an amino acid sequence at least 90% identical to SEQ ID NO: 3, 4, or 14. In some embodiments, the Fc domain comprises an amino acid sequence at least 95% identical to SEQ ID NO:3, 4, or 14.

In some embodiments, a suitable Fc domain comprises one or more mutations that improve binding between the Fc domain and the FcRn receptor resulting in prolonged serum half-life. In some embodiments, a suitable Fc domain comprises one or more mutations at one or more positions corresponding to Thr 250, Met 252, Ser 254, Thr 256, Thr 307, Glu 380, Met 428, His 433 and/or Asn 434 of human IgG1. In particular embodiments, a suitable Fc domain contains mutations H433K (His433Lys) and/or N434F (Asn434Phe). In particular embodiments, a suitable Fc domain comprises a sequence shown below which incorporates the mutations of H433K (His433Lys) and N434F (Asn434Phe):

```
                                          (SEQ ID NO: 15)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALKFHYTQKSLSLSPGK.
```

In some embodiments, a recombinant follistatin protein is fused to the Fc domain via a linker. In some embodiments, the linker is a peptide comprising 3-100 amino acids. In some embodiments, the linker is not a linker consisting of ALEVLFQGP (SEQ ID NO: 18). In some embodiments, the linker comprises between 10-100, 10-90, 10-80, 10-70, 10-60, 10-50, 10-40, 10-30, 10-20, 10-15 amino acids. In some embodiments, the linker comprises at least 10, 15, 20, 25, 30, 35, 40, 45, 50, 55, 60, 65, 70, 75, 80, 85, 90, or 95 amino acids. In some embodiments, the linker comprises a sequence at least 50% (e.g., at least 55%, 60%, 65%, 70%, 75%, 80%, 85%, 90%, 95%, 96%, 97%, 98%, or 99%) identical to GAPGGGGGAAAAAGGGGGGAP (GAG linker, SEQ ID NO: 5). In some embodiments, the linker comprises a sequence at least 50% (e.g., at least 55%, 60%, 65%, 70%, 75%, 80%, 85%, 90%, 95%, 96%, 97%, 98%, or 99%) identical to GAPGGGGGAAAAAGGGGG GAPGGGGGAAAAAGGGGGGAP (GAG2 linker, SEQ ID NO: 6). In some embodiments, the linker comprises a sequence at least 50% (e.g., at least 55%, 60%, 65%, 70%, 75%, 80%, 85%, 90%, 95%, 96%, 97%, 98%, or 99%) identical to GAPGGGGGAAAAAGGGGG GAPGGGGGAAAAAGGGGG GAPGGGGGAAAAAGGGGG GAP (GAG3 linker, SEQ ID NO:7). In some embodiments, the linker comprises a sequence identical to SEQ ID NO:5, SEQ ID NO:6, or SEQ ID NO:7.

In some embodiments, the present invention provides a recombinant follistatin fusion protein including a follistatin polypeptide, an Fc domain, and a linker with a length of at least 10 (e.g., at least 15, 20, 25, 30, 35, 40, 45, 50, 55, 60, 65, 70, 75, 80, 85, 90, or 95) amino acids that associates the follistatin polypeptide with the Fc domain. In some embodiments, the present invention provides a recombinant follistatin fusion protein including a follistatin polypeptide, an Fc domain, and a linker that associates the follistatin polypeptide with the Fc domain, wherein the linker is not a linker consisting of ALEVLFQGP (SEQ ID NO: 18). In some embodiments, a suitable follistatin polypeptide comprises an amino acid sequence at least 50% (e.g., at least 55%, 60%, 65%, 70%, 75%, 80%, 85%, 90%, 95%, 96%, 97%, 98%, 99%, or 100%) identical to the wild-type human Follistatin protein (SEQ ID NO: 1). In some embodiments, the recombinant follistatin fusion protein is capable of binding to activin, myostatin and/or GDF-11 and has an in vivo half-life ranging from about 0.5-10 days.

In particular embodiments, a recombinant follistatin protein suitable for the present invention comprises an amino acid sequence at least 50% (e.g., at least 55%, 60%, 65%, 70%, 75%, 80%, 85%, 90%, 95%, 96%, 97%, 98%, 99%, or 100%) identical to SEQ ID NO:8

SEQ ID NO: 8
(SEQ ID NO: 8)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWGAPGGGGGAAAAAGGGGGAPGGGGGAAAAAGGGG

GGAPGGGGGAAAAAGGGGGAPKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK, or

SEQ ID NO: 9
(SEQ ID NO: 9)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWGAPGGGGGAAAAAGGGGGAPGGGGGAAAAAGGGG

GGAPGGGGGAAAAAGGGGGAPEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPGK.

In particular embodiments, a recombinant follistatin protein suitable for the present invention comprises an amino acid sequence at least 50% (e.g., at least 55%, 60%, 65%, 70%, 75%, 80%, 85%, 90%, 95%, 96%, 97%, 98%, 99%, or 100%) identical to SEQ ID NO:10

SEQ ID NO: 10
(SEQ ID NO: 10)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCISISEDTEEEEEDEDQDYSFPISSILEWGAPGGGGGAAAA

AGGGGGAPGGGGGAAAAAGGGGGAPGGGGGAAAAAGGGGGAPKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK, or

SEQ ID NO: 11
(SEQ ID NO: 11)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCISISEDTEEEEEDEDQDYSFPISSILEWGAPGGGGGAAAA

AGGGGGAPGGGGGAAAAAGGGGGAPGGGGGAAAAAGGGGGAPEPKSC

-continued

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

In particular embodiments, a recombinant follistatin protein suitable for the present invention comprises an amino acid sequence at least 50% (e.g., at least 55%, 60%, 65%, 70%, 75%, 80%, 85%, 90%, 95%, 96%, 97%, 98%, 99%, or 100%) identical to (SEQ ID NO: 16)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWGAPGGGGAAAAAGGGGGAPGGGGAAAAAGGGG

GGAPGGGGAAAAAGGGGGAPDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

Or (SEQ ID NO: 17)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWGAPGGGGAAAAAGGGGGAPGGGGAAAAAGGGG

GGAPGGGGAAAAAGGGGGAPDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALKFHYTQKSLSLSPGK

In some embodiments, a recombinant follistatin protein suitable for the present invention is produced from mammalian cells. In some embodiments, the mammalian cells are human cells. In some embodiments, the mammalian cells are Chinese Hamster Ovary (CHO) cells or HT1080 cells.

It will be appreciated that embodiments of the invention may be delivered via a variety of routes. In some embodiments, the recombinant follistatin protein is administered systemically. In some embodiments, the systemic administration is selected from intravenous, intradermal, inhalation, transdermal (topical), intraocular, intramuscular, subcutaneous, intramuscular, oral, and/or transmucosal administration.

Embodiments may be administered via a multiplicity of dosing regimens. In some embodiments, the recombinant follistatin protein is administered bimonthly, monthly, tri-weekly, biweekly, weekly, daily, or at variable intervals.

In some embodiments, the recombinant follistatin protein is delivered to one or more target tissues selected from striated muscle (e.g., skeletal muscle, cardiac muscle). In some embodiments, the recombinant follistatin protein is delivered to the heart. In some embodiments, the recombinant follistatin protein is delivered to skeletal muscle. In some embodiments, the recombinant follistatin protein is delivered to one or more skeletal muscles selected from Table 1. In some embodiments, the striated muscle (e.g., skeletal muscle) is selected from the group consisting of triceps, tibialis anterior, soleus, gastrocnemius, biceps, trapezius, deltoids, quadriceps, and diaphragm.

In some embodiments, the administration of the recombinant follistatin protein results in muscle regeneration, fibrosis reduction, increased muscle strength, increased flexibility, increased range of motion, increased stamina, reduced fatigability, increased blood flow, improved cognition, improved pulmonary function, inflammation inhibition, reduced muscle fibrosis and/or necrosis.

In another aspect, the present invention provides compositions used in various methods described herein. In some embodiments, the present invention provides recombinant follistatin fusion proteins including a follistatin polypeptide, an Fc domain, and a linker that associates the follistatin polypeptide with the Fc domain, wherein the follistatin polypeptide comprises an amino acid sequence at least at least 50% (e.g., at least 55%, 60%, 65%, 70%, 75%, 80%, 85%, 90%, 95%, 96%, 97%, 98%, 99%, or 100%) identical to the wild-type human follistatin protein (SEQ ID NO: 1). In some embodiments, the recombinant follistatin fusion protein is capable of binding to activins, myostatin and/or GDF-11. In some embodiments, the recombinant follistatin fusion protein has an in vivo half-life greater than about 2 days (e.g., greater than about 2.5 days, about 3 days, about 3.5 days, about 4 days, about 4.5 days, about 5 days, about 5.5 days, about 6 days). In some embodiments, the recombinant follistatin fusion protein has an in vivo half-life ranging from about 2-10 days (e.g., ranging from about 2.5-10 days, from about 3-10 days, from about 3.5-10 days, from about 4-10 days, from about 4.5-10 days, from about 5-10 days, from about 3-8 days, from about 3.5-8 days, from about 4-8 days, from about 4.5-8 days, from about 5-8 days, from about 3-6 days, from about 3.5-6 days, from about 4-6 days, from about 4.5-6 days, from about 5-6 days). In some embodiments, the in vivo half-life is measured in one or more of mice, rats, non-human primates, and/or humans. In some embodiments, the follistatin polypeptide has an amino acid sequence at least 70% identical to the wild-type human follistatin protein (SEQ ID NO: 1). In some embodiments, the follistatin polypeptide has an amino acid sequence at least 80% identical to the wild-type human follistatin protein (SEQ ID NO: 1). In some embodiments, the follistatin polypeptide has an amino acid sequence at least 90% identical to the wild-type human follistatin protein (SEQ ID NO: 1). In some embodiments, the follistatin polypeptide has an amino acid sequence at least 95% identical to the wild-type human follistatin protein (SEQ ID NO: 1). In some embodiments, the follistatin polypeptide has an amino acid sequence identical to the wild-type human follistatin protein (SEQ ID NO: 1). In some embodiments, the follistatin polypeptide contains a deletion of amino acids residues 212-288 of SEQ ID NO:1 (which corresponds to domain 3). In various embodiments, the follistatin polypeptide contains the heparin sulfate binding site.

In some embodiments, the present invention provides recombinant follistatin fusion proteins including a follistatin polypeptide, an Fc domain, and a linker that associates the follistatin polypeptide with the Fc domain, wherein the follistatin polypeptide comprises an amino acid sequence at least 50% (e.g., at least 55%, 60%, 65%, 70%, 75%, 80%, 85%, 90%, 95%, 96%, 97%, 98%, 99%, or 100%) identical to (SEQ ID NO: 2)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCISISEDTEEEEEDEDQDYSFPISSILEW.

In some embodiments, the recombinant follistatin fusion protein is capable of binding to activins, myostatin and/or GDF-11. In some embodiments, the recombinant follistatin fusion protein has an in vivo half-life greater than about 2 days (e.g., greater than about 2.5 days, about 3 days, about 3.5 days, about 4 days, about 4.5 days, about 5 days, about 5.5 days, about 6 days). In some embodiments, the recombinant follistatin fusion protein has an in vivo half-life ranging from about 2-10 days (e.g., ranging from about 2.5-10 days, from about 3-10 days, from about 3.5-10 days, from about 4-10 days, from about 4.5-10 days, from about 5-10 days, from about 3-8 days, from about 3.5-8 days, from about 4-8 days, from about 4.5-8 days, from about 5-8 days, from about 3-6 days, from about 3.5-6 days, from about 4-6 days, from about 4.5-6 days, from about 5-6 days). In some embodiments, the in vivo half-life is measured in one or more of mice, rats, non-human primates, and/or humans.

In some embodiments, the Fc domain is an IgG1 Fc domain. In some embodiments, the Fc domain has an amino acid sequence at least 50% (e.g., at least 55%, 60%, 65%, 70%, 75%, 80%, 85%, 90%, 95%, 96%, 97%, 98%, 99%, or 100%) identical to (SEQ ID NO: 3)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK;
or (SEQ ID NO: 4)
KTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGN

VFSCSVMHEALHNHYTQKSLSLSPGK;
or (SEQ ID NO: 14)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

In some embodiments, a suitable Fc domain comprises one or more mutations that improve binding between the Fc domain and the FcRn receptor resulting in prolonged serum half-life. In some embodiments, the Fc domain comprises one or more mutations at one or more positions corresponding to Thr 250, Met 252, Ser 254, Thr 256, Thr 307, Glu 380, Met 428, His 433, and/or Asn 434 of human IgG. In particular embodiments, a suitable Fc domain contains mutations H433K (His433Lys) and/or N434F (Asn434Phe). In particular embodiments, a suitable Fc domain comprises a sequence shown below which incorporates the mutations of H433K (His433Lys) and N434F (Asn434Phe):

(SEQ ID NO: 15)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALKFHYTQKSLSLSPGK.

In some embodiments, a recombinant follistatin fusion protein according to the present invention includes a linker such that the Fc fusion via the linker does not substantially change the binding properties of follistatin to cognate ligands, including maintaining the lack of binding to heparin. In some embodiments, a suitable linker is a peptide comprising 3-60 amino acids. In some embodiments, a suitable linker is a peptide comprising at least 10 (e.g., at least 15, 20, 25, 30, 35, 40, 45, 50, 55, 60, 65, 70, 75, 80, 85, 90, or 95) amino acids. In some embodiments, a suitable linker comprises a sequence at least 50% (e.g., at least 55%, 60%, 65%, 70%, 75%, 80%, 85%, 90%, 95%, 96%, 97%, 98%, 99%, or 100%) identical to <u>GAP</u>GGGGGAAAAAGGGGG<u>GAP</u> (GAG linker, SEQ ID NO: 5). In some embodiments, a suitable linker comprises a sequence at least 50% (e.g., at least 55%, 60%, 65%, 70%, 75%, 80%, 85%, 90%, 95%, 96%, 97%, 98%, 99%, or 100%) identical to <u>GAP</u>GGGGGAAAAAGGGGG<u>GAP</u>GGGGGAAAAAGGGGG<u>GAP</u> (GAG2 linker, SEQ ID NO: 6). In some embodiments, a suitable linker comprises a sequence at least 50% (e.g., at least 55%, 60%, 65%, 70%, 75%, 80%, 85%, 90%, 95%, 96%, 97%, 98%, 99%, or 100%) identical to <u>GAP</u>GGGGGAAAAAGGGGG <u>GAP</u>GGGGGAAAAAGGGGG <u>GAP</u>GGGGGAAAAAGGGGG <u>GAP</u> (GAG3 linker, SEQ ID NO:7).

In particular embodiments, a recombinant follistatin fusion protein provided by the present invention comprises an amino acid sequence at least 50% (e.g., at least 55%, 60%, 65%, 70%, 75%, 80%, 85%, 90%, 95%, 96%, 97%, 98%, 99%, or 100%) identical to SEQ ID NO:8, 9, 10, 11, 16 or 17:

In some embodiments, the present invention provides nucleic acids comprising a nucleotide sequence encoding a recombinant follistatin fusion protein described herein. In some embodiments, the present invention provides a cell comprising a nucleic acid comprising a nucleotide sequence encoding a recombinant follistatin fusion protein described herein. In some embodiments, the present invention provides pharmaceutical compositions comprising a recombinant follistatin fusion protein described herein and a pharmaceutically acceptable carrier.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The drawings are for illustration purposes only not for limitation.

FIG. 1A shows exemplary results of the BMP-9 inhibition assay and FIG. 1B shows exemplary results of the BMP-10 inhibition assay. FS315-Fc does not inhibit BMP-9 or -10 signaling through Smad 1/5/8 pathway (BRE-luciferase reporter assay).

FIG. 2A shows exemplary results of the myostatin inhibition assay and FIG. 2B shows exemplary results of an activin A inhibition assay. FS315-GAG3-mFc inhibits myostatin and activin A signaling through Smad2/3 pathway (CAGA-luciferase reporter assay).

FIG. 3 shows FS315-mFc PK profile in mouse serum and tissue after SC injection of 1 mg/kg. Estimated tissue half-life is 2-5 days, serum half-life is ~5 days.

FIG. 4 shows changes in muscle mass after twice weekly SC administration of FS315-mFc into mdx mice. The muscle weights are normalized to baseline body weight. There is a trend for increased muscle weight in mdx mice treated with 1 mg/kg for 10 weeks or 8 mg/kg for 6 weeks.

FIG. 5A. shows the levels in the serum after treatment with 1 mg/kg FS315-mFc over 10 weeks, and FIG. 5B. shows the levels in the serum after treatment with 8 mg/kg FS315-mFc over 6 weeks. FIG. 5 shows the levels of FS315-mFc in serum of mdx mice treated with 1 mg/kg (FIG. 5A) and 8 mg/kg (FIG. 5B).

FIG. 6 shows the effect of intramuscular injection of FS315-mFc on muscle weight after 4 weeks of twice weekly injection of 20 g directly into the gastrocnemius muscle. The contra-lateral gastrocnemius muscle received an equivalent volume of PBS and acts as the control for each treatment group. The untreated group did not receive injections, and each data set for this group represents right and left gastrocnemius muscles. P-values obtained from paired t-test with Bonferroni correction.

FIG. 7 shows weekly body weight after intramuscular gene delivery of follistatin variants to gastrocnemius and quadriceps muscle of C57 mice.

FIG. 8 shows week 2 muscle weights after intramuscular gene delivery of follistatin variants to gastrocnemius (FIG. 8, panel A) and quadriceps (FIG. 8, panel B) muscle of C57 mice.

FIG. 9 shows week 2 gross morphology of dissected quadriceps muscle receiving dFSD3 via direct gene delivery. The right quad muscle did not receive an injection of dFSD3.

FIG. 10 shows week 4 muscle weights after intramuscular gene delivery of follistatin variants to gastrocnemius (FIG. 10, panel A), and quadriceps muscle (FIG. 10, panel B) of C57 mice. The following muscles were remote from the injection site: tibialis anterior (FIG. 10, panel C), triceps (FIG. 10, panel D), and diaphragm (FIG. 10, panel E).

FIG. 11 shows week 4 gross morphology of quadriceps muscle receiving dFSD3 via direct gene delivery. The right quad muscle did not receive an injection of dFSD3.

FIG. 12 shows week 2 muscle myofiber diameter after intramuscular gene delivery of follistatin variants to quadriceps (FIG. 12, panel A) and gastrocnemius muscle (FIG. 12, panel B) of C57 mice. The following muscles were remote from the injection site: tibialis anterior (FIG. 12, panel C), triceps (FIG. 12, panel D), and diaphragm (FIG. 12, panel E).

FIG. 13 shows week 4 muscle myofiber diameter after intramuscular gene delivery of follistatin variants to quadriceps (FIG. 13, panel A) and gastrocnemius muscle (FIG. 13, panel B) of C57 mice. The following muscles were remote from the injection site: tibialis anterior (FIG. 13, panel C), triceps (FIG. 13, panel D), and diaphragm (FIG. 13, panel E).

FIG. 14 shows week 6 muscle myofiber diameter after intramuscular gene delivery of follistatin variants to quadriceps (FIG. 14, panel A) and gastrocnemius muscle (FIG. 14, panel B) of C57 mice. The following muscles were remote from the injection site: tibialis anterior (FIG. 14, panel C), triceps (FIG. 14, panel D), and diaphragm (FIG. 14, panel E).

FIG. 15 shows size distribution of myofibers after intramuscular FS315-mFc injection into the gastrocnemius of C57 (WT) (FIG. 15, panel A) or mdx (FIG. 15, panel B) mice.

FIG. 16 shows body weights of C57 mice treated twice weekly for 8 weeks with 10 mg/kg FS315-mFc via subcutaneous injection. P values were obtained using unpaired t-test.

FIG. 17 shows percent change in weight for triceps and quadriceps muscles in FS315-mFc treated C57 mice at week 4 and 8 is shown. P values were obtained from unpaired t-test.

FIG. 18 shows percent increase over vehicle control of triceps and quadriceps myofiber diameters in FS315-mFc treated C57 mice at week 4 and 8. P values were obtained from unpaired t-test.

FIG. 19 shows levels of FS315-mFc in serum after twice weekly subcutaneous injection of 10 mg/kg into C57 mice. On the X-axis, "Week" refers to week of treatment course. The number of days post-injection of FS315-mFc, corresponding to when the serum was collected, is included in parentheses. The vehicle treated mice had no detectable follistatin in the serum.

FIG. 20 shows mRNA levels of key markers of fibrosis after 6 and 12 weeks of FS315-mFc treatment of mdx mice. RT-PCR was used to quantitate mRNA levels of each protein in quadriceps of treated mice (n=15 animals per time point). P-values were obtained from a one-way ANOVA followed by Tukey's posthoc pairwise comparison test or its nonparametric analogue.

FIG. 21 shows H&E stained sections of quadriceps and triceps muscle after 6 weeks of twice weekly treatment with 10 mg/kg FS315-mFc. The outlined areas indicate necrotic tissue. The C57 panel represents healthy, unaffected muscle.

FIG. 22 shows collagen I stained sections of diaphragm, quadriceps and triceps muscle after 12 weeks of twice weekly treatment with 10 mg/kg FS315-mFc. The stained areas indicate collagen I deposition and fibrosis. The C57 panel represents healthy, unaffected muscle.

FIG. 23 shows the pharmacodynamics effect of FS315-mFc and dFSD3-mFc on injected muscle weights after twice weekly injections of 20 tag directly into the gastrocnemius muscle for 4 weeks. P values were obtained from paired t-test (follistatin treated compared to vehicle control).

FIG. 24 shows FS315-GAG-mFc and -hFc inhibit (A) myostatin and (B) activin signaling through Smad2/3 pathway (CAGA-luciferase reporter assay) to a greater extent compared to the commercially available FS315-(9 linker)-hFc protein (Sino biological).

FIG. 25 shows FS315-hFc PK profile in rat serum after SC injection of 10 mg/kg. Estimated serum half-life ~3.5 days.

DEFINITIONS

Figure 1:
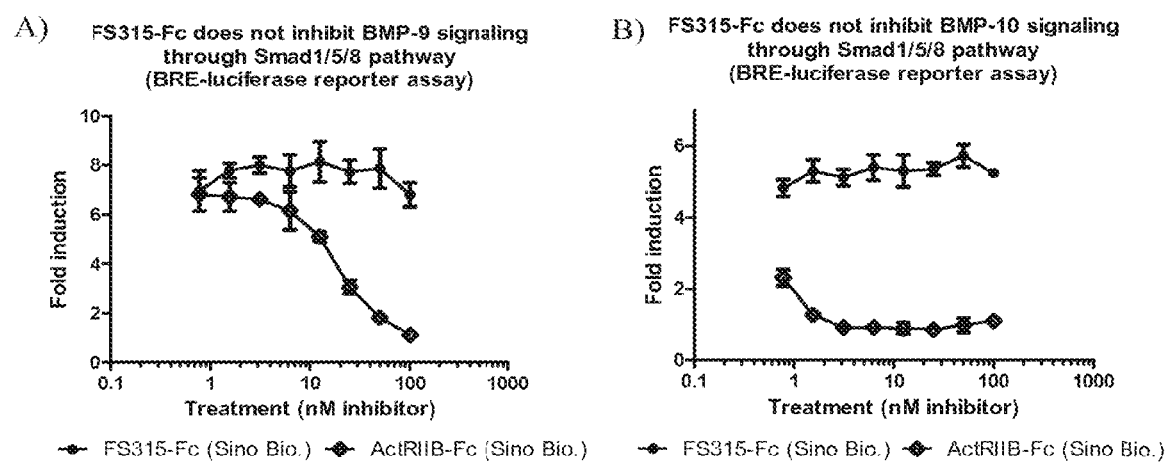
FIG. 1 shows exemplary results illustrating that FS315-Fc does not inhibit BMP-9 or BMP-10 signaling through the Smad 1/5/8 pathway as compared to a commercially available soluble activin receptor (sActRIIB).

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Bioavailability: As used herein, the term "bioavailability" generally refers to the percentage of the administered dose that reaches the blood stream of a subject.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion.

Cardiac Muscle: As used herein, the term "cardiac muscle" refers to a type of involuntary striated muscle found in the walls of the heart, and particularly the myocardium.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Follistatin or recombinant follistatin: As used herein, the term "follistatin (FS)" or "recombinant follistatin" refers to any wild-type and modified follistatin proteins (e.g., follistatin proteins with amino acid mutations, deletions, insertions, and/or fusion proteins) that retain substantial follistatin biological activity unless otherwise specified. A non-limiting example of deletions is a domain 3 deletion (ΔD3 or dFSD3). A non-limiting example of fusion proteins is an Fc-fusion protein.

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Fusion protein: As used herein, the term "fusion protein" or "chimeric protein" refers to a protein created through the joining of two or more originally separate proteins, or portions thereof. In some embodiments, a linker or spacer will be present between each protein.

Half-Life: As used herein, the term "half-life" is the time required for a quantity such as protein concentration or activity to fall to half of its value as measured at the beginning of a time period.

Hypertrophy: As used herein the term "hypertrophy" refers to the increase in volume of an organ or tissue due to the enlargement of its component cells.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Linker: As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer. A linker or a spacer typically does not have biological function on its own.

Polypeptide: The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. As used herein, the terms "polypeptide" and "peptide" are used inter-changeably.

Prevent: As used herein, the term "prevent" or "prevention", when used in connection with the occurrence of a disease, disorder, and/or condition, refers to reducing the risk of developing the disease, disorder and/or condition. See the definition of "risk."

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., muscular dystrophy). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., muscular dystrophy). In some embodiments a reference sample or group of reference samples are from individuals comparable to a particular individual. In some embodiments, relative risk is 0, 1, 2, 3, 4, 5, 6, 7, 8, 9, 10, or more.

Striated muscle: As used herein, the term "striated muscle" refers to multinucleated muscle tissue with regular arrangement of their intracellular contractile units, sarcomeres, leading to the appearance of striations using microscopy and under voluntary control. Typically, striated muscle can be cardiac muscle, skeletal muscle, and Branchiomeric muscles.

Smooth muscle: As used herein, the term "smooth muscle" refers to involuntarily controlled, non-striated muscle, including unitary and multi-unit muscle.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, DMD) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Target tissues: As used herein, the term "target tissues" refers to any tissue that is affected by a disease to be treated such as Duchenne muscular dystrophy (DMD). In some embodiments, target tissues include those tissues that display disease-associated pathology, symptom, or feature, including but not limited to muscle wasting, skeletal deformation, cardiomyopathy, and impaired respiratory function.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, methods and compositions for treating muscular dystrophy, including Duchenne muscular dystrophy (DMD) and/or Becker Muscular Dystrophy, based on follistatin as a protein therapeutic. In some embodiments, the present invention provides methods of treating DMD including administering to an individual who is suffering from or susceptible to DMD an effective amount of a recombinant follistatin protein such that at least one symptom or feature of DMD is reduced in intensity, severity, or frequency, or has delayed onset.

Various aspects of the invention are described in detail in the following sections. The use of sections is not meant to limit the invention. Each section can apply to any aspect of the invention. In this application, the use of "or" means "and/or" unless stated otherwise.

Duchenne Muscular Dystrophy (DMD)

DMD is a disease characterized by progressive deterioration of muscles and loss of muscle related functions throughout the body. It is contemplated that the present invention provides methods and compositions for regenerating muscle and treating fibrosis, inflammation and other symptoms or features associated with DMD and other muscular dystrophies in various muscle tissues. In some embodiments, use of provided methods and compositions in a subject result in a decrease fibrosis and/or necrosis in that subject.

Muscle Tissues

There are two major types of muscle tissue in an animal—striated muscle and smooth muscle. As used herein, the term "striated muscle" refers to muscle tissues containing repeating sarcomeres. Striated muscle tends to be under voluntary control and attached to the skeleton, though there are some exceptions, such as cardiac muscle, which has several properties of striated muscle, but is not under voluntary control. Generally, striated muscle allows for voluntary movement of the body and includes the major muscle groups including the quadriceps, gastrocnemius, biceps, triceps, trapezius, deltoids, and many others. Striated muscle tends to be very long and, many striated muscles are able to function independently. Some striated muscle, however, is not attached to the skeleton, including those in the mouth, anus, heart, and upper portion of the esophagus.

Smooth muscle, on the other hand, has very different structure. Rather than a series of long muscles with separate skeletal attachments, smooth muscle tends to be organized into continuous sheets with mechanical linkages between smooth muscle cells. Smooth muscle is often located in the walls of hollow organs and is usually not under voluntary control. Smooth muscles lining a particular organ must bear the same load and contract concurrently. Smooth muscle functions, at least in part, to handle changes in load on hollow organs caused by movement and/or changes in posture or pressure. This dual role means that smooth muscle must not only be able to contract like striated muscle, but also that it must be able to contract tonically to maintain organ dimensions against sustained loads. Examples of smooth muscles are those lining blood vessels, bladder, gastrointestinal track such as rectum.

The strength of a muscle depends on the number and sizes of the muscle's cells and on their anatomic arrangement. Increasing the diameter of a muscle fiber either by the increase in size of existing myofibrils (hypertrophy) and/or the formation of more muscle cells (hyperplasia) will increase the force-generating capacity of the muscle.

Muscles may also be grouped by location or function. In some embodiments, a recombinant follistatin protein is targeted to one or more muscles of the face, one or more muscles for mastication, one or more muscles of the tongue and neck, one or more muscles of the thorax, one or more muscles of the pectoral girdle and arms, one or more muscles of the arm and shoulder, one or more ventral and dorsal forearm muscles, one or more muscles of the hand, one or more muscles of the erector spinae, one or more muscles of the pelvic girdle and legs, and/or one or more muscles of the foreleg and foot.

In some embodiments, muscles of the face include, but are not limited to, intraocular muscles such as ciliary, iris dilator, iris sphincter; muscles of the ear such as auriculares, temporoparietalis, stapedius, tensor tympani; muscles of the nose such as procerus, nasalis, dilator naris, depressor septi nasi, levator labii superioris alaeque nasi; muscles of the mouth such as levator anguli oris, depressor anguli oris, orbicularis oris, Buccinator, Zygomaticus Major and Minor, Platysma, Levator Labii Superioris, Depressor Labii Inferioris, Risorius, Mentalis, and/or Corrugator Supercilii.

In some embodiments, muscles of mastication include, but are not limited to, Masseter, Temporalis, Medial Pterygoid, Lateral Pterygoid. In some embodiments, muscles of the tongue and neck include, but are not limited to, Genioglossus, Styloglossus, Palatoglossus, Hyoglossus, Digastric, Stylohyoid, Mylohyoid, Geniohyoid, Omohyoid, Sternohyoid, Sternothyroid, Thyrohyoid, Sternocleidomastoid, Anterior Scalene, Middle Scalene, and/or Posterior Scalene.

In some embodiments, muscles of the thorax, pectoral girdle, and arms include, but are not limited to, Subclavius Pectoralis major, Pectoralis minor, Rectus abdominis, External abdominal oblique, Internal abdominal oblique, Transversus Abdominis, Diaphragm, External Intercostals, Internal Intercostals, Serratus Anterior, Trapezius, Levator Scapulae, Rhomboideus Major, Rhomboideus Minor, Latissimus dorsi, Deltoid, subscapularis, supraspinatus, infraspinatus, Teres major, Teres minor, and/or Coracobrachialis.

In some embodiments, muscles of the arm and shoulder include, but are not limited to, Biceps brachii-Long Head, Biceps brachii-Short Head, Triceps brachii-Long Head, Triceps brachii Lateral Head, Triceps brachii-Medial Head, Anconeus, Pronator teres, Supinator, and/or Brachialis.

In some embodiments, muscles of the ventral and dorsal forearm include, but are not limited to, Brachioradialis, Flexor carpi radialis, Flexor carpi ulnaris, Palmaris longus, Extensor carpi ulnaris, Extensor carpi radialis longus, Extensor carpi radialis brevis, Extensor digitorum, Extensor digiti minimi.

In some embodiments, muscles of the hand include, but are not limited to intrinsic muscles of the hand such as thenar, abductor pollicis brevis, flexor pollicis brevis, opponens pollicis, hypothenar, abductor digiti minimi, the flexor digiti minimi brevis, opponens digiti minimi, palmar interossei, dorsal interossei and/or lumbricals.

In some embodiments, muscles of the erector spinae include, but are not limited to, cervicalis, spinalis, longissimus, and/or iliocostalis.

In some embodiments, muscles of the pelvic girdle and the legs include, but are not limited to, Psoas Major, Iliacus, quadratus femoris, Adductor longus, Adductor brevis, Adductor magnus, Gracilis, Sartorius, Quadriceps femoris such as, rectus femoris, vastus lateralis, vastus medialis, vastus intermedius, Gastrocnemius, Fibularis (Peroneus) Longus, Soleus, Gluteus maximus, Gluteus medius, Gluteus minimus, Hamstrings: Biceps Femoris: Long Head, Hamstrings: Biceps Femoris: Short Head, Hamstrings: Semitendinosus, Hamstrings: Semimembranosus, Tensor fasciae latae, Pectineus, and/or Tibialis anterior.

In some embodiments, muscles of the foreleg and foot include, but are not limited to, Extensor digitorum longus, Extensor hallucis longus, peroneus brevis, plantaris, Tibialis posterior, Flexor hallucis longus, extensor digitorum brevis, extensor hallucis brevis, Abductor hallucis, flexor hallucis brevis, Abductor digiti minimi, flexor digiti minimi, opponens digiti minimi, extensor digitorum brevis, lumbricales of the foot, Quadratus plantae or flexor accessorius, flexor digitorum brevis, dorsal interossei, and/or plantar interossei.

Exemplary muscle targets are summarized in Table 1.

TABLE 1

| ORBICULARIS OCULI | | | |
| --- | --- | --- | --- |
| Intraocular: ciliary, iris dilator, iris sphincter | | | |
| Ear: auriculares, temporoparietalis, stapedius, tensor tympani | | | |
| Nose: procerus, nasalis, dilator naris, depressor septi nasi, levator labii superioris alaeque nasi | | | |
| Mouth: levator anguli oris, depressor anguli oris, orbicularis oris | | | |
| Buccinator | Zygomaticus Major and Minor | Platysma | Levator Labii Superioris |
| Depressor Labii Inferioris | Risorius | Mentalis | Corrugator Supercilii |
| Anconeus | Pronator teres | Supinator | Brachialis |
| MUSCLES OF MASTICATON | | | |
| Masseter | Temporalis | Medial Pterygoid | Lateral Pterygoid |
| MUSCLES OF THE TONGUE AND NECK | | | |
| Genioglossus | Styloglossus | Palatoglossus | Hyoglossus |
| Digastric | Stylohyoid | Mylohyoid | Geniohyoid |
| Omohyoid | Sternohyoid | Sternothyroid | Thyrohyoid |
| Sternocleidomastoid | Anterior Scalene | Middle Scalene | Posterior Scalene |
| MUSCLES OF THE THORAX, PECTORAL GIRDLE AND ARMS | | | |
| Subclavius | Pectoralis major | Pectoralis minor | Rectus abdominis |
| External abdominal oblique | Internal abdominal oblique | Transversus Abdominis | Diaphragm |
| External Intercostals | Internal Intercostals | Serratus Anterior | Trapezius |
| Levator Scapulae | Rhomboideus Major | Rhomboideus Minor | Latissimus dorsi |
| Deltoid | subscapularis | supraspinatus | infraspinatus |
| Teres major | Teres minor | Coracobrachialis | |
| ARM AND SHOULDER | | | |
| Biceps brachii-Long Head | Biceps brachii-Short Head | Triceps brachii-Long Head | Triceps brachii-Lateral Head |
| Triceps brachii-Medial Head | Anconeus | Pronator teres | Supinator |
| Brachialis | | | |
| FOREARM MUSCLES: Ventral and Dorsal | | | |
| Brachioradialis | Flexor carpi radialis | Flexor carpi ulnaris | Palmaris longus |

TABLE 1-continued

| Extensor carpi ulnaris | Extensor carpi radialis longus | Extensor carpi radialis brevis | Extensor digitorum |
|---|---|---|---|
| Extensor digiti minimi | erector spinae: cervicalis | erector spinae: spinalis | erector spinae: longissimus |
| erector spinae: iliocostalis | | | |

Intrinsic Muscles of the Hand: thenar, abductor pollicis brevis, flexor pollicis brevis, and the opponens pollicis
Intrinsic Muscles of the Hand: hypothenar, abductor digiti minimi, the flexor digiti minimi brevis, and the opponens digiti minimi
Intrinsic Muscles of the Hand: palmar interossei, dorsal interossei and lumbricals

MUSCLES OF THE PELVIC GIRDLE AND THE LEGS

| Iliopsoas: Psoas Major | Iliopsoas: Iliacus | quadratus femoris | Adductor longus |
|---|---|---|---|
| Adductor brevis | Adductor magnus | Gracilis | Sartorius |
| Quadriceps femoris: rectus femoris | Quadriceps femoris: vastus lateralis | Quadriceps femoris: vastus medialis | Quadriceps femoris: vastus intermedius |
| Gastrocnemius | Fibularis (Peroneus) Longus | Soleus | Gluteus maximus |
| Gluteus medius | Gluteus minimus | Hamstrings: Biceps Femoris: Long Head | Hamstrings: Biceps Femoris: Short Head |
| Hamstrings: Semitendinosus | Hamstrings: Semimembranosus | Tensor fasciae latae | Pectineus |
| Tibialis anterior | | | |

MUSCLES OF THE FORELEG AND FOOT

| Extensor digitorum longus | Extensor hallucis longus | peroneus brevis | plantaris |
|---|---|---|---|
| Tibialis posterior | Flexor hallucis longus | extensor digitorum brevis | extensor hallucis brevis |
| Abductor hallucis | flexor hallucis brevis | Abductor digiti minimi | flexor digiti minimi |
| opponens digiti minimi | extensor digitorum brevis | lumbricales of the foot | Quadratus plantae or flexor accessorius |
| Flexor digitorum brevis | dorsal interossei | plantar interossei | |

Muscular Dystrophy

Muscular dystrophies are a group of inherited disorders that cause degeneration of muscle, leading to weak and impaired movements. A central feature of all muscular dystrophies is that they are progressive in nature. Muscular dystrophies include, but are not limited to: Duchenne muscular dystrophy (DMD), Becker muscular dystrophy, Emery-Dreifuss muscular dystrophy, facioscapulohumeral muscular dystrophy, limb-girdle muscular dystrophies, and myotonic dystrophy Types 1 and 2, including the congenital form of Myotonic dystrophy Type 1. Symptoms may vary by type of muscular dystrophy with some or all muscles being affected. Exemplary symptoms of muscular dystrophies include delayed development of muscle motor skills, difficulty using one or more muscle groups, difficulty swallowing, speaking or eating, drooling, eyelid drooping, frequent falling, loss of strength in a muscle or group of muscles as an adult, loss in muscle size, problems walking due to weakness or altered biomechanics of the body, muscle hypertrophy, muscle pseudohypertrophy, fatty infiltration of muscle, replacement of muscle with non-contractile tissue (e.g., muscle fibrosis), muscle necrosis, and/or cognitive or behavioral impairment/mental retardation.

While there are no known cures for muscular dystrophies, several supportive treatments are used which include both symptomatic and disease modifying therapies. Corticosteroids, physical therapy, orthotic devices, wheelchairs, or other assistive medical devices for ADLs and pulmonary function are commonly used in muscular dystrophies. Cardiac pacemakers are used to prevent sudden death from cardiac arrhythmias in Myotonic dystrophy. Anti-myotonic agents which improve the symptoms of myotonia (inability to relax) include mexilitine, and in some cases phenytoin, procainamide and quinine.

Duchenne Muscular Dystrophy

Duchenne muscular dystrophy (DMD) is a recessive X-linked form of muscular dystrophy which results in muscle degeneration and eventual death. DMD is characterized by weakness in the proximal muscles, abnormal gait, psuedohypertrophy in the gastrocnemius (calf) muscles, and elevated creatine kinase (CK). Many DMD patients are diagnosed around the age of 5, when symptoms/signs typically become more obvious. Affected individuals typically stop walking around age 10-13 and die in or before their mid to late 20's due to cardiorespiratory dysfunction.

The disorder DMD is caused by a mutation in the dystrophin gene, located on the human X chromosome, which codes for the protein dystrophin, an important structural component within muscle tissue that provides structural stability to the dystroglycan complex (DGC) of the cell membrane. Dystrophin links the internal cytoplasmic actin filament network and extracellular matrix, providing physical strength to muscle fibers. Accordingly, alteration or absence of dystrophin results in abnormal sarcolemmal membrane tearing and necrosis of muscle fibers. While persons of both sexes can carry the mutation, females rarely exhibit severe signs of the disease.

A main symptom of DMD is muscle weakness associated with muscle wasting with the voluntary muscles being first affected typically, especially affecting the muscles of the hips, pelvic area, thighs, shoulders, and calf muscles. Muscle weakness also occurs in the arms, neck, and other areas. Calves are often enlarged. Signs and symptoms usually appear before age 6 and may appear as early as infancy. Other physical symptoms include, but are not limited to, delayed ability to walk independently, progressive difficulty in walking, stepping, or running, and eventual loss of ability to walk (usually by the age of 15); frequent falls; fatigue; difficulty with motor skills (running, hopping, jumping); increased lumbar lordosis, leading to shortening of the hip-flexor muscles; contractures of achilles tendon and hamstrings impairing functionality because the muscle fibers shorten and fibrosis occurs in connective tissue; muscle fiber deformities; pseudohypertrophy (enlargement) of tongue and calf muscles caused by replacement of muscle tissue by fat and connective tissue; higher risk of neurobehavioral disorders (e.g., ADHD), learning disorders (dyslexia), and non-progressive weaknesses in specific cognitive skills (in particular short-term verbal memory); skeletal deformities (including scoliosis in some cases).

Recombinant Follistatin Proteins

As used herein, recombinant follistatin proteins suitable for the present invention include any wild-type and modified follistatin proteins (e.g., follistatin proteins with amino acid mutations, deletions, insertions, and/or fusion proteins) that retain substantial follistatin biological activity. Typically, a recombinant follistatin protein is produced using recombinant technology. However, follistatin proteins (wild-type or modified) purified from natural resources or synthesized chemically can be used according to the present invention. Typically, a suitable recombinant follistatin protein has an in vivo half-life of or greater than about 12 hours, 18 hours, 24 hours, 36 hours, 2 days, 2.5 days, 3 days, 3.5 days, 4 days, 4.5 days, 5 days, 5.5 days, 6 days, 6.5 days, 7 days, 7.5 days, 8 days, 8.5 days, 9 days, 9.5 days, or 10 days. In some embodiments, a recombinant follistatin protein has an in vivo half-life of between 0.5 and 10 days, between 1 day and 10 days, between 1 day and 9 days, between 1 day and 8 days, between 1 day and 7 days, between 1 day and 6 days, between 1 day and 5 days, between 1 day and 4 days, between 1 day and 3 days, between 2 days and 10 days, between 2 days and 9 days, between 2 days and 8 days, between 2 days and 7 days, between 2 days and 6 days, between 2 days and 5 days, between 2 days and 4 days, between 2 day and 3 days, between 2.5 days and 10 days, between 2.5 days and 9 days, between 2.5 days and 8 days, between 2.5 days and 7 days, between 2.5 days and 6 days, between 2.5 days and 5 days, between 2.5 days and 4 days, between 3 days and 10 days, between 3 days and 9 days, between 3 days and 8 days, between 3 days and 7 days, between 3 days and 6 days, between 3 days and 5 days, between 3 days and 4 days, between 3.5 days and 10 days, between 3.5 days and 9 days, between 3.5 days and 8 days, between 3.5 days and 7 days, between 3.5 days and 6 days, between 3.5 days and 5 days, between 3.5 days and 4 days, between 4 days and 10 days, between 4 days and 9 days, between 4 days and 8 days, between 4 days and 7 days, between 4 days and 6 days, between 4 days and 5 days, between 4.5 days and 10 days, between 4.5 days and 9 days, between 4.5 days and 8 days, between 4.5 days and 7 days, between 4.5 days and 6 days, between 4.5 days and 5 days, between 5 days and 10 days, between 5 days and 9 days, between 5 days and 8 days, between 5 days and 7 days, between 5 days and 6 days, between 5.5 days and 10 days, between 5.5 days and 9 days, between 5.5 days and 8 days, between 5.5 days and 7 days, between 5.5 days and 6 days, between 6 days and 10 days, between 7 days and 10 days, between 8 days and 10 days, between 9 days and 10 days.

Follistatin (FS) was first isolated from follicular fluid, as a protein factor capable of suppressing pituitary cell follicle stimulating hormone (FSH) secretion. FS exerts its influence over FSH at least in part through the binding and neutralization of activin.

There are at least two isoforms of FS: FS288 and FS315, created through alternative splicing at the C-terminus. The 288-amino acid isoform has a distinctive structure comprised of a 63 amino acid N-terminal region containing hydrophobic residues important for activin binding, with the major portion of the protein (residues 64-288) comprising three 10-cysteine FS domains of approximately 73-75 amino acids each. These 10-cysteine domains, from N-terminus to C-terminus, are referred to as domain 1, domain 2 and domain 3, respectively. The FS315 isoform is created through an acidic extension of the C-terminus encoded by an extra exon. FS288 tends to be tissue-bound due to the presence of a heparin binding domain, while FS315 tends to be a circulating form, potentially because the heparin binding domain is masked by the extended C-terminus.

It has been shown that FS inhibits both myostatin and activin in vitro and that this inhibition can lead to hypertrophy in vivo in mice (Lee et al., *Regulation of Muscle Mass by Follistatin and Activins*, (2010), MOL. ENDOCRINOL., 24(10): 1998-2008; Gilson et al., *Follistatin Induces Muscle Hypertrophy Through Satellite Cell Proliferation and Inhibition of Both Myostatin and Activin*, (2009), J. PHYSIOL. ENDOCRINOL., 297(1):E157-E164). Without wishing to be held to a particular theory, this observed effect may be at least partially due to FS preventing activation of the Smad2/3 pathway by myostatin and activin. Activation of the Smad2/3 pathway has been shown to result in negative regulation of muscle growth (Zhu et al., *Follistatin Improves Skeletal Muscle Healing After Injury and Disease Through an Interaction with Muscle Regeneration, Angiogenesis, and Fibrosis*, (2011), MUSCULOSKELETAL PATHOLOGY, 179(2):915-930).

The amino acid sequences of a typical wild-type or naturally-occurring human FS315 and FS288 protein are shown in Table 2.

TABLE 2

Exemplary Human Follistatin Isoforms

| | |
|---|---|
| FS315 | GNCWLRQAKNGRCQVLYKTELSKEECCSTGRLSTSWTEEDVNDNTLFKWMIFNG GAPNCIPCKETCENVDCGPGKKCRMNKKNKPRCVCAPDCSNITWKGPVCGLDGK TYRNECALLKARCKEQPELEVQYQGRCKKTCRDVFCPGSSTCVVDQTNNAYCVT CNRICPEPASSEQYLCGNDGVTYSSACHLRKATCLLGRSIGLAYEGKCIKAKSC EDIQCTGGKKCLWDFKVGRGRCSLCDELCPDSKSDEPVCASDNATYASECAMKE AACSSGVLLEVKHSGSCNSISEDTEEEEEDEDQDYSFPISSILEW (SEQ ID NO: 1) |
| FS288 | GNCWLRQAKNGRCQVLYKTELSKEECCSTGRLSTSWTEEDVNDNTLFKWMIFNG GAPNCIPCKETCENVDCGPGKKCRMNKKNKPRCVCAPDCSNITWKGPVCGLDGK |

TABLE 2-continued

Exemplary Human Follistatin Isoforms

TYRNECALLKARCKEQPELEVQYQGRCKKTCRDVFCPGSSTCVVDQTNNAYCVT
CNRICPEPASSEQYLCGNDGVTYSSACHLRKATCLLGRSIGLAYEGKCIKAKSC
EDIQCTGGKKCLWDFKVGRGRCSLCDELCPDSKSDEPVCASDNATYASECAMKE
AACSSGVLLEVKHSGSCN (SEQ ID NO: 12)

Thus, in some embodiments, a recombinant follistatin protein suitable for the present invention is human FS315 (SEQ ID NO:1). As disclosed herein, SEQ ID NO:1 represents the canonical amino acid sequence for the human follistatin protein. In some embodiments, a follistatin protein may be a splice isoform such as FS 288 (SEQ ID NO:12). In some embodiments, a suitable recombinant follistatin protein may be a homologue or an analogue of a wild-type or naturally-occurring protein. For example, a homologue or an analogue of human wild-type or naturally-occurring follistatin protein may contain one or more amino acid or domain substitutions, deletions, and/or insertions as compared to a wild-type or naturally-occurring follistatin protein (e.g., SEQ ID NO: 1), while retaining substantial follistatin protein activity. Thus, in some embodiments, a recombinant follistatin protein suitable for the present invention is substantially homologous to human FS315 follistatin protein (SEQ ID NO: 1). In some embodiments, a recombinant follistatin protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a recombinant follistatin protein suitable for the present invention is substantially identical to human FS315 follistatin protein (SEQ ID NO: 1). In some embodiments, a recombinant follistatin protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1.

Homologues or analogues of human follistatin proteins can be prepared according to methods for altering polypeptide sequence known to one of ordinary skill in the art such as are found in references that compile such methods. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution. In some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. In some embodiments, a "conservative amino acid substitution" refers to an amino acid substitution that does not alter the relative charge or size characteristics of the protein in which the amino acid substitution is made.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology.

In some embodiments, a recombinant follistatin protein suitable for the present invention contains one or more amino acid deletions, insertions or replacement as compared to a wild-type human follistatin protein. For example, a suitable recombinant follistatin protein may contain amino acid substitutions at positions corresponding to Y185 and/or L191, of SEQ ID NO:1.

Domain Deletion Variants

In some embodiments, a recombinant follistatin protein suitable for the present invention contains one or more domain deletions, insertions or replacement (e.g., domain swapping) as compared to a wild-type human follistatin protein. For example, a recombinant follistatin protein suitable for the present invention may contain a deletion, insertion and/or replacement of amino acid sequences corresponding to domain 1, 2 and/or 3. In certain embodiments, a recombinant follistatin protein comprises a deletion of amino acids residues 212-288 of SEQ ID NO:1 (which corresponds to domain 3), as shown below:

```
                                            (SEQ ID NO: 2)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCISISEDTEEEEEDEDQDYSFPISSILEW.
```

It is contemplated that a suitable recombinant follistatin protein may be a homologue or an analogue of a suitable domain deletion variant, containing one or more amino acid substitutions, deletions, and/or insertions as compared to the suitable follistatin domain deletion variant (e.g., SEQ ID NO:2), while retaining substantial follistatin protein activity. Thus, in some embodiments, a recombinant follistatin protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to SEQ ID NO:2.

Follistatin Fusion Proteins

It is contemplated that a suitable recombinant follistatin protein can be in a fusion protein configuration. For example, a recombinant follistatin protein suitable for the present invention may be a fusion protein between a follistatin domain and another domain or moiety that typically can facilitate a therapeutic effect of follistatin by, for example, enhancing or increasing stability, potency and/or delivery of follistatin protein, or reducing or eliminating immunogenicity, clearance, or toxicity. Such suitable domains or moieties for a follistatin fusion protein include but are not limited to Fc domain, XTEN domain.

Fc Domain

In some embodiments, a suitable recombinant follistatin protein contains an Fc domain or a portion thereof that binds to the FcRn receptor. As a non-limiting example, a suitable Fc domain may be derived from an immunoglobulin subclass such as IgG. In some embodiments, a suitable Fc domain is derived from IgG1, IgG2, IgG3, or IgG4. In some embodiments, a suitable Fc domain is derived from IgM, IgA, IgD, or IgE. Particularly suitable Fc domains include those derived from human or humanized antibodies. In some embodiments, a suitable Fc domain is a modified Fc portion, such as a modified human Fc portion.

In some embodiments, a suitable Fc domain comprises an amino acid sequence shown below

```
                                         (SEQ ID NO: 3)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK,
or
                                         (SEQ ID NO: 4)
KTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGN

VFSCSVMHEALHNHYTQKSLSLSPGK;
or
                                         (SEQ ID NO: 14)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

In some embodiments, a suitable Fc domain comprises an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to SEQ ID NO: 3, SEQ ID NO: 4, or SEQ ID NO: 14.

It is contemplated that improved binding between Fc domain and the FcRn receptor results in prolonged serum half-life. Thus, in some embodiments, a suitable Fc domain comprises one or more amino acid mutations that lead to improved binding to FcRn. Various mutations within the Fc domain that effect improved binding to FcRn are known in the art and can be adapted to practice the present invention. In some embodiments, a suitable Fc domain comprises one or more mutations at one or more positions corresponding to Thr 250, Met 252, Ser 254, Thr 256, Thr 307, Glu 380, Met 428, His 433 and/or Asn 434 of human IgG1.

For example, a suitable Fc domain may contain mutations of H433K (His433Lys) and/or N434F (Asn434Phe). As a non-limiting example, a suitable Fc domain may contain mutations H433K (His433Lys) and N434F (Asn434Phe). An exemplary Fc domain sequence incorporating the mutations is shown below:

```
                                         (SEQ ID NO: 15)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALKFHYTQKSLSLSPGK.
```

Additional amino acid substitutions that can be included in a Fc domain include those described in, e.g., U.S. Pat. Nos. 6,277,375; 8,012,476; and 8,163,881, which are incorporated herein by reference.

Linker or Spacer

A follistatin domain may be directly or indirectly linked to an Fc domain. In some embodiments, a suitable recombinant follistatin protein contains a linker or spacer that joins a follistatin domain and an Fc domain. An amino acid linker or spacer is generally designed to be flexible or to interpose a structure, such as an alpha-helix, between the two protein moieties. A linker or spacer can be relatively short, or can be longer. Typically, a linker or spacer contains for example 3-100 (e.g., 5-100, 10-100, 20-100 30-100, 40-100, 50-100, 60-100, 70-100, 80-100, 90-100, 5-55, 10-50, 10-45, 10-40, 10-35, 10-30, 10-25, 10-20) amino acids in length. In some embodiments, a linker or spacer is equal to or longer than 2, 3, 4, 5, 6, 7, 8, 9, 10, 15, 20, 25, 30, 35, 40, 45, 50, 55, 60, 65, 70, 75, 80, 85, 90, 95, or 100 amino acids in length. Typically, a longer linker may decrease steric hindrance. In some embodiments, a linker will comprise a mixture of glycine and serine residues. In some embodiments, the linker may additionally comprise threonine, proline and/or alanine residues. Thus, in some embodiments, the linker comprises between 10-100, 10-90, 10-80, 10-70, 10-60, 10-50, 10-40, 10-30, 10-20, 10-15 amino acids. In some embodiments, the linker comprises at least 10, 15, 20, 25, 30, 35, 40, 45, 50, 55, 60, 65, 70, 75, 80, 85, 90, or 95 amino acids. In some embodiments, the linker is not a linker consisting of ALEVLFQGP (SEQ ID NO: 18).

As non-limiting examples, linkers or spacers suitable for the present invention include but are not limited to:

```
                                  (GAG linker, SEQ ID NO: 5)
GAPGGGGGAAAAAGGGGGGAP;

(GAG2 linker, SEQ ID NO: 6)
GAPGGGGGAAAAAGGGGGGAPGGGGGAAAAAGGGGGGAP;
and (GAG3 linker, SEQ ID NO: 7)
GAPGGGGGAAAAAGGGGGGAPGGGGGAAAAAGGGGGGAPGGGGGAAAAAG

GGGGGAP.
```

Suitable linkers or spacers also include those having an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to the above exemplary linkers, e.g., GAG linker (SEQ ID NO:5), GAG2 linker (SEQ ID NO:6), or GAG3 linker (SEQ ID NO:7). Additional linkers suitable for use with some embodiments may be found in US20120232021, filed on Mar. 2, 2012, the disclosure of which is hereby incorporated by reference in its entirety, In some embodiments, a linker is provided that associates the follistatin polypeptide with the Fc domain without substantially affecting the ability of the follistatin polypeptide to bind to any of its cognate ligands (e.g., activin, myostatin, heparin, etc.). In some embodiments, a linker is provided such that the binding of a follistatin peptide to heparin is not altered as compared to the follistatin polypeptide alone. For example, in some embodiments, a follistatin polypeptide is a FS315 polypeptide, which normally does not bind heparin unless it is associated with activin. In some such embodiments, a linker is provided that does not result in increased heparin binding of the FS315 polypeptide as compared to the FS315 polypeptide alone.

Exemplary Follistatin Fusion Proteins

In particular embodiments, a suitable recombinant follistatin fusion protein includes a follistatin polypeptide, an Fc domain, and a linker that associates the follistatin polypeptide with the Fc domain, wherein the follistatin polypeptide comprises an amino acid sequence at least 50%, 55%, 60%, 65%, 70%, 75%, 80%, 85%, 90%, 91%, 92%, 93%, 94%, 95%, 96%, 97%, 98%, 99% or 100% identical to the wild-type human FS315 protein (SEQ ID NO: 1) or a domain 3 deleted FS315 protein (SEQ ID NO:2). Typically, a suitable recombinant follistatin fusion protein is capable of binding to activin and myostatin. In some embodiments, a suitable recombinant follistatin fusion protein has an in vivo half-life ranging from about 0.5-6 days (e.g., about 0.5-5.5 days, about 0.5-5 days, about 1-5 days, about 1.5-5 days, about 1.5-4.5 days, about 1.5-4.0 days, about 1.5-3.5 days, about 1.5-3 days, about 1.5-2.5 days, about 2-6 days, about 2-5.5 days, about 2-5 days, about 2-4.5 days, about 2-4 days, about 2-3.5 days, about 2-3 days). In some embodiments, a suitable recombinant follistatin fusion protein has an in vivo half-life ranging from about 2-10 days (e.g., ranging from about 2.5-10 days, from about 3-10 days, from about 3.5-10 days, from about 4-10 days, from about 4.5-10 days, from about 5-10 days, from about 3-8 days, from about 3.5-8 days, from about 4-8 days, from about 4.5-8 days, from about 5-8 days, from about 3-6 days, from about 3.5-6 days, from about 4-6 days, from about 4.5-6 days, from about 5-6 days).

As non-limiting examples, suitable follistatin Fc fusion proteins may have an amino acid sequence shown below:

(SEQ ID NO: 9)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWGAPGGGGAAAAGGGGGAPGGGGAAAAGGGG

GGAPGGGGAAAAGGGGGAPEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPGK,
or (SEQ ID NO: 9)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWGAPGGGGAAAAGGGGGAPGGGGAAAAGGGG

GGAPGGGGAAAAGGGGGAPEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPGK.

As other non-limiting examples, suitable follistatin Fc fusion proteins may have an amino acid sequence shown below:

(SEQ ID NO: 11)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCISISEDTEEEEEDEDQDYSFPISSILEWGAPGGGGAAAA

GGGGGGAPGGGGAAAAGGGGGAPGGGGAAAAGGGGGAPEPKSC

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK,
or (SEQ ID NO: 11)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCISISEDTEEEEEDEDQDYSFPISSILEWGAPGGGGAAAA

GGGGGGAPGGGGAAAAGGGGGAPGGGGAAAAGGGGGAPEPKSC

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

-continued

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

As yet other non-limiting examples, suitable follistatin Fc fusion proteins may have an amino acid sequence shown below:

(SEQ ID NO: 16)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWGAPGGGGGAAAAAGGGGGGAPGGGGGAAAAAGGGG

GGAPGGGGGAAAAAGGGGGGAPDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK
Or (SEQ ID NO: 17)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWGAPGGGGGAAAAAGGGGGGAPGGGGGAAAAAGGGG

GGAPGGGGGAAAAAGGGGGGAPDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALKFHYTQKSLSLSPGK

In some embodiments, a suitable recombinant follistatin Fc fusion protein has an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to SEQ ID NO:8, 9, 10, 11, 16 or 17.

It is contemplated that a follistatin-Fc fusion protein may be provided in various configurations including homodimeric or monomeric configurations. For example, a suitable homodimeric configuration may be designed to have the C-terminal end of fusion partner (e.g., a follistatin polypeptide plus linker) attached to the N-terminal end of both Fc polypeptide strands. A suitable monomeric configuration may be designed to have the C-terminal end of fusion partner (e.g., a follistatin polypeptide plus linker) fused to one Fc dimer. A monomeric configuration may decrease steric hindrance.

As used herein, "percent (%) amino acid sequence identity" with respect to a reference protein sequence (e.g., a reference follistatin protein sequence) identified herein is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

Production of Recombinant Follistatin Proteins

A recombinant follistatin protein suitable for the present invention may be produced by any available means. For example, a recombinant follistatin protein may be recombinantly produced by utilizing a host cell system engineered to express a recombinant follistatin protein-encoding nucleic acid. Alternatively or additionally, a recombinant follistatin protein may be produced by activating endogenous genes. Alternatively or additionally, a recombinant follistatin protein may be partially or fully prepared by chemical synthesis.

Where proteins are recombinantly produced, any expression system can be used. To give but a few examples, known expression systems include, for example, *E. coli*, egg, baculovirus, plant, yeast, or mammalian cells.

In some embodiments, recombinant follistatin proteins suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59, 1977); human fibrosarcoma cell line (e.g., HT1080); baby hamster kidney cells (BHK21, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, the present invention provides recombinant follistatin proteins produced from human cells. In some embodiments, the present invention provides recombinant follistatin proteins produced from CHO cells or HT1080 cells.

Typically, cells that are engineered to express a recombinant follistatin protein may comprise a transgene that encodes a recombinant follistatin protein described herein. It should be appreciated that the nucleic acids encoding recombinant follistatin protein may contain regulatory sequences, gene control sequences, promoters, non-coding sequences and/or other appropriate sequences for expressing the recombinant follistatin protein. Typically, the coding region is operably linked with one or more of these nucleic acid components.

The coding region of a transgene may include one or more silent mutations to optimize codon usage for a particular cell type. For example, the codons of a follistatin transgene may be optimized for expression in a vertebrate cell. In some embodiments, the codons of a follistatin transgene may be optimized for expression in a mammalian cell. In some embodiments, the codons of a follistatin transgene may be optimized for expression in a human cell.

Pharmaceutical Composition and Administration

The present invention further provides a pharmaceutical composition containing a recombinant follistatin protein described herein and a physiologically acceptable carrier or excipient.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used.

A suitable pharmaceutical composition or medicament, if desired, can also contain minor amounts of wetting or emulsifying agents, or pH buffering agents. A composition can be a liquid solution, suspension, emulsion, tablet, pill, capsule, sustained release formulation, or powder. A composition can also be formulated as a suppository, with traditional binders and carriers such as triglycerides. Oral formulations can include standard carriers such as pharmaceutical grades of mannitol, lactose, starch, magnesium stearate, polyvinyl pyrrolidone, sodium saccharine, cellulose, magnesium carbonate, etc.

A pharmaceutical composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

A recombinant follistatin protein described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Routes of Administration

A recombinant follistatin protein described herein (or a composition or medicament containing a recombinant follistatin protein described herein) is administered by any appropriate route. In some embodiments, a recombinant follistatin protein or a pharmaceutical composition containing the same is administered systemically. Systemic administration may be intravenous, intradermal, inhalation, transdermal (topical), intraocular, intramuscular, subcutaneous, intramuscular, oral and/or transmucosal administration. In some embodiments, a recombinant follistatin protein or a pharmaceutical composition containing the same is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. In some embodiments, a recombinant follistatin protein or a pharmaceutical composition containing the same is administered intravenously. In some embodiments, a recombinant follistatin protein or a pharmaceutical composition containing the same is administered orally. More than one route can be used concurrently, if desired.

In some embodiments, administration results only in a localized effect in an individual, while in other embodiments, administration results in effects throughout multiple portions of an individual, for example, systemic effects. Typically, administration results in delivery of a recombinant follistatin protein to one or more target tissues. In some embodiments, the recombinant follistatin protein is delivered to one or more target tissues including, but not limited to, heart, brain, spinal cord, striated muscle (e.g., skeletal muscle), smooth muscle, kidney, liver, lung, and/or spleen. In some embodiments, the recombinant follistatin protein is delivered to the heart. In some embodiments, the recombinant follistatin protein is delivered to striated muscle, in particular, skeletal muscle. In some embodiments, the recombinant follistatin protein is delivered to triceps, tibialis anterior, soleus, gastrocnemius, biceps, trapezius, deltoids, quadriceps, and/or diaphragm.

Dosage Forms and Dosing Regimen

In some embodiments, a composition is administered in a therapeutically effective amount and/or according to a dosing regimen that is correlated with a particular desired outcome (e.g., with treating or reducing risk for a muscular dystrophy, such as Duchenne muscular dystrophy).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, a recombinant follistatin protein is administered at a therapeutically effective amount. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of a muscular dystrophy, such as Duchenne muscular dystrophy.

In some embodiments, a formulation comprising a recombinant follistatin protein described herein administered as a single dose. In some embodiments, a formulation comprising a recombinant follistatin protein described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising a recombinant follistatin protein described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising a recombinant follistatin protein described herein is administered at regular intervals indefinitely. In some embodiments, a formulation comprising a recombinant follistatin protein described herein is administered at regular intervals for a defined period.

Combination Therapy

In some embodiments, a recombinant follistatin protein is administered in combination with one or more known therapeutic agents (e.g., corticosteroids) currently used for treatment of a muscular dystrophy. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

EXAMPLES

Example 1. Follistatin Targets Myostatin and Activin Specifically

This example illustrates Follistatin binding to target and non-target ligands to evaluate safety of Follistatin as a protein therapeutic for treating DMD. Without wishing to be bound by theory, it is contemplated that activation of Smad2/3 pathway by myostatin and activin leads to inhibition of myogenic protein expression. As a result, myoblasts can't differentiate into muscle. Therefore, myostatin and activin are considered viable targets for muscle regeneration. However, many myostatin and activin antagonists such as soluble activin receptor type IIB (sActRIIB) also bind bone morphogenetic proteins (BMPs) due to certain structural similarities. BMPs, especially, BMP-9 and BMP-10, are considered pivotal morphogenetic signals, orchestrating tissue architecture throughout the body. Inhibition of such BMPs may lead to undesired pathological conditions. As described in detail below, the experimental data described in this example confirm that Follistatin specifically targets myostatin and activin with high affinity and does not bind to non-target BMPs with meaningful affinity. Thus this example demonstrates that Follistatin can be a safe protein therapeutic with fewer undesired off-target effects as compared to other myostatin modulators such as sActRIIB.

Specifically, commercially available follistatins (FS315, manufactured by R&D Systems and follistatin-Fc human chimera FS315-hFc, manufactured by Sino Biological), and FS315-GAG3-mFc fusion proteins were used to assess binding affinity and kinetics to activin, myostatin, and BMPs using Biacore assays. Briefly, FS315 was immobilized onto a CM5 chip, and follistatin-Fc fusion proteins were captured using human or mouse antibody capture kits (GE Healthcare). Post amine-coupling, a concentration series of activin, myostatin, or BMPs (e.g., BMP-2, -4, -6, -7, -9, -10, and GDF-11) was added as soluble analyte at 25° C. sActRIIB-hFc was used as a control. Binding affinities (Kd) and kinetics were determined using standard methods. Exemplary results are shown in Table 3.

TABLE 3

Exemplary Binding Affinity and Kinetics Data

| | KD values (M) | | | |
|---|---|---|---|---|
| Ligand | FS315 | FS315-hFc | FS315-mFc | sActRIIB-hFc |
| BMP-2 | 4.4E−07 | no binding | no binding | no binding |
| BMP-4 | 1.4E−08 | NM | 8.1E−08 | 1.3E−07 |
| BMP-6 | 3.6E−10 | 9.0E−10 | NM | 5.7E−11 |

TABLE 3-continued

Exemplary Binding Affinity and Kinetics Data

| Ligand | KD values (M) | | | |
|---|---|---|---|---|
| | FS315 | FS315-hFc | FS315-mFc | sActRIIB-hFc |
| BMP-7 | 3.8E-08 | NM | NM | 1.1E-09 |
| BMP-9 | no binding | no binding | no binding | 5.4E-11 |
| BMP-10 | 1.0E-07 | 1.5E-07 | no binding | 1.0E-11 |
| GDF-11 | N/A | 8.2E-10 | 1.8E-14 | 3.4E-10 |
| myostatin | 1.0E-13 | 8.4E-14 | 7.3E-14 | 1.3E-12 |
| activin | 7.3E-10 | 1.9E-10 | 3.8E-14 | 7.0E-11 |

NM = not measurable due to poor curve fit or high binding to reference chip

As shown in Table 3, follistatin (e.g., FS315 or FS315-Fc) binds targets myostatin and activin with high affinity but does not bind BMP-9 and -10 (Kd not measurable or greater than $10^{-7}$ M), while sActRIIB-Fc binds to myostatin, activin and BMPs with similar affinity. Surprisingly and importantly, the Fc fusion increases affinity of follistatin to primary target myostatin by at least 10-fold.

In addition, luciferase reporter assays were used to further determine if follistatin specifically inhibits myostatin and activin signaling (Smad 2/3 pathway) but not BMP signaling (Smad 1/5/8 pathway). Specifically, a BMP Response Element (BRE)-luciferase assay was used to determine if follistatin can inhibit Smad 1/5/8 pathway by measuring reduction of luciferase signal (Korchynskyi et al., *Identification and Functional Characterization of Distinct Critically Important Bone Morphogenetic Protein-specific Response Elements in the Id1 Promoter*, (2002), J BIOL CHEM., 277(7):4883-4891). A CAGA-luciferase assay was used to determine if follistatin can inhibit Smad 2/3 pathway by measuring reduction of luciferase signal (Dennler et al., *Direct binding of Smad3 and Smad4 to critical TGFβ-inducible elements in the promoter of human plasminogen activator inhibitor-type 1 gene*, (1998), EMBO J, 17(11): 3091-3100). Briefly, HEK293 cells were co-transfected with either the BRE (BRE-Id1-luc) or CAGA-luciferase (p(CAGA)$_{12}$-MLP-luc vector) constructs and renilla-luciferase construct (Promega pGL4.74 [hRluc/TK]) overnight. The following day, cells were treated with myostatin and activin (for Smad 2/3 pathway induction, CAGA-luciferase reporter), or BMP-9 and BMP-10 (for Smad 1/5/8 pathway induction, BRE-luciferase reporter) with or without a concentration series of follistatin. After an overnight incubation, the luciferase signal was determined using the Promega Dual-Glo Assay kit, with values normalized to renilla control. In this experiment, native follistatin (R&D Systems) and follistatin Fc fusion proteins (Sino Biological FS315-hFc, FS315-GAG3-mFc) were tested. FS315-GAG3-mFc is shown below.

(SEQ ID NO: 13)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEWGAPGGGGGAAAAAGGGGGAPGGGGGAAAAAGGGG

GGAPGGGGGAAAAAGGGGGGAPGCKPCICTVPEVSSVFIFPPKPKDVLTI

TLTPKVTCVVVDISKDDPEVQFSWFVDDVEVHTAQTQPREEQFNSTFRSV

SELPIMHQDWLNGKEFKCRVNSAAFPAPIEKTISKTKGRPKAPQVYTIPP

PKEQMAKDKVSLTCMITDFFPEDITVEWQWNGQPAENYKNTQPIMDTDGS

YFVYSKLNVQKSNWEAGNTFTCSVLHEGLHNHHTEKSLSHSPGK

Exemplary results of the BRE-luciferase assay are shown in FIG. 1. FS315-Fc does not inhibit BMP-9 or -10 signaling through the Smad 1/5/8 pathway.

Figure 2:
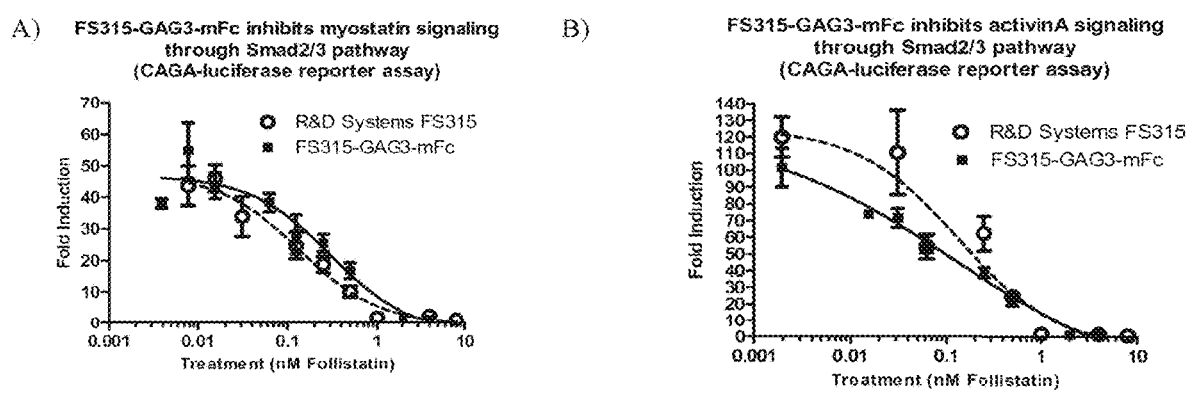
FIG. 2 shows exemplary results illustrating that FS315-Fc inhibits myostatin- and activin-mediated Smad 2/3 signaling.

Exemplary results of the CAGA-luciferase assay are shown in FIG. 2. Both FS315 and FS315-GAG3-mFc showed potent inhibition of Smad2/3 signaling at doses of 0.1 nM and above as compared to the amount of Smad 2/3 induction observed after administration of physiologically relevant levels of myostatin (1.2 nM) and activin (0.4 nM), known activators of Smad 2/3. These results indicate that follistatin is a potent and specific inhibitor of myostatin and activin activity. The presence of the Fc fusion did not detrimentally affect the potency of follistatin, as indicated by the similar inhibitory curves between the native FS315 molecule and the FS315-GAG3-mFc fusion protein. Unexpectedly and importantly, the Fc fusion protein according to the present invention significantly increases the binding affinity of follistatin to primary target myostatin (e.g., by at least 10 fold as shown in Table 3).

Example 2. Follistatin Fusion Protein FS315-GAG3-mFc has Extended Serum Half-Life Prior to our invention, it was reported that follistatin has a short serum half-life, which is a concern for developing follistatin as a protein therapeutic. For example, typical commercial FS315 protein has a serum half-life of about an hour. In this Example, the in vivo half-life of FS315-GAG3-mFc fusion protein was determined and it has a significantly extended serum half-life.

Figure 3:
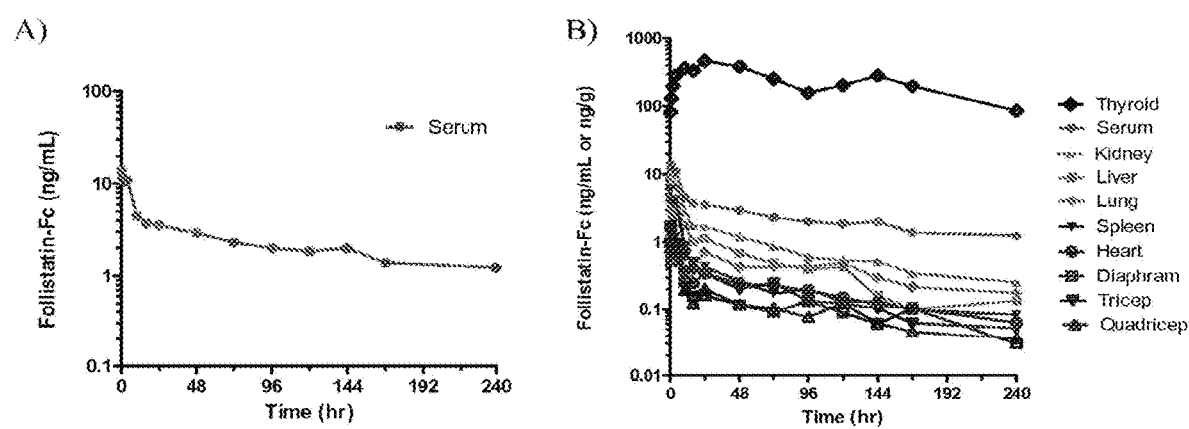
FIG. 3 shows exemplary results illustrating PK profile across tissues. An exemplary follistatin-Fc protein has a serum half-life of ~5 days in mouse serum (FIG. 3A) and a tissue half-life of 2-5 days (FIG. 3B).

Specifically, an imprinting control region (ICR) mouse was selected as a model and $I^{125}$-labeled FS315-GAG3-mFc was administered subcutaneously at 1.0 mg/kg (~2 µCi/animal). After administration, samples of serum and tissues were taken up to 10 days post-injection. The tissues sampled were: thyroid, liver, kidney, lung, spleen, diaphragm, heart, quadriceps and triceps. Exemplary results of the serum samples are shown in FIG. 3A. As can be seen, the serum half-life of FS315-GAG3-mFc is approximately 5 days, which is surprisingly long as compared to the short follistatin serum half-life (about 1 hour) known in the art. Exemplary results of the PK profile across various tissues are shown in FIG. 3B and Table 4. The half-life of Follistatin-Fc, with the exception of the thyroid, is between two and five days across tissues. Again, the extended tissue half-life profile is unexpected.

The extended in vivo half-life data further confirm that follistatin can be an effective protein therapeutic for treatment of DMD.

TABLE 4

Exemplary FS315-GAG3-mFc In Vivo PK Data

| Tissue | $t_{1/2}$ (h) | Cmax (ng/g tissue or ng/mL serum) | $AUC_{0-last}$ (hr/ng/g tissue or ng/mL serum) | $AUC_{0-\infty}$ (hr/ng/g tissue or ng/mL serum) |
|---|---|---|---|---|
| Serum | 134 | 14.0 | 557 | 782 |
| Thyroid | 118 | 467.4 | 57019 | 71769 |
| Kidney | 77 | 9.8 | 221 | 249 |
| Liver | 48 | 4.4 | 118 | 127 |
| Lung | 116 | 3.9 | 106 | 136 |
| Spleen | 95 | 5.8 | 72 | 83 |
| Heart | 105 | 1.6 | 46 | 55 |
| Diaphragm | 99 | 1.0 | 28 | 33 |
| Triceps | 78 | 1.7 | 44 | 50 |
| Quadriceps | 99 | 0.8 | 25 | 31 |

Example 3. In Vivo Efficacy of FS315-GAG3-mFc

This Example demonstrates that administration of follistatin (e.g., FS315-GAG3-mFc) to mdx mouse model of Duchenne muscular dystrophy results in a trend of increased muscle mass even at a low dose of 1 mg/kg. In this example, the terms "FS315-GAG3-mFc", "FS315-Fc" and "FS315-mFc" used interchangeably.

Specifically, in this study, 45 mdx mice were treated with empty vehicle, 0 mg/kg, 1.0 mg/kg or 8 mg/kg FS315-GAG3-mFc. Animals in the vehicle or treatment groups received two subcutaneous (interscapular) injections per week for the duration of the study and follistatin fusion protein levels were assessed through retro-orbital sampling.

Half of the vehicle treated control animals were sacrificed with the 1 mg/kg FS315-Fc group, and the remaining vehicle treated animals along with the untreated control animals, were sacrificed with the 8 mg/kg treatment group. Exemplary treatment schedule was as shown in Table 5A and B:

TABLE 5

Exemplary injection and sampling schedule in mdx Mice

| Event | Day |
|---|---|
| 5A: 1 mg/kg FS315-GAG3-mFc treatment course | |
| Pre-bleed, Injection 1 | 0 |
| Injection 2 | 3 |
| Blood sample taken, Injection 3 | 7 |
| Injection 4 | 10 |
| Blood sample taken, Injection 5 | 14 |
| Injection 6 | 17 |
| Blood sample taken, Injection 7 | 21 |
| Injection 8 | 24 |
| Blood sample taken, Injection 9 | 29 |
| Sacrifice, week 4 time point | 30 |
| Injection 10 | 32 |
| Blood sample taken, Injection 11 | 35 |
| Injection 12 | 38 |
| Blood sample taken | 44 |
| Injection 13 | 45 |
| Injection 14 | 49 |
| Blood sample taken, Injection 15 | 52 |
| Injection 16 | 56 |
| Blood sample taken, Injection 17 | 59 |
| Injection 18 | 63 |
| Injection 19 | 66 |
| Blood sample taken | 70 |
| Final sacrifice, week 10 | 71 |
| 5B. 8 mg/kg FS315-GAG3-mFc treatment course | |
| Pre-bleed | 0 |
| Injection 1 | 1 |
| Injection 2 | 5 |
| Blood sample taken, Injection 3 | 8 |
| Injection 4 | 12 |
| Blood sample taken, Injection 5 | 15 |
| Injection 6 | 19 |
| Injection 7 | 22 |
| Injection 8 | 26 |
| Blood sample taken, Injection 9 | 30 |
| Injection 10 | 33 |
| Injection 11 | 37 |
| Injection 12 | 41 |
| Blood sample taken | 43 |
| Final sacrifice, week 6 | 44 |

Figure 4:
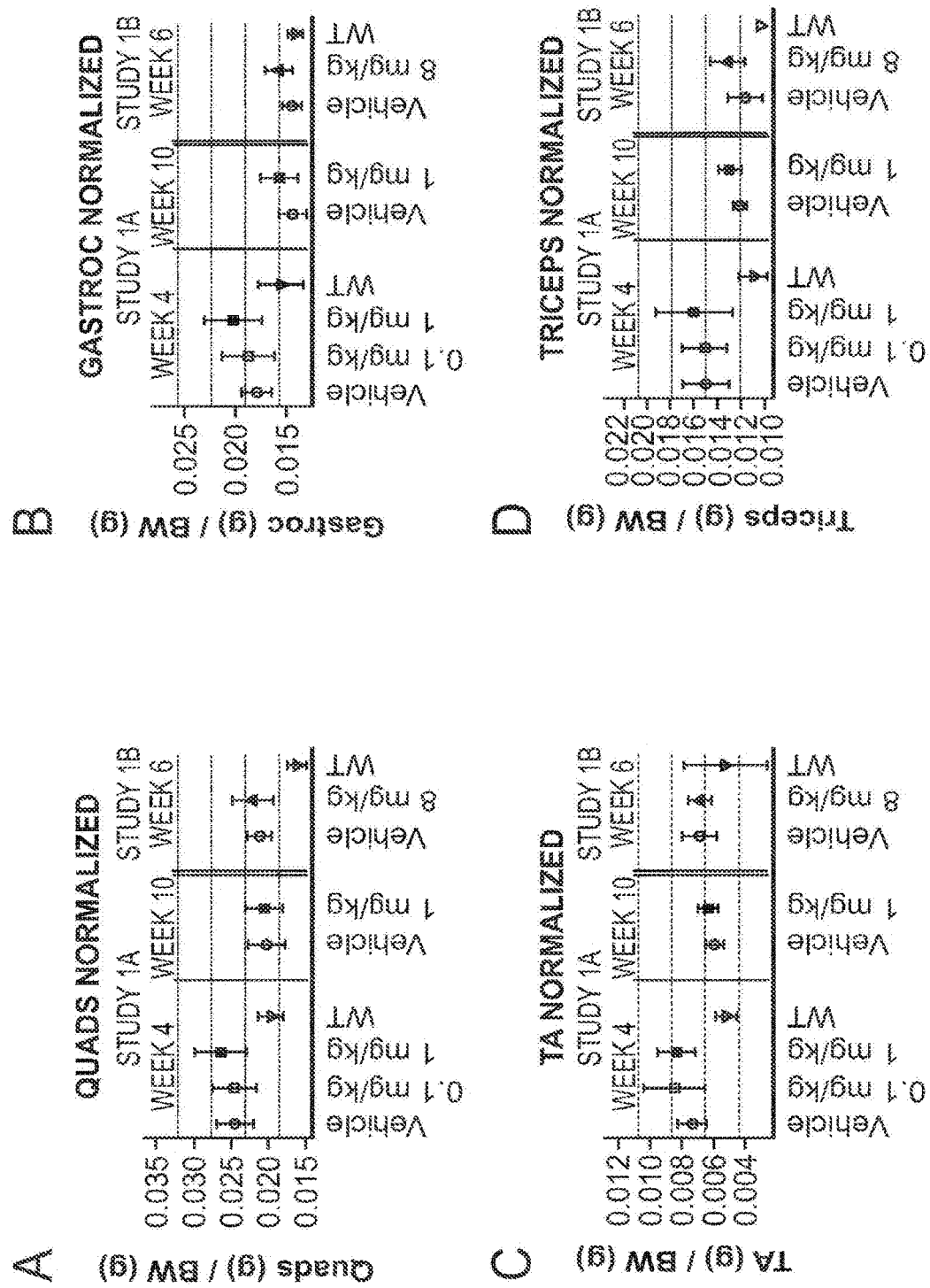
FIG. 4 shows exemplary results illustrating the effect of an exemplary follistatin-Fc protein on muscle weight of quadriceps (FIG. 4A), gastrocnemius (FIG. 4B), tibialis anterior (FIG. 4C), and triceps (FIG. 4D) after 4 and 10 weeks of exposure to 1 mg/kg FS315-mFc and 6 weeks exposure to 8 mg/kg. The muscle weights are corrected to baseline body weight.

Exemplary data regarding muscle weights in the vehicle treated versus 1 mg/kg FS315-Fc group are shown in FIG. 4. Specifically, FIG. 4 shows the muscle weights for the quadriceps (FIG. 4A), gastrocnemius (FIG. 4B), tibialis anterior (FIG. 4C) and triceps (FIG. 4D) in grams after 4 and 10 weeks of treatment with 1 mg/kg, and 6 weeks of treatment with 8 mg/kg. The muscle weight data is adjusted for baseline body weight.

Figure 5:
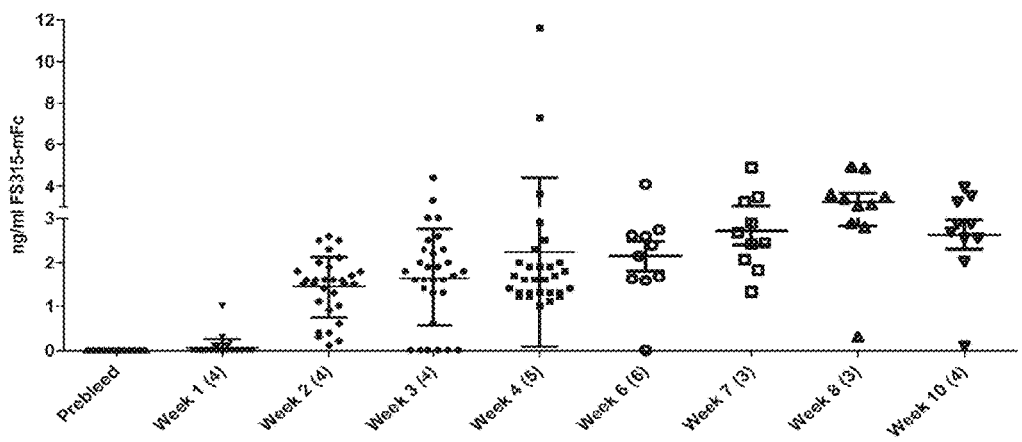
FIG. 5 shows exemplary results illustrating the effect of exemplary follistatin-Fc protein on serum follistatin levels over time.
Figure 5:
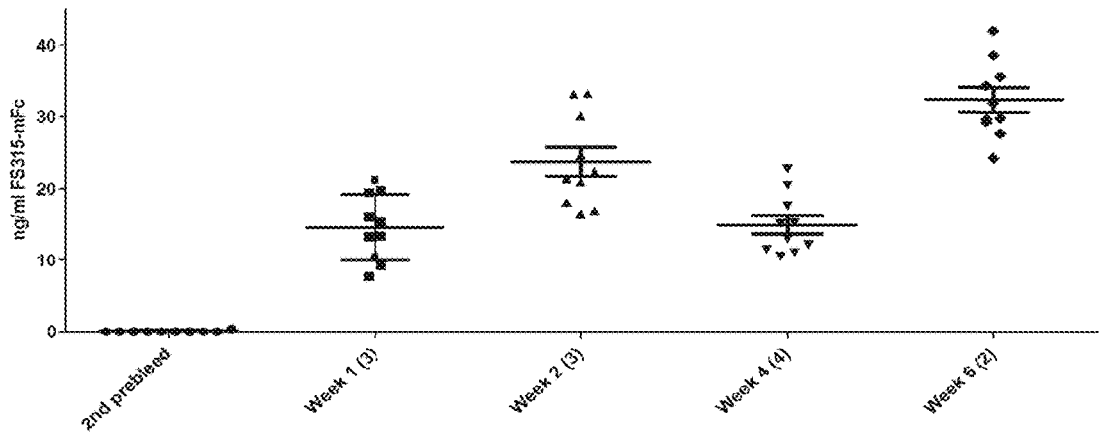

Exemplary data for the circulating levels of follistatin after administration is shown in FIG. 5. Specifically, FIG. 5A shows the levels of FS315-mFc in the serum of animals treated with twice weekly injections of 1 mg/kg, and FIG. 5B shows the levels of FS315-mFc in the serum of animals treated twice weekly with 8 mg/kg.

As is shown in FIGS. 4-5, there is a clear indication that FS315-Fc increases muscle mass in animal models of DMD.

Example 4. In Vivo Efficacy of Recombinantfollistatin-Fc Fusion Protein

This example demonstrates that administration of a follistatin-Fc fusion protein results in muscle hypertrophy (e.g., increased muscle mass and myofiber diameters) in vivo.

In this study, both C57BL/10 and mdx mice were injected with FS315-GAG3-mFc directly into the gastrocnemius muscle (intramuscular, IM). Specifically, each mouse received 2 injections, one on each side, twice weekly. The left gastrocnemius received 20 μL of a 1 mg/mL solution of FS315-GAG3-mFc for a total of 20 μg protein per injection. The right gastrocnemius received 20 μL of PBS (vehicle control). Injections occurred twice weekly for a total of 4 weeks. 24 h after the final injection, mice were sacrificed and the gastrocnemius muscles were carefully dissected and weighed. A group receiving the soluble activin type IIB receptor-Fc mouse chimera (sActRIIB-mFc, R&D Systems) at the same dose was included as a positive control. In addition, untreated mice were included as a negative control.

Figure 6:
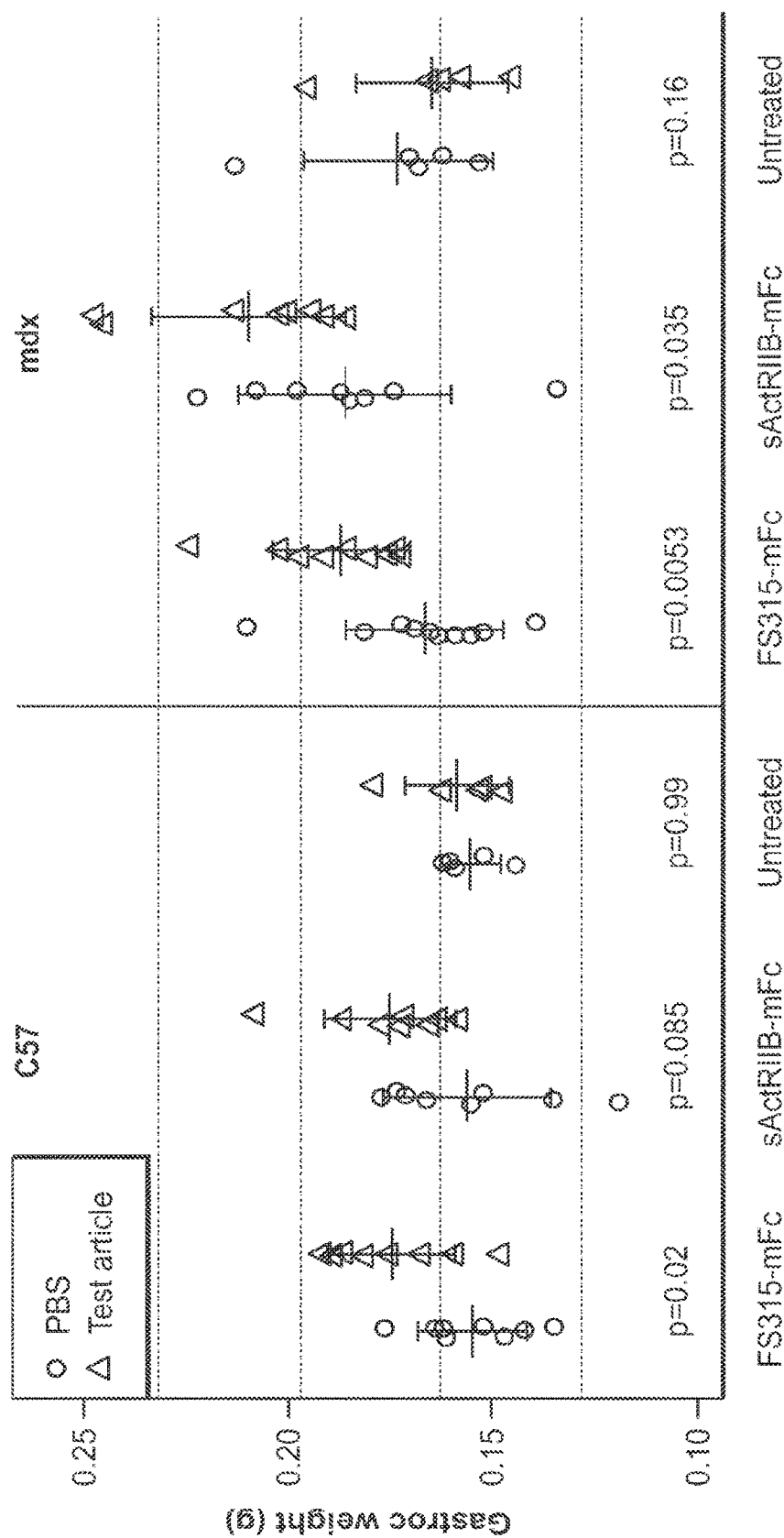
FIG. 6 shows exemplary results illustrating the effect of exemplary follistatin-Fc protein on muscle weight of the gastrocnemius after exposure to FS315-mFc, sActRIIB-mFc, or PBS control.

FIG. 6 shows significantly increased muscle mass in both C57 control mice as well as mdx mice after twice weekly treatment with 20 μg FS315-mFc or sActRIIB-mFc. The study design and numerical data represented in FIG. 6 are shown in Table 6 below:

TABLE 6

Muscle Weight

| Strain | Group | N | Test Gastroc Weight (g) | PBS Gastroc Weight (g) | Test-PBS Gastroc Weight (g) | P-Value** |
|---|---|---|---|---|---|---|
| C57 | FS315-mFc* | 8 | 0.17 ± 0.016 (0.18) | 0.15 ± 0.013 (0.16) | 0.02 ± 0.013 (0.024) | 0.02 |
|  | sActRIIB-mFc | 8 | 0.18 ± 0.016 (0.17) | 0.16 ± 0.02 (0.16) | 0.019 ± 0.017 (0.016) | 0.09 |
|  | Untreated | 5 | 0.16 ± 0.013 (0.15) | 0.16 ± 0.0074 (0.16) | 0.0032 ± 0.012 (0.003) | >0.99 |
| mdx | FS315-mFc | 10 | 0.19 ± 0.017 (0.18) | 0.17 ± 0.019 (0.16) | 0.021 ± 0.013 (0.018) | 0.005 |
|  | sActRIIB-mFc | 8 | 0.21 ± 0.024 (0.2) | 0.19 ± 0.026 (0.19) | 0.024 ± 0.017 (0.018) | 0.04 |
|  | Untreated | 5 | 0.16 ± 0.019 (0.16) | 0.17 ± 0.023 (0.17) | −0.0084 ± 0.0055 (−0.06) | 0.16 |

*All Follistatin constructs used in this example contain a GAG3 linker.
**P-values obtained from paired t-test and are Bonferroni-corrected (correcting for 6 statistical tests)

Myofiber diameters were determined through digital whole slide scanning of the injected gastrocnemius muscle. Samples were fixed in 10% neutral buffered saline, processed and embedded in paraffin, cut into 5 μm sections, and stained with Alexa fluor 488 conjugated Wheat Germ Agglutinin (WGA), a method that stains muscle cell membranes. The scanned images were analyzed using image analysis software (ImageScope and ImagePro Plus). For each myofiber, the average diameter was determined by measuring the myofiber cross section length at 2 degree intervals, passing through the myofiber's centroid.

Figure 15:
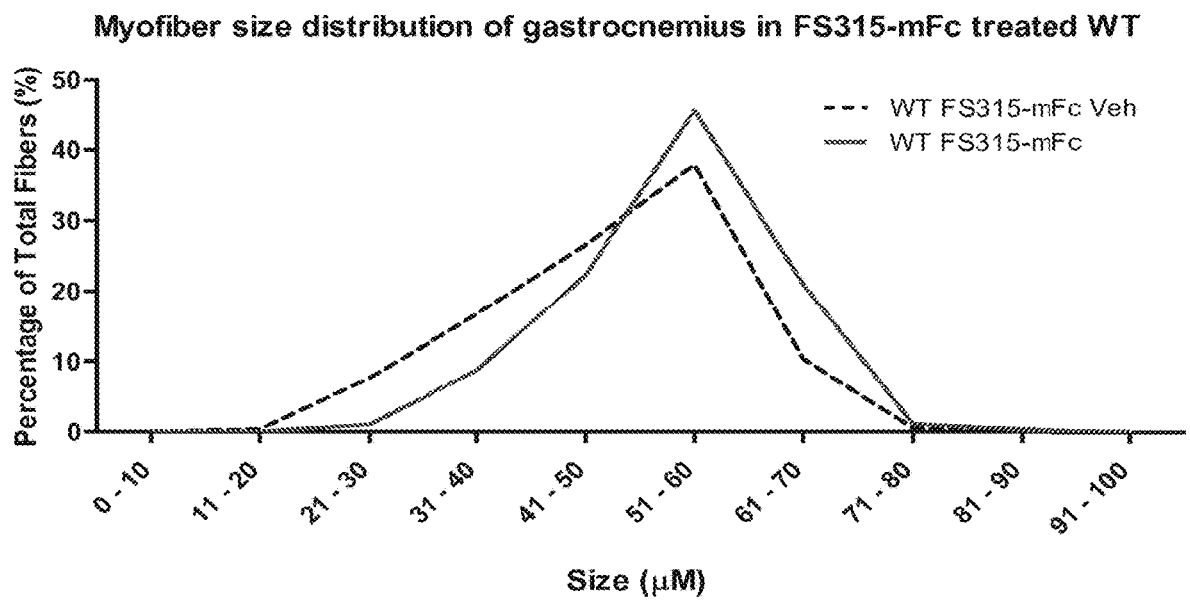
FIG. 15 shows exemplary results demonstrating the effect of an exemplary follistatin-Fc protein on the diameter of myofibers in the gastrocnemius of A) C57 mice and B) mdx mice after 4 weeks of exposure.
Figure 15:
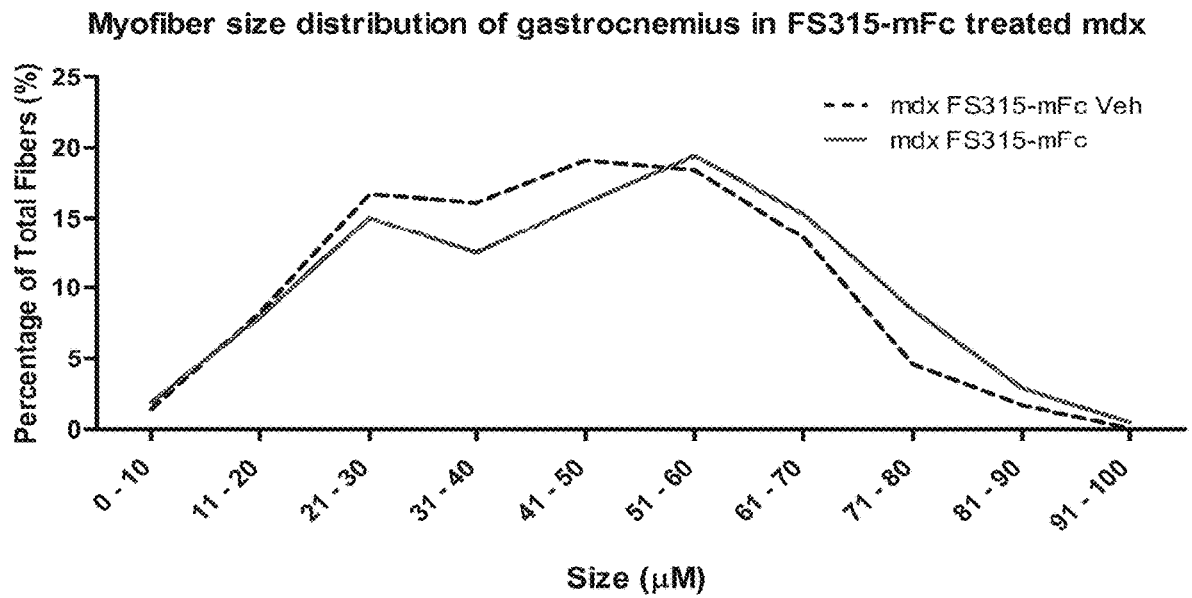

In accordance with FIG. 6, FIG. 15 demonstrates an increase in the myofiber diameters of gastrocnemius muscle treated with FS315-mFc. This increase occurred in both the C57 (WT, FIG. 15A) and mdx mice (FIG. 15B). Demonstration of the shift to larger diameters indicates that the increased muscle weights are a consequence of muscle hypertrophy. Table 7 is a summary of exemplary mean diameter changes and corresponding statistical analysis.

TABLE 7

MEAN DIAMETER

| Contrast (comparison) | Mean diff | Standard error | p |
|---|---|---|---|
| WT FS315-mFc vs vehicle | 12.5 | 0.8 | <0.0001 |
| mdx FS315-mFc vs vehicle | 5.3 | 1.2 | <0.0001 |
| No injection WT vs mdx | 14.6 | 5.8 | 0.04 |

The statistical model used was a hierarchical linear model (HLM), which is able to account for the multiple measurements made within each animal. The differences between untreated and treated legs within each strain and treatment group are highly significant (p<0.0001, which corroborate the muscle weight data).

These data demonstrate that follistatin, in particular, follistatin-Fc fusion protein can effectively induce muscle growth and treat muscle atrophy associated with DMD.

Example 5. In Vivo Efficacy of Exemplary Follistatin Variants

The in vivo half-life and efficacy data based on the wild-type follistatin FS315 protein shown in Examples 2-4 demonstrates that follistatin can be used as an effective protein therapy for DMD. This example demonstrates that protein therapeutics can also be developed based on follistatin variants.

Specifically, exemplary follistatin domain deletions or point mutations were generated as described in Table 8 below and tested for their muscle regeneration efficacy using a well-established IM/AAV delivery system to facilitate the comparison between the variants and the wild-type follistatin.

In this study, a total of 35 C57 mice aged 3-4 weeks were used across seven groups. The seven groups included five mice each, with five follistatin variants being tested (Table 8), and wild type FS315 and an empty vector used as controls. The gene encoding for FS315 has an additional 29 amino acids representing the signal peptide that is cleaved upon secretion from the cell. Thus, FS315 and FS344 refer to the same wild type construct and are used interchangeably in the examples below.

TABLE 8

Efficacy Screening of Exemplary Follistatin Variants

| Variant | Mutation |
|---|---|
| dFSD2 | Domain 2 deletion |
| dFSD3 | Domain 3 deletion |
| FSD1/1/3 | Domain 2 deletion, replacement with Domain 1 |
| Y185A | Point mutant/Domain 2 |
| L191D | Point mutant/Domain 2 |

The follistatin variants were administered via a single unilateral injection into the left quadriceps and left gastrocnemius using an AAV9 vector at a dose of approximately $1 \times 10^{11}$ viral particles per animal. The following endpoints were examined at 2, 4 and 6 weeks post injection: Follistatin levels in serum and urine, mouse weight, individual muscle weights (both injected and distal muscle groups), and histology (e.g., fiber counts, size and type, etc.). The contralateral muscle served as an intra-animal comparator for this study.

Figure 7:
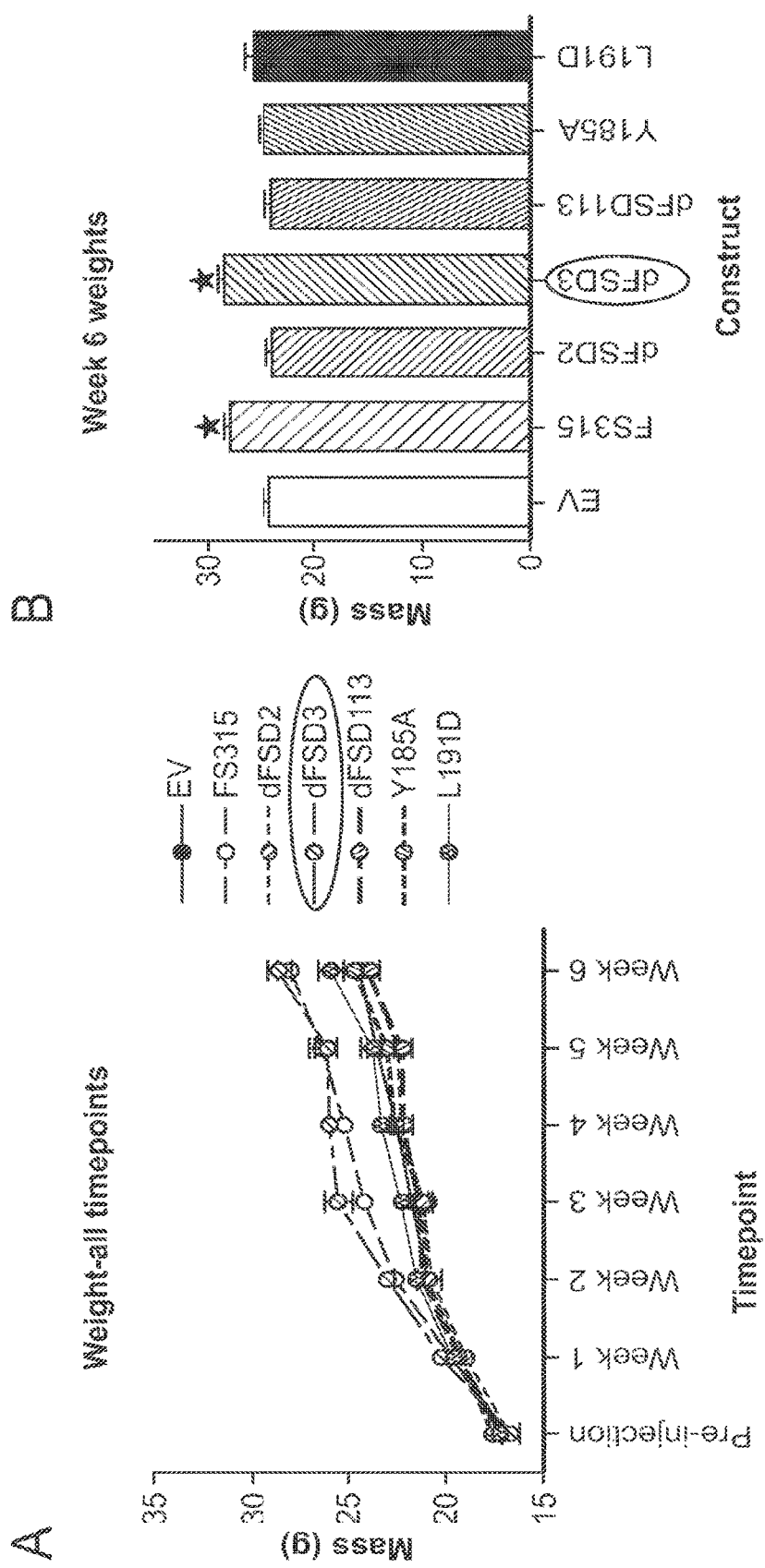
FIG. 7 shows exemplary results illustrating the effects of follistatin wild-type and variants on body weight. Panel A shows exemplary average body weight of animals in each group over time, and panel B shows exemplary average body weight of animals in each group at week 6 post-injection.

As shown in FIG. 7, both the wild type FS315 and the domain 3 deletion mutant significantly increased body weight as compared to empty vector control. In particular, the tested domain 3 deleted follistatin variant increases body weight as early as 3 weeks post-injection.

Figure 8:
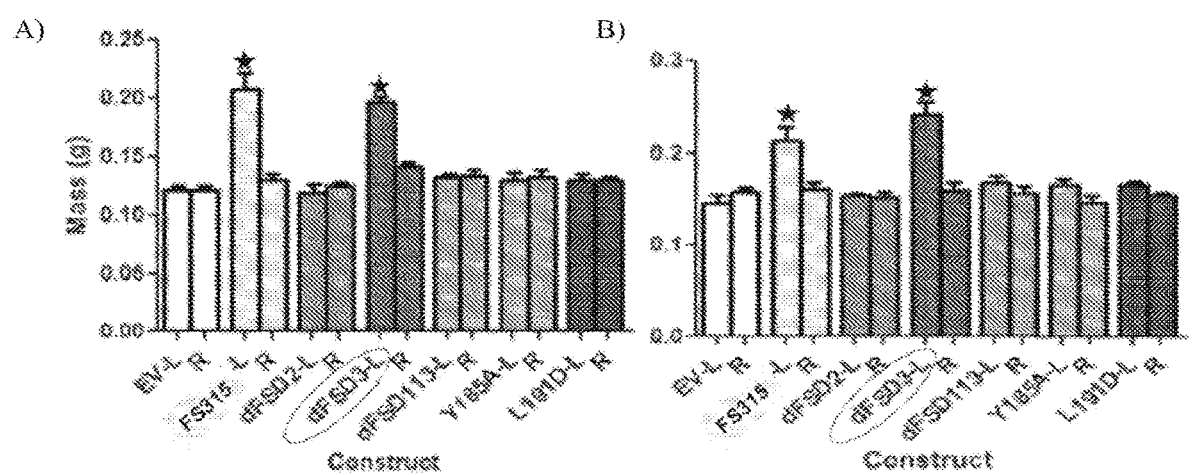
FIG. 8 shows exemplary results illustrating the effect of follistatin variants on the weight of injected muscle at week 2 post-injection. Panel A shows the mass of the injected muscle gastrocnemius while panel B shows the mass of the injected muscle quadriceps.
Figure 9:
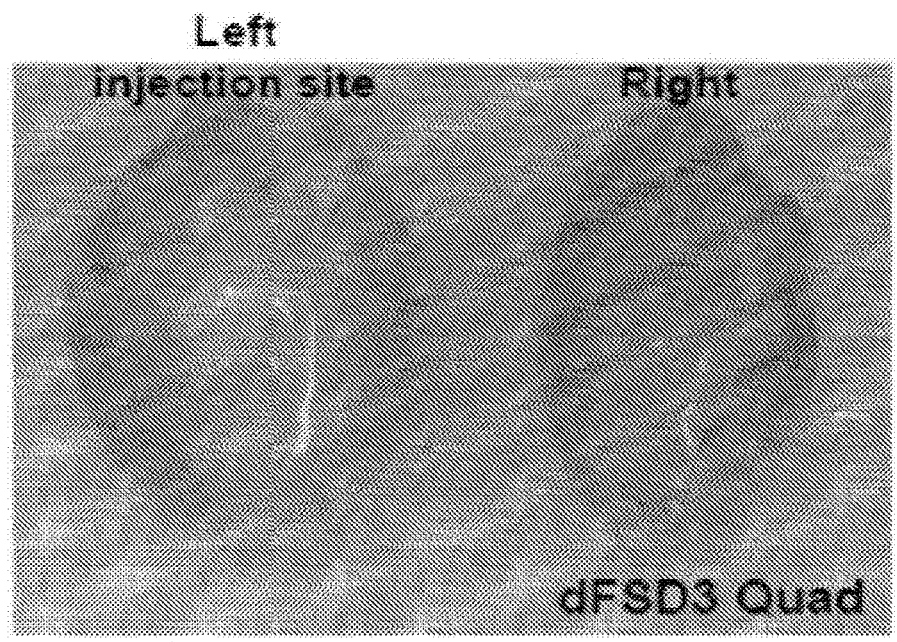
FIG. 9 shows exemplary results illustrating the effect of domain 3 deletion on injected muscle and muscle remote from the injection site two weeks post-injection. The left quadriceps was a site of injection while the right quadriceps is the contralateral intra-animal control muscle.

FIG. 8 shows exemplary average muscle weights of the A) gastrocnemius and B) quadriceps on both the ipsilateral and contralateral sides two weeks post-injection. Both wild type FS315 and the domain 3 deletion follistatin variants showed significantly increased muscle mass on the ipsilateral side by week 2 post-injection (FIG. 8). In particular, muscles injected with FS315 and dFSD3 were 60% to 70% greater in weight as compared to empty vector (FIG. 8). The dissected quad muscle that was injected with dFSD3 was noticeably larger than the contra-lateral untreated muscle at week 2 (FIG. 9).

Figure 10:
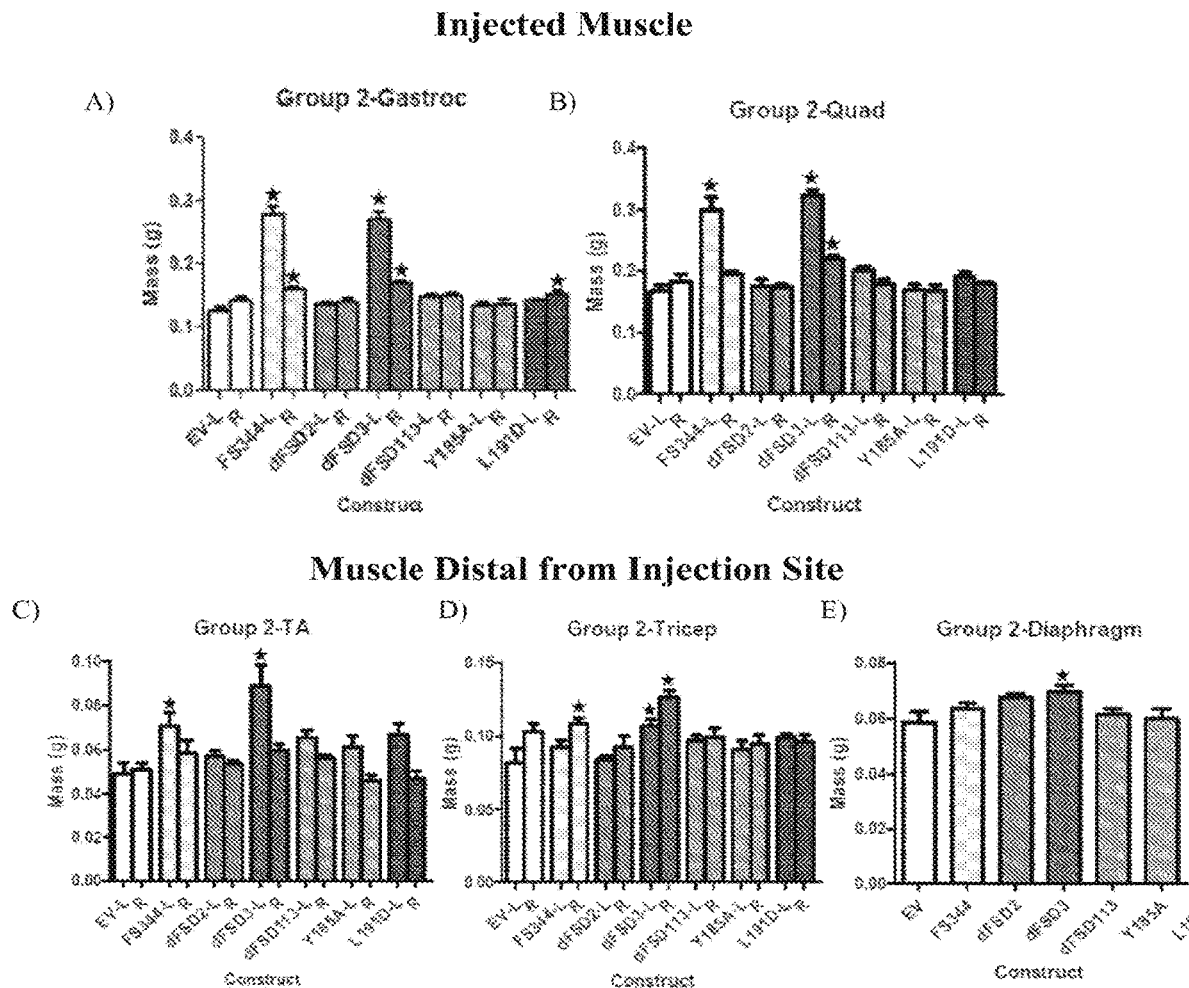
FIG. 10 shows exemplary results illustrating the effect of follistatin variants on the weight of specific muscles in injection site and distal from the injection site at week 4 post-injection. Panel A (gastrocnemius) and panel B (quadriceps) are injected muscle. Panel C (tibialis anterior), Panel D (triceps) and Panel E (diaphragm) are muscle distal from injection site.
Figure 11:
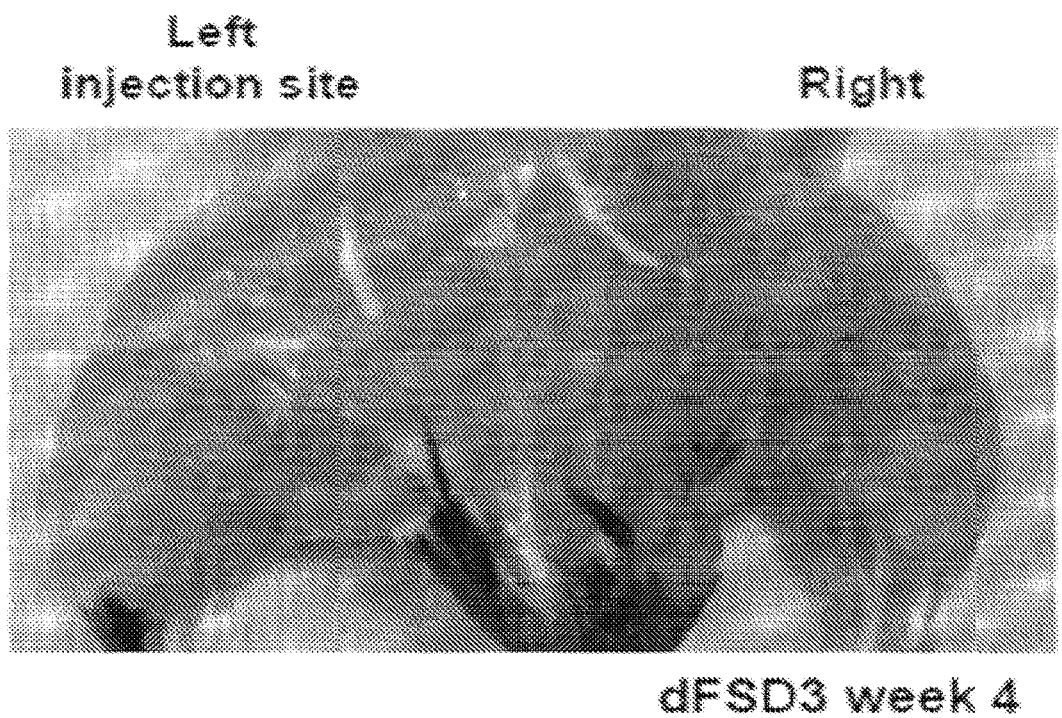
FIG. 11 shows exemplary results illustrating the effect of domain 3 deletion on injected muscle and muscle remote from the injection site four weeks post-injection. The left quadriceps was a site of injection while the right quadriceps is the contralateral intra-animal control muscle.

At week 4, domain 3 deleted and wild-type follistatin increased muscle mass in both injected and distal muscle. See FIG. 10. As observed at week 2, dFSD3 caused a significant hypertrophic effect at week 4, with noticeably larger muscle mass in injected muscle compared to the untreated side (FIG. 11). Follistatin levels in serum, determined by ELISA, were similar for the wild-type and dFSD3 treated mice, and averaged 30 ng/mL at weeks 2, 4 and 6 (data not shown).

Figure 12:
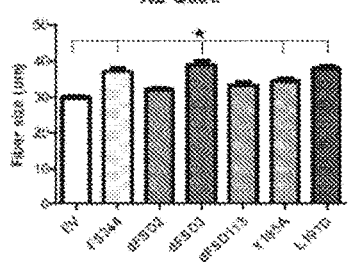
FIG. 12 shows exemplary results illustrating the effect of follistatin variants on fiber size in both injected muscles and distal muscles at week 2 post-injection in the (A) quadriceps, (B) gastrocnemius, (C) tibialis anterior, (D) triceps, and (E) diaphragm.
Figure 12:
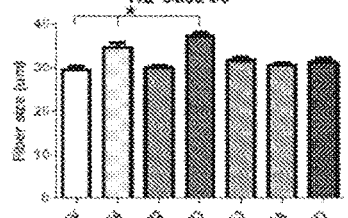
Figure 12:
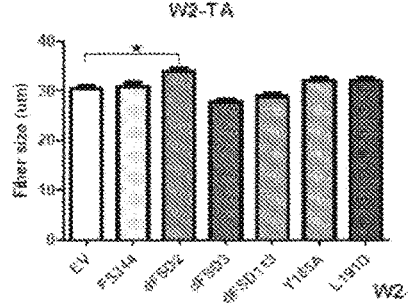
Figure 12:
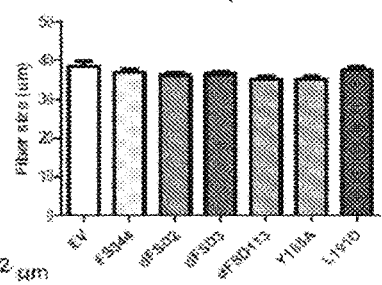
Figure 12:
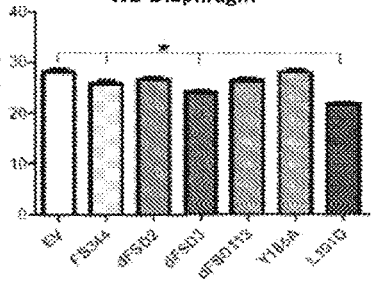
Figure 13:
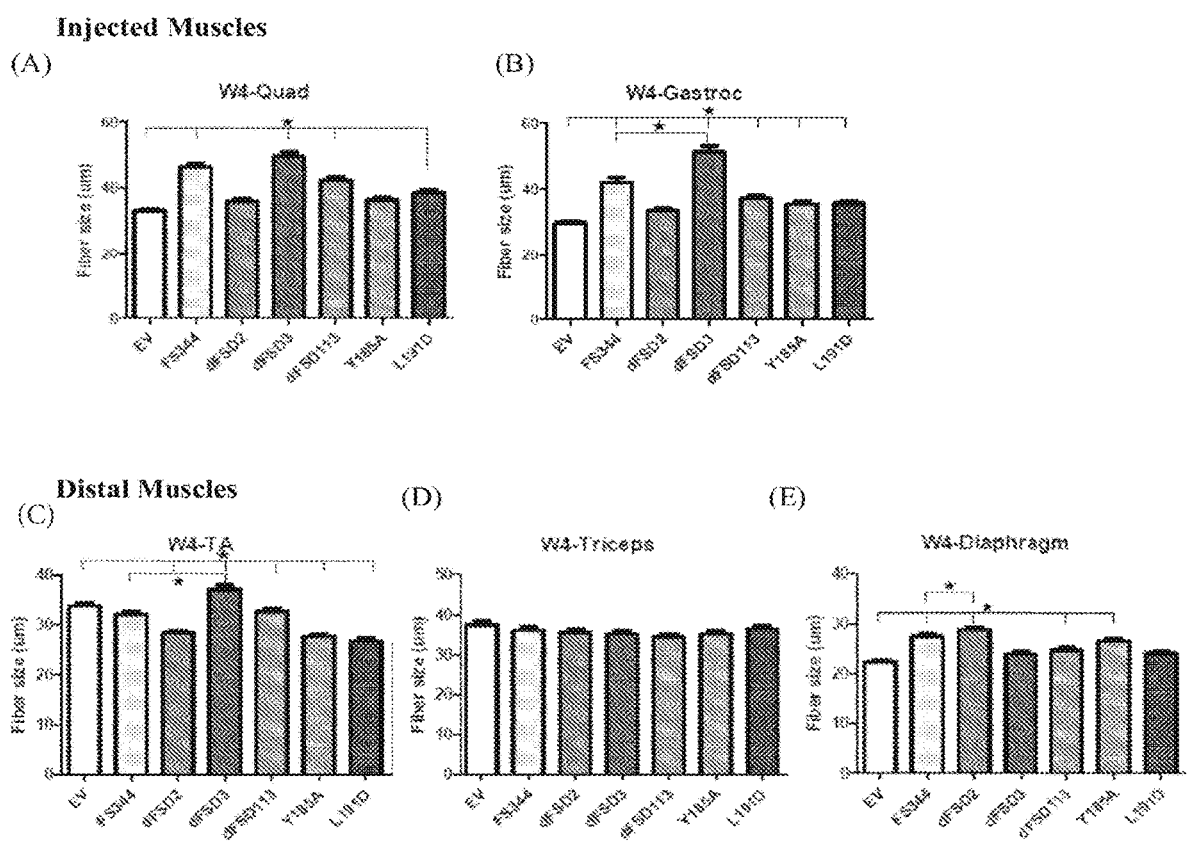
FIG. 13 shows exemplary results illustrating the effect of follistatin variants on fiber size in both injected muscles and distal muscles at week 4 post-injection, in the (A) quadriceps, (B) gastrocnemius, (C) tibialis anterior, (D) triceps, and (E) diaphragm.
Figure 14:
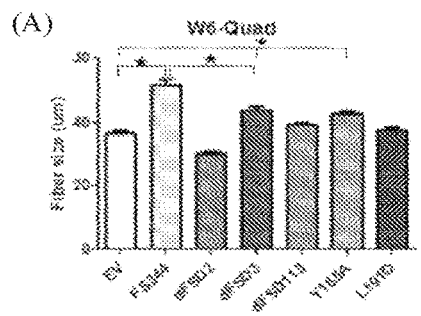
FIG. 14 shows exemplary results illustrating the effect of follistatin variants on fiber size in both injected muscles and distal muscles at week 6 post-injection, in the (A) quadriceps, (B) gastrocnemius, (C) tibialis anterior, (D) triceps, and (E) diaphragm.
Figure 14:
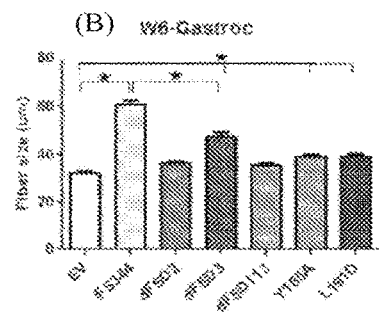
Figure 14:
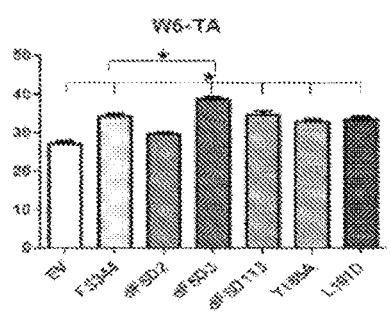
Figure 14:
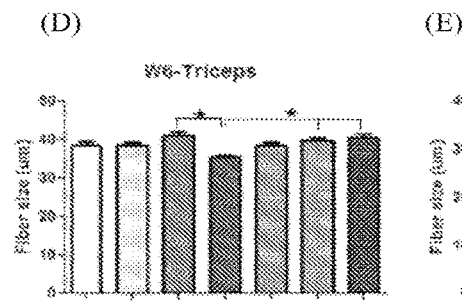
Figure 14:
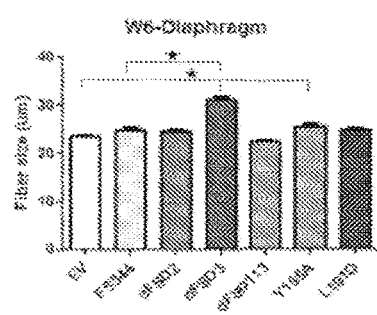

Myofiber size was also determined in both injected and distal muscle tissues at week 2, 4 and 6 post-injection using standard histological and immunohistochemical methods. Exemplary week 2, 4 and 6 results are shown in FIGS. 12, 13 and 14, respectively. All statistics were done using 1 way ANOVA with Dunnett's Multiple Comparison Test in GraphPad Prism. Error bars represent SEM.

As shown in FIG. 12, at week 2, in injected muscles, myofiber hypertrophy was observed in Quad in the FS344 (23%), dFSD3 (30%), Y185A and L191D groups and in Gastroc in the FS344 (17%) and dFSD3 (25%) groups. In distal muscle groups, myofiber hypertrophy was observed in TA in the dFSD2 (12%) group. No hypertrophy was observed in Triceps or Diaphragm.

As shown in FIG. 13, at week 4, in injected muscles, myofiber hypertrophy was observed in Quad in the FS344 (41%), dFSD3 (50%), dFSD113 and L191D groups and in Gastroc in the FS344 (42%), dFSD2, dFSD3 (73%), dFSD113, Y185A and L191D groups. In distal muscle groups, hypertrophy was observed in TA in the dFSD3 (10%) group and in Diaphragm in the FS344 (23%) and dFSD2 (29%) groups. No hypertrophy was observed in Triceps.

As shown in FIG. 14, at week 6, in injected muscles, myofiber hypertrophy was observed in Quad in the FS344 (41%), dFSD3 (30%), Y185A groups and in Gastroc in the FS344 (90%), dFSD3 (49%), Y185A, L191D groups. In distal muscles, myofiber hypertrophy was observed in TA in the FS344 (26%), dFSD3 (41%), dFSD113, Y185A, and L191D groups and in Diaphragm in the dFSD3 (35%) group. Minimal hypertrophy was observed in Triceps.

Taken together, these results indicate that protein therapeutics may be developed based on follistatin variants. For example, follistatin domain deletions or point mutations may retain or improve muscle regeneration efficacy. As shown above, domain 3 deletion can be a particularly useful follistatin variant for treating DMD.

Example 6. Systemic Efficacy of FS315-GAG3-mFc

As shown in Example 4, injection of FS315-mFc into the gastrocnemius resulted in increased muscle mass versus control muscles. This example shows that systemic injection of FS315-mFc is also capable of inducing muscle growth at various sites distal to the site of injection. All follistatin constructs used in this example contain a GAG3 linker.

A total of 20 C57BL/6 mice were used in this study with half of the animals receiving a subcutaneous (interscapular) injection of PBS twice per week for 8 weeks (control) and the other half receiving a subcutaneous (interscapular) injection of 10 mg/kg FS315-mFc twice per week for 8 weeks. Animals were sacrificed 24 hours after the last injection and the weight of the left and right quadriceps, gastrocnemius, tibialis anterior and triceps were measured, as was total body weight of the animal. Table 9 below outlines the experimental design for this example.

TABLE 9

Experimental Design

| Group | N | Mouse Strain | Test Article | Injection Route | Dose | Dosing Schedule | Sacrifice (24 hours post last injection) |
|---|---|---|---|---|---|---|---|
| A | 10 | WT C57BL/6 | FS315-mFc | SC (Interscapular) | 10 mg/kg | Twice weekly | 4 weeks |
| B | 10 | WT C57BL/6 | FS315-mFc | SC (Interscapular) | 10 mg/kg | Twice weekly | 8 weeks |
| C | 10 | WT C57BL/6 | Vehicle (PBS) | SC (Interscapular) | NA | Twice weekly | 4 weeks |
| D | 10 | WT C57BL/6 | Vehicle (PBS) | SC (Interscapular) | NA | Twice weekly | 8 weeks |

Figure 16:
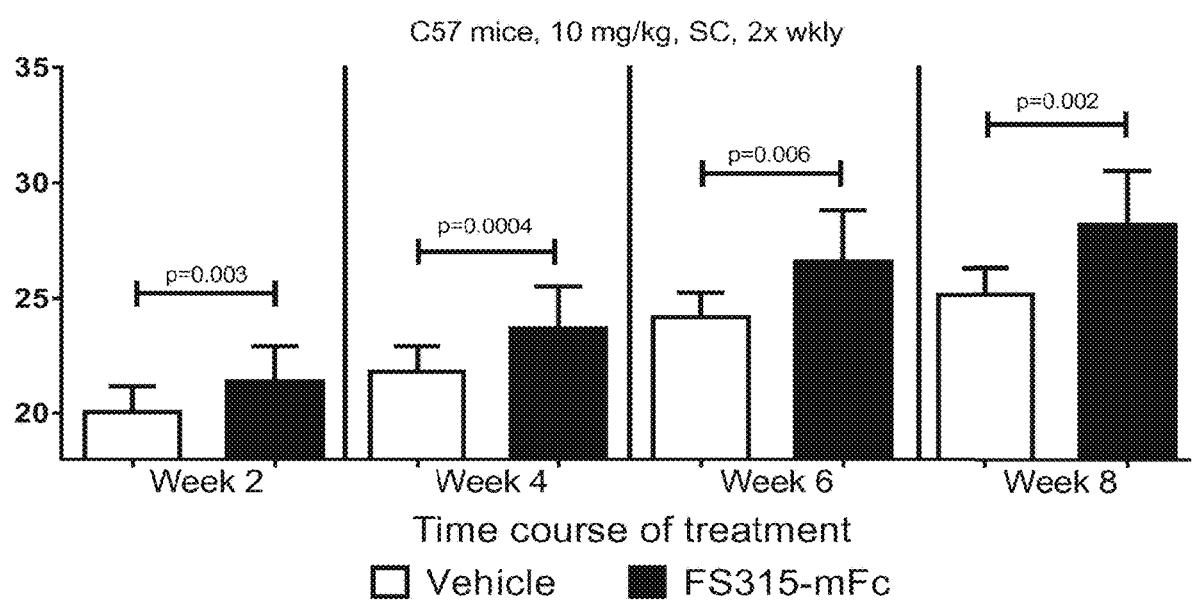
FIG. 16 shows exemplary results demonstrating the effect of an exemplary follistatin-Fc protein on the body weight of treated C57 mice after 2, 4, 6, or 8 weeks of exposure, as compared to vehicle control animals.
Figure 17:
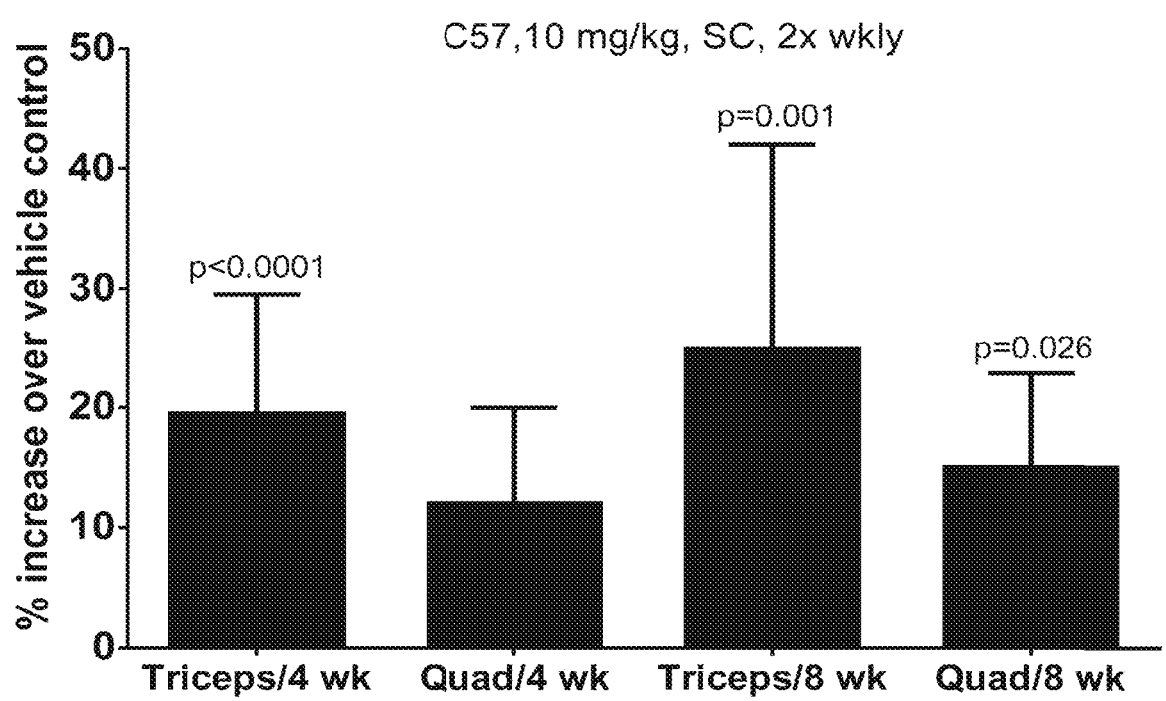
FIG. 17 shows exemplary results demonstrating the effect of an exemplary follistatin-Fc protein on the weight of the triceps and quadriceps of treated animals as a percent increase over vehicle control animals, after 4 and 8 weeks of exposure.
Figure 18:
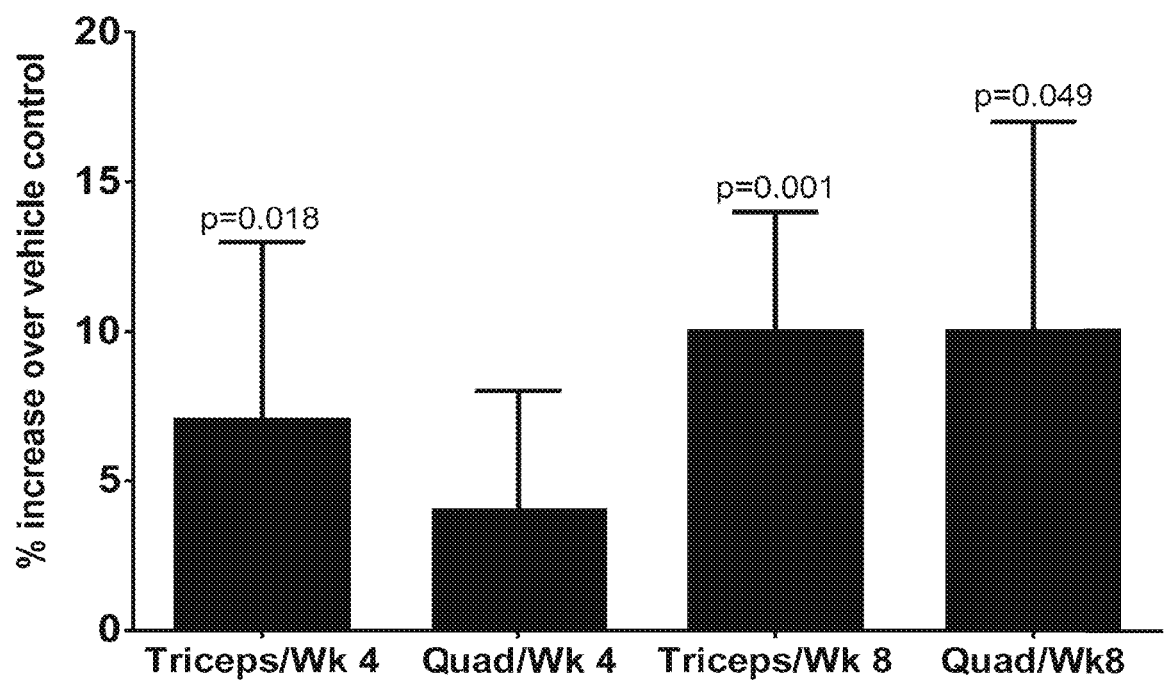
FIG. 18 shows exemplary results demonstrating the effect of an exemplary follistatin-Fc protein on the diameter of myofibers in the triceps and quadriceps of treated animals as percent increase over vehicle control animals after 4 and 8 weeks of exposure.

FIG. 16 shows exemplary body weight data through the 8 week course of the study. As can be seen, body weights for the FS315-mFc treated animals were significantly greater than those vehicle treated control animals beginning at 2 weeks and continuing throughout the 8 week study. FIG. 17 represents exemplary muscle weight data. The triceps muscles from mice treated with FS315-mFc were significantly greater in weight compared to vehicle control as early as week 4. After 8 weeks of treatment, both triceps and quadriceps muscle groups demonstrated significant increases in weight compare to vehicle (FIG. 17). Myofiber size was determined by the method described in Example 4. FIG. 18 shows the percent increase in myofiber diameter for the triceps and quadriceps muscle groups at weeks 4 and 8. Both muscle groups demonstrated a shift towards greater myofiber size after treatment with FS315-mFc at both 4 and 8 weeks.

Figure 19:
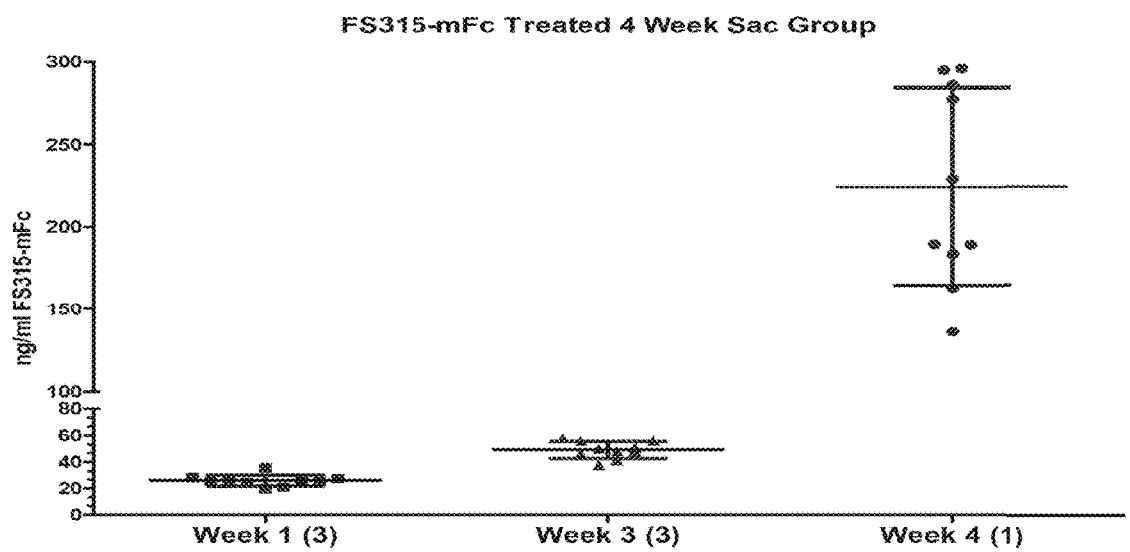
FIG. 19 shows exemplary levels of follistatin-Fc protein in the serum of animals administered the fusion protein via twice weekly subcutaneous injection after 1, 3, 4, 6, or 8 weeks of exposure. Panel A) shows the results from animals euthanized after 4 weeks and panel B) shows the results from animals euthanized after 8 weeks of exposure.
Figure 19:
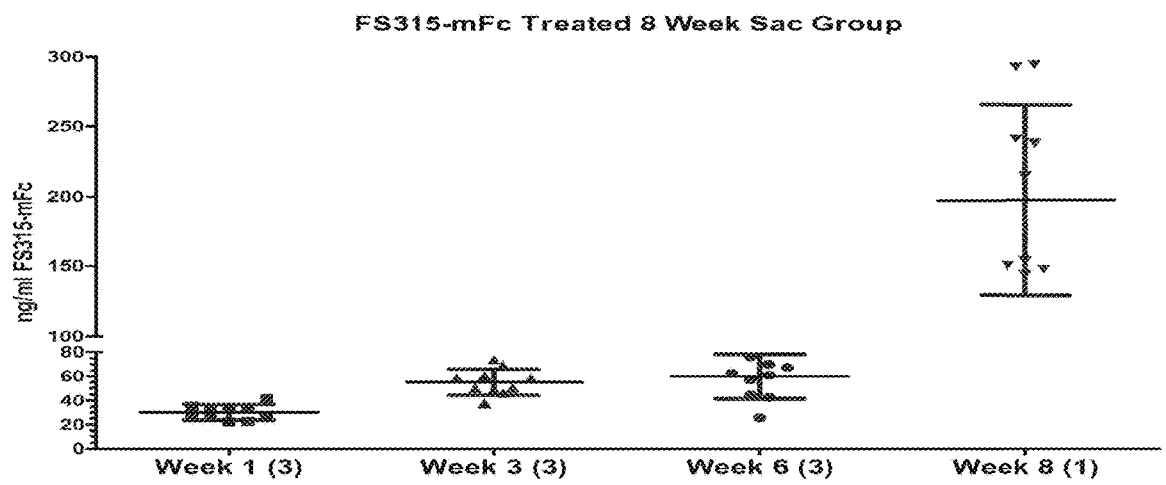

In addition, serum follistatin levels were increased following subcutaneous injection. For example, FS315-mFc levels in the sera of treated mice (by twice weekly subcutaneous injection) are shown in FIG. 19. FS315-mFc levels were highest in the serum collected at weeks 4 and 8 sacrifice time points, consistent with the amount of time between the FS315-mFc injection and the serum collection (24 h). At these points, serum levels of FS315-mFc averaged about 200 ng/mL. The biweekly retro-orbital bleeds were collected 3 days after FS315-mFc injection, and serum levels of FS315-mFc averaged between about 30-50 ng/mL.

These data demonstrates that systemic injection of FS315-mFc (e.g., subcutaneous injection) can effectively induce muscle growth in various muscle tissues throughout the body.

Example 7. Systemic Efficacy of Follistatin-Fc Fusion Protein in DMD Mouse Model This example further demonstrates systemic efficacy in DMD disease model. In particular, as shown below, systemic injection of FS315-mFc successfully reduced progression of various characteristic DMD symptoms such as muscle necrosis and/or fibrosis. All follistatin constructs used in this example contain a GAG3 linker.

The mdx mouse model has been used extensively as the preclinical model for demonstrating proof of concept of candidate therapies for DMD. Both the limb muscle groups and diaphragm of the mdx mouse show extensive pathology that tends to increase with age. Such pathology is characterized by areas of inflammatory infiltrate, necrosis, and fibrosis in muscle. FS315-mFc was tested in this model to evaluate its effect on progression of fibrosis in muscle. A total of 50 mdx mice were used in this Example, with 20 animals receiving a subcutaneous injection of PBS, and 30 animals receiving a subcutaneous injection of 10 mg/kg FS315-mFc twice per week for 12 weeks. (see Table 10). Animals were sacrificed 24 hours after the last injection and tissues were collected for analysis of necrosis and fibrosis (see Table 11).

TABLE 10

Experimental Design

| Group | N | Test Article | Injection Route | Dose | Dosing Schedule | Sacrifice (24 hours post last injection) |
|---|---|---|---|---|---|---|
| A | 15 | FS315-mFc | SC | 10 mg/kg | Twice weekly | 6 weeks |
| B | 10 | PBS | SC | N/A | Twice weekly | 6 weeks |
| C | 15 | FS315-mFc | SC | 10 mg/kg | Twice weekly | 12 weeks |
| D | 10 | PBS | SC | N/A | Twice weekly | 12 weeks |

TABLE 11

Tissue collection and processing

| Diaphragm | Quadriceps | Gastrocnemius | Triceps |
|---|---|---|---|
| ½ snap frozen for protein analysis | 1 snap frozen for protein analysis | 1 snap frozen for protein analysis | 1 snap frozen for protein analysis |
| ½ fixed in formalin for histologic alanalysis | 1 fixed in formalin for histological analysis | 1 fixed in formalin for histological analysis | 1 fixed in formalin for histological analysis |

Figure 20:
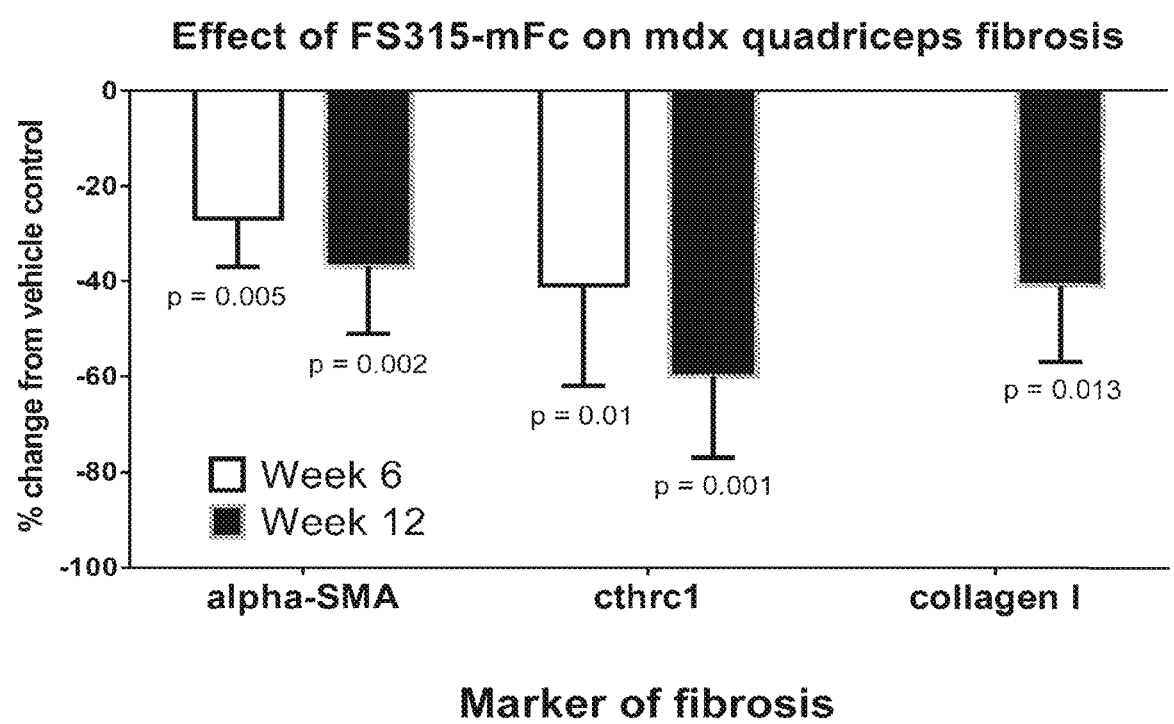
FIG. 20 shows exemplary results demonstrating the effect of follistatin-Fcprotein on the mRNA expression of three markers of fibrosis: alpha-smooth muscle actin, collagen triple helix repeat containing 1 protein (cthrc1), and collagen I, in the quadriceps of treated animals as compared to vehicle control animals after 6 or 12 weeks of exposure.

FIG. 20 shows exemplary effect of FS315-mFc on fibrotic protein expression at the RNA level. Specifically, RT-PCR of collagen type I, alpha-smooth muscle actin, and collagen triple helix repeat containing 1 protein demonstrated a significant reduction in the expression of these fibrosis-related proteins as early as 6 weeks after twice weekly SC treatment.

Figure 21:
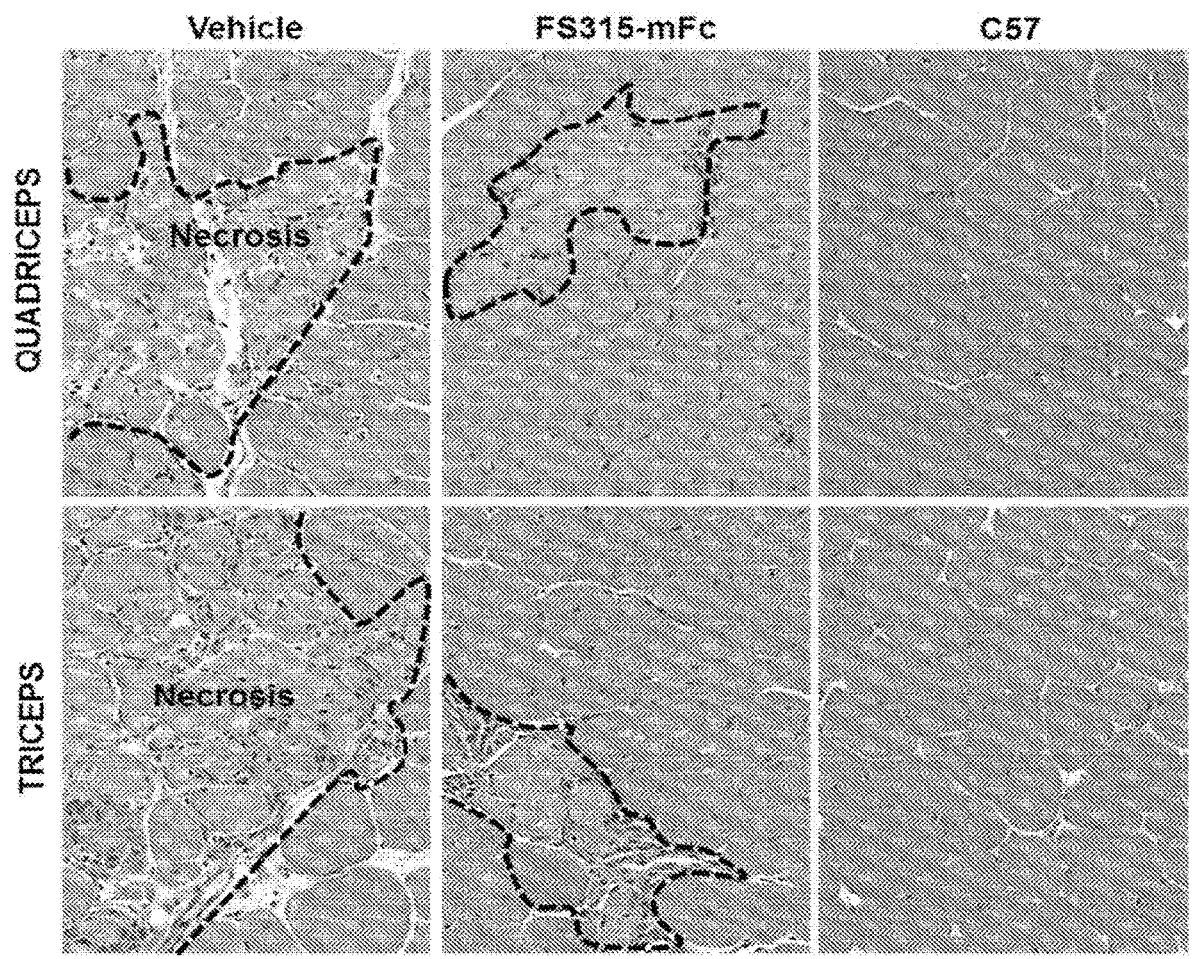
FIG. 21 shows exemplary H&E stained sections of quadriceps and triceps tissue of mdx mice treated with vehicle or follistatin-Fc protein for six weeks. Also shown are exemplary H&E stains from the quadriceps and triceps of C57 control mice.
Figure 22:
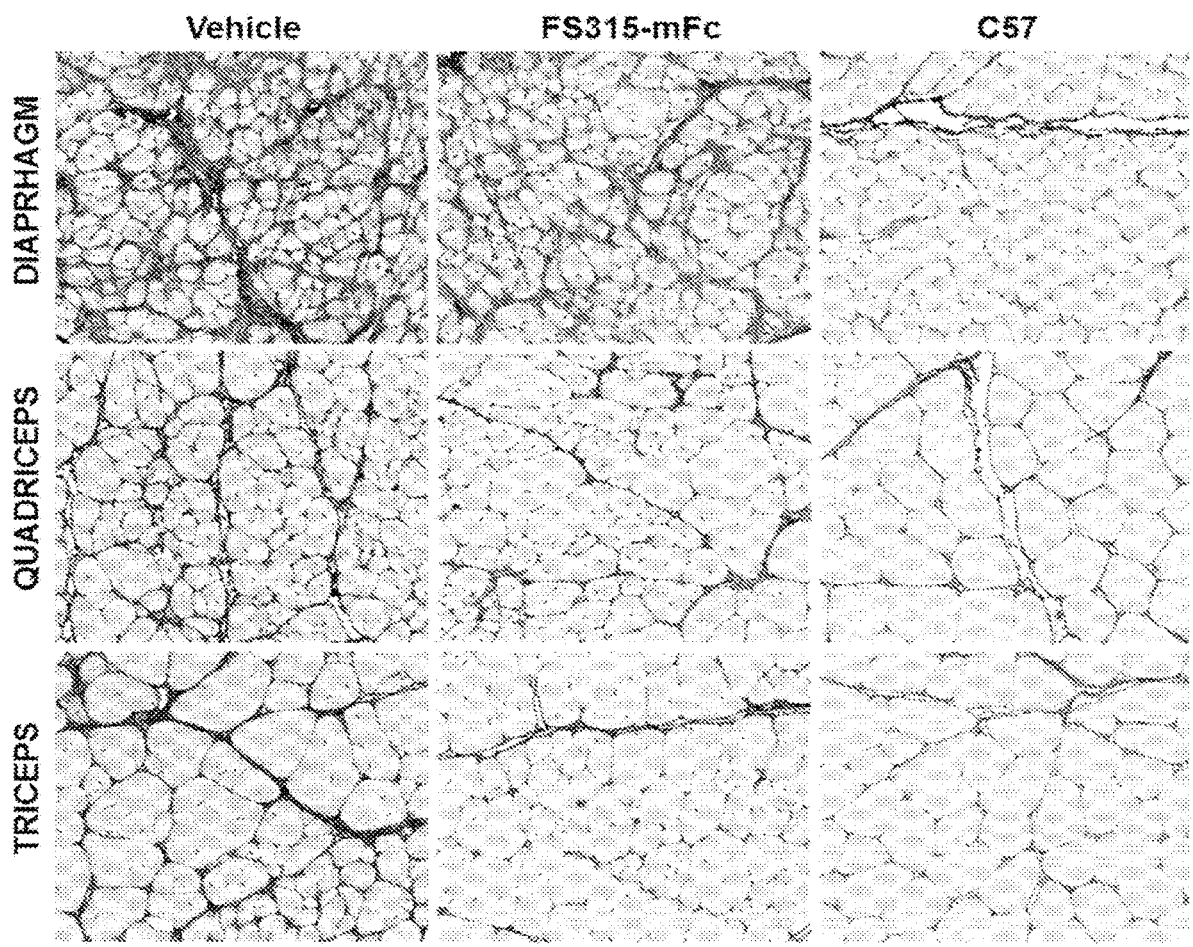
FIG. 22 shows exemplary collagen I stained sections of quadriceps, triceps, and diaphragm tissue of mdx mice treated with vehicle or follistatin-Fc protein for twelve weeks. Also shown are exemplary collagen I stains from the quadriceps, triceps and diaphragm of C57 control mice.

Tables 12 and 13 summarize the histopathological evaluation of necrosis (as determined by evaluation of H&E stained sections) and fibrosis (as determined by evaluation of collagen I stained muscle sections in FS315-mFc treated mdx mouse muscle) in muscle tissue sections. For the FS315-mFc and vehicle treated groups, there were 15 and 10 total animals per group, respectively. As indicated in Table 12, FS315-mFc treatment significantly reduced the incidence of necrosis in limb muscles as early as 6 weeks from initiation of twice weekly injections. This reduction in necrosis is illustrated in the images of H&E sections through quadriceps and triceps muscle (FIG. 21). The incidence of fibrosis, demonstrated by collagen I staining of muscle tissue sections, was significantly reduced after 12 weeks of FS315-mFc treatment (also see Table 13). This reduction in collagen deposition is illustrated in the images of collagen I stained muscle sections (FIG. 22).

The results of this study demonstrates that FS315-mFc can successfully treat DMD by effectively reducing the progression of the diseased muscle pathology in the DMD mouse model including, but not limited to, muscle necrosis and/or fibrosis

TABLE 12

Incidence of necrosis in FS315-mFc treated mdx mouse muscle (p values indicate degree of significance between vehicle and FS315-mFc, using Fisher's Exact Test)

| Score | Vehicle | FS315-mFc | Vehicle | FS315-mFc |
|---|---|---|---|---|
| | Week 6 Quad p = 0.001 | | Week 12 Quad p = 0.049 | |
| Minimal | 10% | 67% | 30% | 73% |
| Mild | 40% | 33% | 70% | 27% |
| Marked | 50% | 0% | 0% | 0% |
| | Week 6 Triceps p < 0.001 | | Week 12 Triceps p = 0.02 | |
| Minimal | 0% | 53% | 20% | 73% |
| Mild | 10% | 33% | 70% | 20% |
| Marked | 90% | 14% | 10% | 7% |
| | Week 6 Gastroc p < 0.001 | | Week 12 Gastroc p = 0.007 | |
| Minimal | 0% | 73% | 20% | 80% |
| Mild | 40% | 27% | 60% | 20% |
| Marked | 60% | 0% | 20% | 0% |

Minimal: <5%; mild: <30%; marked: >30% in total checked muscle area

TABLE 13

Incidence of fibrosis, (p values indicate degree of significance between vehicle and FS315-mFc, using Fisher's Exact Test)

| Score | Vehicle | FS315-mFc |
|---|---|---|
| | Week 12 Quad p = 0.0001 | |
| Minimal | 0% | 80% |
| Mild | 70% | 20% |
| Marked | 30% | 0% |
| | Week 12 Triceps p = 0.001 | |
| Minimal | 0% | 67% |
| Mild | 80% | 20% |
| Marked | 20% | 13% |
| | Week 12 Gastroc p < 0.0001 | |
| Minimal | 0% | 73% |
| Mild | 20% | 27% |
| Marked | 80% | 0% |

Minimal: ~1%; mild: <5%; marked: >5% in total checked muscle area

Example 8. In Vivo Efficacy of Recombinant Follistatin Domain 3 Deletion Fc Fusion Protein This Example demonstrates that a follistatin domain 3 deletion (dFSD3) Fc fusion protein effectively induced muscle growth in vivo, similar to wild type follistatin-Fc fusion protein. All follistatin constructs used in this example contain a GAG3 linker.

Figure 23:
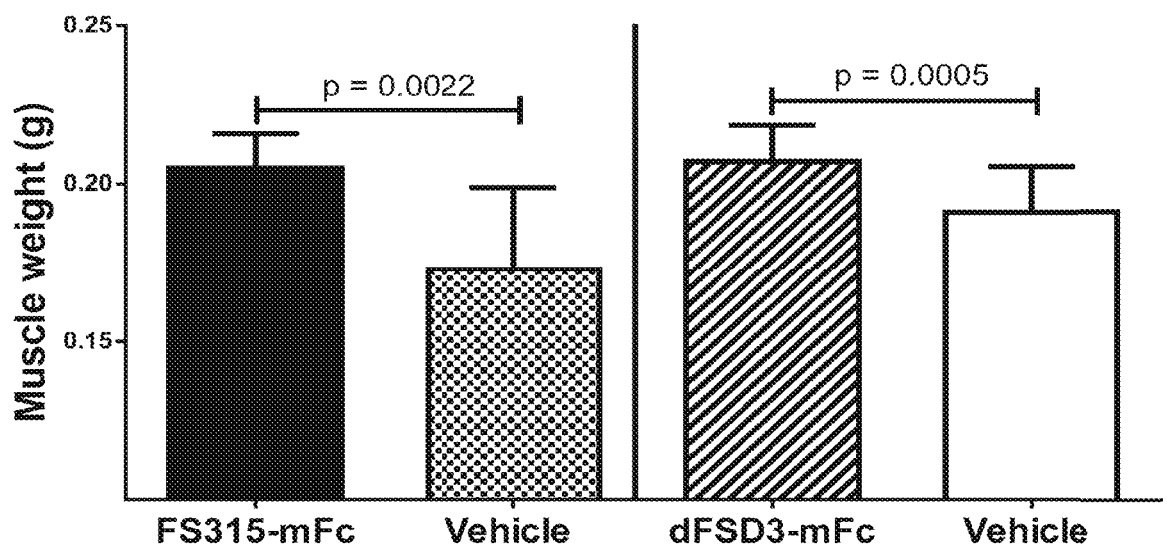
FIG. 23 shows exemplary results demonstrating the effects of twice weekly intramuscular injections of one of two follistatin variants, a FS315-mFc fusion protein and a dFSD3-mFc variant fusion protein, on the muscle weights of C57BL/10 mice treated for four weeks as compared to the contra-lateral vehicle control muscle.

Specifically, the domain 3 deleted construct described in Example 5 was fused to the same mFc as used for FS315-mFc. In addition, the same GAG3 linker sequence was used to fuse dFSD3 to mFc. C57BL/10 mice were injected with both fusion proteins directly into the gastrocnemius muscle, as described in Example 4. Mice were sacrificed after 4 weeks of twice weekly injections of 20 µg of fusion protein, and the opposite gastrocnemius muscle received the same volume of PBS. 24 h after the final injection, the treated mice were sacrificed and the injected gastrocnemius muscles were carefully injected and weighed. As indicated in FIG. 23, the dFSD3-GAG3-mFc fusion protein led to a significant increase in muscle mass over vehicle control, and the increase was similar to that observed with FS315-mFc. This Example indicates that a follistatin domain 3 deletion Fc fusion protein (e.g., dFSD3-GAG3-mFc) is active in vivo and another promising therapeutic candidate for DMD treatment.

Example 9. Advantage of Longer Linker on Follistatin Function

Figure 24:
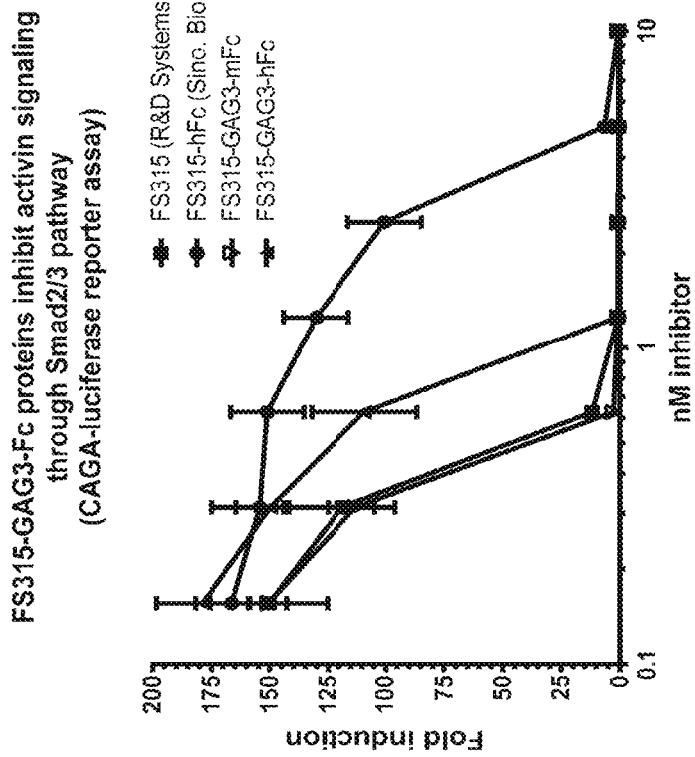
FIG. 24 shows exemplary results demonstrating that the FS315-GAG3-mFc and FS315-GAG3-hFc fusion proteins inhibit (A) myostatin and (B) activin signaling in the CAGA-luciferase assay to the same extent as native FS315. In comparison, Sino Biological FS315-hFc (manufactured by Sino Biological Inc. Catalog Number 10685-H02H) which contains a 9 amino acid linker is significantly less potent.
Figure 24:
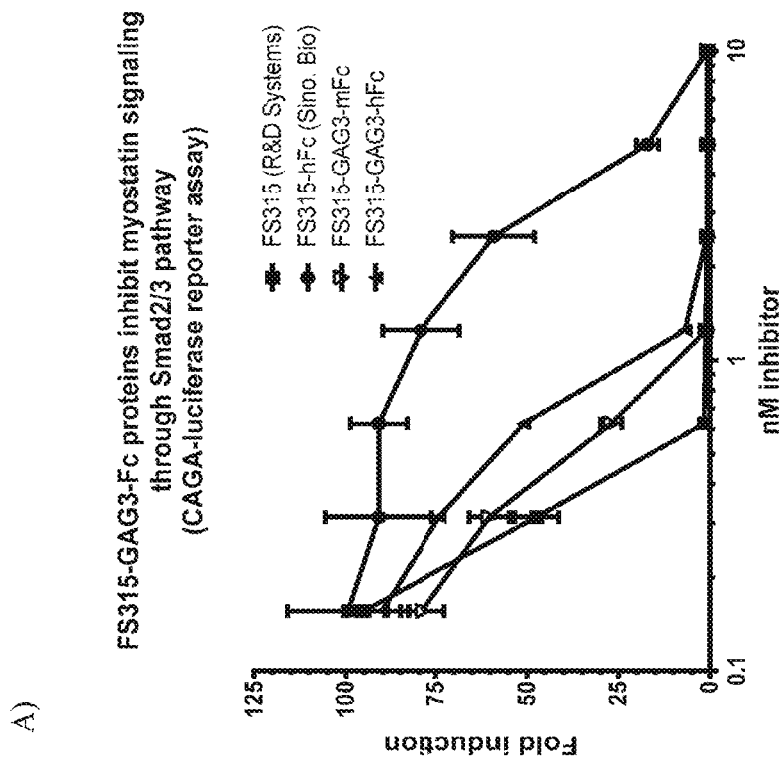

This example demonstrates that a longer linker, in particular a linker containing at least 10 amino acids, provides unexpected advantage on follistatin function. Specifically, this example shows that the FS315-GAG3-Fc fusion protein (murine and/or human Fc), containing a 57 amino acid linker, is more potent in its ability to inhibit myostatin and activin compared to a commercial available FS315-hFc fusion protein from Sino Biological (Sino Biological Inc. Catalog Number 10685-H02H), which contains a 9 amino acid linker ALEVLFQGP (SEQ ID NO: 18). The concentration of myostatin and activin used for the signaling assay was 1.2 nM. As indicated in FIG. 24 and Table 14, the FS315-GAG3-mFc and FS315-GAG3-hFc fusion proteins inhibit myostatin and activin signaling in the CAGA-luciferase assay to the same extent as native FS315. In comparison, the commercially available FS315-hFc fusion protein (Sino Biological) is significantly less potent. The calculated IC50's are as follows:

TABLE 14

Exemplary IC50 values for follistatin inhibition of myostatin and activin in the CAGA-luciferase reporter assay for Smad2/3 signaling

| Material | Ligand | IC50 (nM) |
|---|---|---|
| FS315 (R&D Systems) | Myostatin | 0.45 |
| FS315-GAG3-mFc | Myostatin | 0.46 |
| FS315-GAG3-hFc | Myostatin | 0.68 |
| FS315-hFc (Sino Biological) | Myostatin | 2.99 |
| FS315 (R&D Systems) | Activin | 0.40 |
| FS315-GAG3-mFc | Activin | 0.36 |

TABLE 14-continued

Exemplary IC50 values for follistatin inhibition of myostatin and activin in the CAGA-luciferase reporter assay for Smad2/3 signaling

| Material | Ligand | IC50 (nM) |
|---|---|---|
| FS315-GAG3-hFc | Activin | 0.70 |
| FS315-hFc (Sino Biological) | Activin | 2.90 |

Without wishing to be held to a particular theory, it is possible that a longer linker (e.g., a 57 amino acid linker in this particular construct FS315-GAG3-Fc) between the FS315 protein and the Fc region may permit a more native conformation of FS315 as compared to a fusion protein with a much shorter linker (e.g., 9 amino acids), allowing for binding to target ligands and inhibition of signaling to a similar extent as that observed with native FS315. In comparison, the commercially available FS315-hFc protein has a much shorter linker of 9 amino acids, with significantly less separation between the Fc and the FS315 protein, potentially causing a detrimental effect on FS315 conformation and physiological activity.

Figure 25:
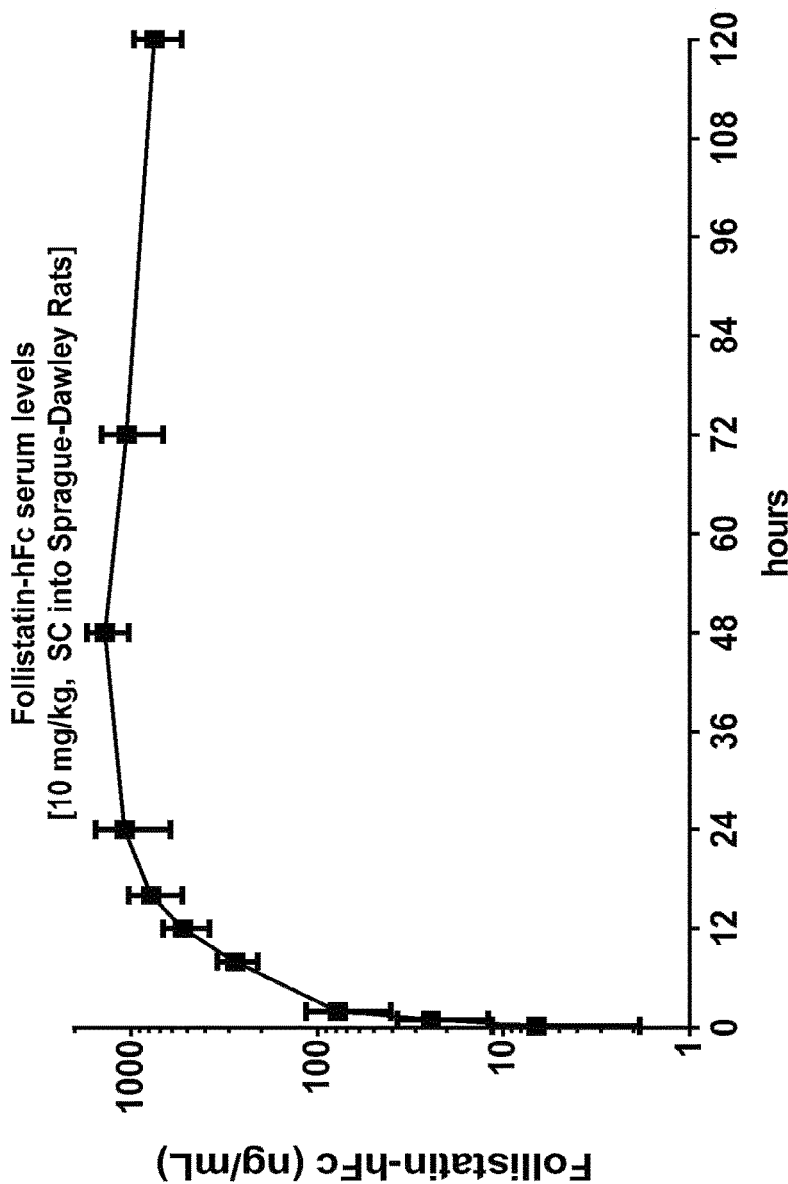
FIG. 25 shows levels of FS315-GAG3-hFc protein in the serum of rats dosed with a single SC injection of 10 mg/kg protein. The calculated serum half-life was 3.5 days.

Example 10. Follistatin Fusion Protein FS315-GAG3-hFc has Extended Serum Half-Life In this example, we demonstrated that provided follistatin fusion proteins, in particular, those with a longer linker (e.g., a linker with at least 10 amino acids) has extended serum half-life. Specifically, for the first time, we demonstrated here a FS315 fused to human Fc with the GAG3 linker (FS315-GAG3-hFc), has an extended serum half-life when administered subcutaneously (SC) into Sprague-Dawley rats at a single dose of 10 mg/kg. After administration, serum was collected at time points ranging from 15 min to 5 days. FS315-GAG3-hFc was measured in rat serum using a Mesoscale Discovery (MSD) assay that captures the human FS315 and detects the human Fc domain of the intact fusion protein in serum samples. Levels of FS315-GAG3-hFc in rat serum are shown in FIG. 25. The PK parameters are summarized in Table 15.

TABLE 15

FS315-GAG3-hFc In Vivo PK Data

| t ½ (h) | Cmax (ng/mL) | Tmax (h) | $AUC_{o\text{-}last}$ (hr*ng/mL) | $AUC_{0\text{-}\infty}$ (hr*ng/mL) |
|---|---|---|---|---|
| 84 | 1372 | 48 | 114585 | 205803 |

In sum, the above Examples demonstrate that follistatin, including provided variants, are highly effective in inducing muscle hypertrophy and attenuating muscle necrosis and fibrosis in DMD disease model by, e.g., systemic administration. Thus, follistatin and provided variants can be effective protein therapeutics for the treatment of DMD.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

I claim:

1. A method of treating Duchenne muscular dystrophy (DMD) comprising
administering to an individual who is suffering from or susceptible to DMD an effective amount of a recombinant follistatin protein comprising an amino acid sequence having at least 95% identity to SEQ ID NO: 1 or 2 fused to an Fc domain via a peptide linker, and wherein the peptide linker comprises a sequence at least 95% identical to SEQ ID NO: 5, 6 or 7.

2. The method of claim 1, wherein the recombinant follistatin protein comprises an amino acid sequence identical to the wild-type human follistatin protein (SEQ ID NO: 1)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCIKAKSCEDIQCTGGKKCLWDFKVGRGRCSLCDELCPDSKS

DEPVCASDNATYASECAMKEAACSSGVLLEVKHSGSCNSISEDTEEEEED

EDQDYSFPISSILEW.

3. The method of claim 1, wherein the recombinant follistatin protein comprises one or more deletions, mutations or insertions as compared to the wild-type human follistatin protein.

4. The method of claim 3, wherein the recombinant follistatin protein comprises a deletion of amino acids residues 212-288 of SEQ ID NO:1.

5. The method of claim 1, wherein the recombinant follistatin protein comprises an amino acid sequence identical to (SEQ ID NO: 2)
GNCWLRQAKNGRCQVLYKTELSKEECCSTGRLSTSWTEEDVNDNTLFKWM

IFNGGAPNCIPCKETCENVDCGPGKKCRMNKKNKPRCVCAPDCSNITWKG

PVCGLDGKTYRNECALLKARCKEQPELEVQYQGRCKKTCRDVFCPGSSTC

VVDQTNNAYCVTCNRICPEPASSEQYLCGNDGVTYSSACHLRKATCLLGR

SIGLAYEGKCISISEDTEEEEEDEDQDYSFPISSILEW.

6. The method of claim 1, wherein the Fc domain comprises an amino acid sequence at least 95% identical to (SEQ ID NO: 3)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK.

7. The method of claim 1, wherein the recombinant follistatin protein is produced from mammalian cells.

8. The method of claim 1, wherein the recombinant follistatin protein is administered systemically.

9. The method of claim 1, wherein the administration of the recombinant follistatin protein results in muscle regeneration, increased muscle strength, increased flexibility, increased range of motion, increased stamina, reduced fatigability, increased blood flow, improved cognition, improved pulmonary function, inflammation inhibition, reduced muscle fibrosis, and/or reduced muscle necrosis.

10. The method of claim 1, wherein the at least one symptom or feature of DMD is selected from the group consisting of muscle wasting, muscle weakness, muscle fragility, muscle necrosis, muscle fibrosis, joint contracture, skeletal deformation, cardiomyopathy, impaired swallowing, impaired bowel and bladder function, muscle ischemia, cognitive impairment, behavioral dysfunction, socialization impairment, scoliosis, and impaired respiratory function.

\* \* \* \* \*

SEQUENCE LISTING

<160> NUMBER OF SEQ ID NOS: 18

<210> SEQ ID NO 1
<211> LENGTH: 315
<212> TYPE: PRT
<213> ORGANISM: Homo sapiens

<400> SEQUENCE: 1

```
Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Asp Glu Asp Gln Asp
    290                 295                 300

Tyr Ser Phe Pro Ile Ser Ser Ile Leu Glu Trp
305                 310                 315
```

<210> SEQ ID NO 2
<211> LENGTH: 238
<212> TYPE: PRT
<213> ORGANISM: Homo sapiens

<400> SEQUENCE: 2

Gly Asn Cys Trp Leu Arg Gln Ala Lys Asn Gly Arg Cys Gln Val Leu

```
              1               5                  10                 15
         Tyr Lys Thr Glu Leu Ser Lys Glu Glu Cys Cys Ser Thr Gly Arg Leu
                         20                 25                 30

Ser Thr Ser Trp Thr Glu Glu Asp Val Asn Asp Asn Thr Leu Phe Lys
                         35                 40                 45

Trp Met Ile Phe Asn Gly Gly Ala Pro Asn Cys Ile Pro Cys Lys Glu
                         50                 55                 60

Thr Cys Glu Asn Val Asp Cys Gly Pro Gly Lys Lys Cys Arg Met Asn
         65                  70                 75                  80

Lys Lys Asn Lys Pro Arg Cys Val Cys Ala Pro Asp Cys Ser Asn Ile
                         85                 90                 95

Thr Trp Lys Gly Pro Val Cys Gly Leu Asp Gly Lys Thr Tyr Arg Asn
                         100                105                110

Glu Cys Ala Leu Leu Lys Ala Arg Cys Lys Glu Gln Pro Glu Leu Glu
                         115                120                125

Val Gln Tyr Gln Gly Arg Cys Lys Lys Thr Cys Arg Asp Val Phe Cys
                         130                135                140

Pro Gly Ser Ser Thr Cys Val Val Asp Gln Thr Asn Asn Ala Tyr Cys
         145                 150                155                 160

Val Thr Cys Asn Arg Ile Cys Pro Glu Pro Ala Ser Ser Glu Gln Tyr
                         165                170                175

Leu Cys Gly Asn Asp Gly Val Thr Tyr Ser Ser Ala Cys His Leu Arg
                         180                185                190

Lys Ala Thr Cys Leu Leu Gly Arg Ser Ile Gly Leu Ala Tyr Glu Gly
                         195                200                205

Lys Cys Ile Ser Ile Ser Glu Asp Thr Glu Glu Glu Glu Asp Glu
                         210                215                220

Asp Gln Asp Tyr Ser Phe Pro Ile Ser Ser Ile Leu Glu Trp
         225                 230                235

<210> SEQ ID NO 3
         <211> LENGTH: 232
         <212> TYPE: PRT
         <213> ORGANISM: Homo sapiens

<400> SEQUENCE: 3

Glu Pro Lys Ser Cys Asp Lys Thr His Thr Cys Pro Pro Cys Pro Ala
         1               5                  10                 15

Pro Glu Leu Leu Gly Gly Pro Ser Val Phe Leu Phe Pro Pro Lys Pro
                         20                 25                 30

Lys Asp Thr Leu Met Ile Ser Arg Thr Pro Glu Val Thr Cys Val Val
                         35                 40                 45

Val Asp Val Ser His Glu Asp Pro Glu Val Lys Phe Asn Trp Tyr Val
                         50                 55                 60

Asp Gly Val Glu Val His Asn Ala Lys Thr Lys Pro Arg Glu Glu Gln
         65                  70                 75                  80

Tyr Asn Ser Thr Tyr Arg Val Val Ser Val Leu Thr Val Leu His Gln
                         85                 90                 95

Asp Trp Leu Asn Gly Lys Glu Tyr Lys Cys Lys Val Ser Asn Lys Ala
                         100                105                110

Leu Pro Ala Pro Ile Glu Lys Thr Ile Ser Lys Ala Lys Gly Gln Pro
                         115                120                125

Arg Glu Pro Gln Val Tyr Thr Leu Pro Pro Ser Arg Asp Glu Leu Thr
                         130                135                140
```

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 4
<211> LENGTH: 226
<212> TYPE: PRT
<213> ORGANISM: Homo sapiens

<400> SEQUENCE: 4

Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Chemically
      synthesized peptide linker
```

```
<400> SEQUENCE: 5

Gly Ala Pro Gly Gly Gly Gly Ala Ala Ala Ala Gly Gly Gly
1               5                   10                  15

Gly Gly Gly Ala Pro
            20

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: Chemically
      synthesized polypeptide linker

<400> SEQUENCE: 6

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro
        35

<210> SEQ ID NO 7
<211> LENGTH: 57
<212> TYPE: PRT
<213> ORGANISM: Artificial Sequence
<220> FEATURE:
<223> OTHER INFORMATION: Description of Artificial Sequence: Chemically
      synthesized polypeptide linker

<400> SEQUENCE: 7

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro Gly Gly Gly Gly Ala Ala Ala
        35                  40                  45

Ala Gly Gly Gly Gly Gly Gly Ala Pro
    50                  55

<210> SEQ ID NO 8
<211> LENGTH: 598
<212> TYPE: PRT
<213> ORGANISM: Homo sapiens

<400> SEQUENCE: 8

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
```

-continued

```
                100                 105                 110
Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
        130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Asp Glu Asp Gln Asp
    290                 295                 300

Tyr Ser Phe Pro Ile Ser Ser Ile Leu Glu Trp Gly Ala Pro Gly Gly
305                 310                 315                 320

Gly Gly Gly Ala Ala Ala Ala Gly Gly Gly Gly Gly Ala Pro
                325                 330                 335

Gly Gly Gly Gly Gly Ala Ala Ala Ala Gly Gly Gly Gly Gly
            340                 345                 350

Ala Pro Gly Gly Gly Gly Ala Ala Ala Ala Gly Gly Gly Gly
        355                 360                 365

Gly Gly Ala Pro Lys Thr His Thr Cys Pro Pro Cys Pro Ala Pro Glu
    370                 375                 380

Leu Leu Gly Gly Pro Ser Val Phe Leu Phe Pro Pro Lys Pro Lys Asp
385                 390                 395                 400

Thr Leu Met Ile Ser Arg Thr Pro Glu Val Thr Cys Val Val Val Asp
                405                 410                 415

Val Ser His Glu Asp Pro Glu Val Lys Phe Asn Trp Tyr Val Asp Gly
            420                 425                 430

Val Glu Val His Asn Ala Lys Thr Lys Pro Arg Glu Glu Gln Tyr Asn
        435                 440                 445

Ser Thr Tyr Arg Val Val Ser Val Leu Thr Val Leu His Gln Asp Trp
    450                 455                 460

Leu Asn Gly Lys Glu Tyr Lys Cys Lys Val Ser Asn Lys Ala Leu Pro
465                 470                 475                 480

Ala Pro Ile Glu Lys Thr Ile Ser Lys Ala Lys Gly Gln Pro Arg Glu
                485                 490                 495

Pro Gln Val Tyr Thr Leu Pro Pro Ser Arg Asp Glu Leu Thr Lys Asn
            500                 505                 510

Gln Val Ser Leu Thr Cys Leu Val Lys Gly Phe Tyr Pro Ser Asp Ile
        515                 520                 525
```

```
Ala Val Glu Trp Glu Ser Asn Gly Gln Pro Glu Asn Tyr Lys Thr
    530                 535                 540
Thr Pro Pro Val Leu Asp Ser Asp Gly Ser Phe Phe Leu Tyr Ser Lys
545                 550                 555                 560
Leu Thr Val Asp Lys Ser Arg Trp Gln Gln Gly Asn Val Phe Ser Cys
                565                 570                 575
Ser Val Met His Glu Ala Leu His Asn His Tyr Thr Gln Lys Ser Leu
            580                 585                 590
Ser Leu Ser Pro Gly Lys
            595

<210> SEQ ID NO 9
<211> LENGTH: 604
<212> TYPE: PRT
<213> ORGANISM: Homo sapiens

<400> SEQUENCE: 9

Gly Asn Cys Trp Leu Arg Gln Ala Lys Asn Gly Arg Cys Gln Val Leu
1               5                   10                  15
Tyr Lys Thr Glu Leu Ser Lys Glu Glu Cys Cys Ser Thr Gly Arg Leu
            20                  25                  30
Ser Thr Ser Trp Thr Glu Glu Asp Val Asn Asp Asn Thr Leu Phe Lys
        35                  40                  45
Trp Met Ile Phe Asn Gly Gly Ala Pro Asn Cys Ile Pro Cys Lys Glu
    50                  55                  60
Thr Cys Glu Asn Val Asp Cys Gly Pro Gly Lys Lys Cys Arg Met Asn
65                  70                  75                  80
Lys Lys Asn Lys Pro Arg Cys Val Cys Ala Pro Asp Cys Ser Asn Ile
                85                  90                  95
Thr Trp Lys Gly Pro Val Cys Gly Leu Asp Gly Lys Thr Tyr Arg Asn
            100                 105                 110
Glu Cys Ala Leu Leu Lys Ala Arg Cys Lys Glu Gln Pro Glu Leu Glu
        115                 120                 125
Val Gln Tyr Gln Gly Arg Cys Lys Lys Thr Cys Arg Asp Val Phe Cys
    130                 135                 140
Pro Gly Ser Ser Thr Cys Val Val Asp Gln Thr Asn Asn Ala Tyr Cys
145                 150                 155                 160
Val Thr Cys Asn Arg Ile Cys Pro Glu Pro Ala Ser Ser Glu Gln Tyr
                165                 170                 175
Leu Cys Gly Asn Asp Gly Val Thr Tyr Ser Ser Ala Cys His Leu Arg
            180                 185                 190
Lys Ala Thr Cys Leu Leu Gly Arg Ser Ile Gly Leu Ala Tyr Glu Gly
        195                 200                 205
Lys Cys Ile Lys Ala Lys Ser Cys Glu Asp Ile Gln Cys Thr Gly Gly
    210                 215                 220
Lys Lys Cys Leu Trp Asp Phe Lys Val Gly Arg Gly Arg Cys Ser Leu
225                 230                 235                 240
Cys Asp Glu Leu Cys Pro Asp Ser Lys Ser Asp Glu Pro Val Cys Ala
                245                 250                 255
Ser Asp Asn Ala Thr Tyr Ala Ser Glu Cys Ala Met Lys Glu Ala Ala
            260                 265                 270
Cys Ser Ser Gly Val Leu Leu Glu Val Lys His Ser Gly Ser Cys Asn
        275                 280                 285
Ser Ile Ser Glu Asp Thr Glu Glu Glu Glu Glu Asp Glu Asp Gln Asp
```

```
            290                 295                 300
Tyr Ser Phe Pro Ile Ser Ser Ile Leu Glu Trp Gly Ala Pro Gly Gly
305                 310                 315                 320

Gly Gly Gly Ala Ala Ala Ala Gly Gly Gly Gly Gly Gly Gly Ala Pro
                325                 330                 335

Gly Gly Gly Gly Gly Ala Ala Ala Ala Gly Gly Gly Gly Gly Gly Gly
            340                 345                 350

Ala Pro Gly Gly Gly Gly Ala Ala Ala Ala Gly Gly Gly Gly Gly Gly
        355                 360                 365

Gly Gly Ala Pro Glu Pro Lys Ser Cys Asp Lys Thr His Thr Cys Pro
370                 375                 380

Pro Cys Pro Ala Pro Glu Leu Leu Gly Gly Pro Ser Val Phe Leu Phe
385                 390                 395                 400

Pro Pro Lys Pro Lys Asp Thr Leu Met Ile Ser Arg Thr Pro Glu Val
                405                 410                 415

Thr Cys Val Val Val Asp Val Ser His Glu Asp Pro Glu Val Lys Phe
            420                 425                 430

Asn Trp Tyr Val Asp Gly Val Glu Val His Asn Ala Lys Thr Lys Pro
        435                 440                 445

Arg Glu Glu Gln Tyr Asn Ser Thr Tyr Arg Val Val Ser Val Leu Thr
450                 455                 460

Val Leu His Gln Asp Trp Leu Asn Gly Lys Glu Tyr Lys Cys Lys Val
465                 470                 475                 480

Ser Asn Lys Ala Leu Pro Ala Pro Ile Glu Lys Thr Ile Ser Lys Ala
                485                 490                 495

Lys Gly Gln Pro Arg Glu Pro Gln Val Tyr Thr Leu Pro Pro Ser Arg
            500                 505                 510

Asp Glu Leu Thr Lys Asn Gln Val Ser Leu Thr Cys Leu Val Lys Gly
        515                 520                 525

Phe Tyr Pro Ser Asp Ile Ala Val Glu Trp Glu Ser Asn Gly Gln Pro
530                 535                 540

Glu Asn Asn Tyr Lys Thr Thr Pro Pro Val Leu Asp Ser Asp Gly Ser
545                 550                 555                 560

Phe Phe Leu Tyr Ser Lys Leu Thr Val Asp Lys Ser Arg Trp Gln Gln
                565                 570                 575

Gly Asn Val Phe Ser Cys Ser Val Met His Glu Ala Leu His Asn His
            580                 585                 590

Tyr Thr Gln Lys Ser Leu Ser Leu Ser Pro Gly Lys
        595                 600

<210> SEQ ID NO 10
<211> LENGTH: 521
<212> TYPE: PRT
<213> ORGANISM: Homo sapiens

<400> SEQUENCE: 10

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
                20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
        50                  55                  60
```

-continued

```
Thr Cys Glu Asn Val Asp Cys Gly Pro Gly Lys Cys Arg Met Asn
 65                  70                  75                  80

Lys Lys Asn Lys Pro Arg Cys Val Cys Ala Pro Asp Cys Ser Asn Ile
                 85                  90                  95

Thr Trp Lys Gly Pro Val Cys Gly Leu Asp Gly Lys Thr Tyr Arg Asn
                100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
                180                 185                 190

Lys Ala Thr Cys Leu Leu Gly Arg Ser Ile Gly Leu Ala Tyr Glu Gly
            195                 200                 205

Lys Cys Ile Ser Ile Ser Glu Asp Thr Glu Glu Glu Glu Asp Glu
210                 215                 220

Asp Gln Asp Tyr Ser Phe Pro Ile Ser Ser Ile Leu Glu Trp Gly Ala
225                 230                 235                 240

Pro Gly Gly Gly Gly Ala Ala Ala Ala Gly Gly Gly Gly Gly
                245                 250                 255

Gly Ala Pro Gly Gly Gly Gly Ala Ala Ala Ala Gly Gly Gly
            260                 265                 270

Gly Gly Gly Ala Pro Gly Gly Gly Gly Ala Ala Ala Ala Gly
        275                 280                 285

Gly Gly Gly Gly Ala Pro Lys Thr His Thr Cys Pro Pro Cys Pro
290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
                340                 345                 350

Val Asp Gly Val Glu Val His Asn Ala Lys Thr Lys Pro Arg Glu Glu
            355                 360                 365

Gln Tyr Asn Ser Thr Tyr Arg Val Val Ser Val Leu Thr Val Leu His
370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Asp Glu Leu
                420                 425                 430

Thr Lys Asn Gln Val Ser Leu Thr Cys Leu Val Lys Gly Phe Tyr Pro
            435                 440                 445

Ser Asp Ile Ala Val Glu Trp Glu Ser Asn Gly Gln Pro Glu Asn Asn
        450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
```

```
                    485                 490                 495
Phe Ser Cys Ser Val Met His Glu Ala Leu His Asn His Tyr Thr Gln
                500                 505                 510
Lys Ser Leu Ser Leu Ser Pro Gly Lys
            515                 520

<210> SEQ ID NO 11
<211> LENGTH: 527
<212> TYPE: PRT
<213> ORGANISM: Homo sapiens

<400> SEQUENCE: 11

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
                20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                    85                  90                  95

Thr Trp Lys Gly Pro Val Cys Gly Leu Asp Gly Lys Thr Tyr Arg Asn
                100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                    165                 170                 175

Leu Cys Gly Asn Asp Gly Val Thr Tyr Ser Ser Ala Cys His Leu Arg
                180                 185                 190

Lys Ala Thr Cys Leu Leu Gly Arg Ser Ile Gly Leu Ala Tyr Glu Gly
            195                 200                 205

Lys Cys Ile Ser Ile Ser Glu Asp Thr Glu Glu Glu Glu Asp Glu
    210                 215                 220

Asp Gln Asp Tyr Ser Phe Pro Ile Ser Ser Ile Leu Glu Trp Gly Ala
225                 230                 235                 240

Pro Gly Gly Gly Gly Ala Ala Ala Ala Gly Gly Gly Gly
                    245                 250                 255

Gly Ala Pro Gly Gly Gly Gly Ala Ala Ala Ala Gly Gly Gly
                260                 265                 270

Gly Gly Gly Ala Pro Gly Gly Gly Gly Ala Ala Ala Ala Gly
            275                 280                 285

Gly Gly Gly Gly Ala Pro Glu Pro Lys Ser Cys Asp Lys Thr His
    290                 295                 300

Thr Cys Pro Pro Cys Pro Ala Pro Glu Leu Leu Gly Gly Pro Ser Val
305                 310                 315                 320

Phe Leu Phe Pro Pro Lys Pro Lys Asp Thr Leu Met Ile Ser Arg Thr
                    325                 330                 335
```

```
Pro Glu Val Thr Cys Val Val Asp Val Ser His Glu Asp Pro Glu
            340                 345                 350

Val Lys Phe Asn Trp Tyr Val Asp Gly Val Glu Val His Asn Ala Lys
355                 360                 365

Thr Lys Pro Arg Glu Glu Gln Tyr Asn Ser Thr Tyr Arg Val Val Ser
    370                 375                 380

Val Leu Thr Val Leu His Gln Asp Trp Leu Asn Gly Lys Glu Tyr Lys
385                 390                 395                 400

Cys Lys Val Ser Asn Lys Ala Leu Pro Ala Pro Ile Glu Lys Thr Ile
                405                 410                 415

Ser Lys Ala Lys Gly Gln Pro Arg Glu Pro Gln Val Tyr Thr Leu Pro
            420                 425                 430

Pro Ser Arg Asp Glu Leu Thr Lys Asn Gln Val Ser Leu Thr Cys Leu
        435                 440                 445

Val Lys Gly Phe Tyr Pro Ser Asp Ile Ala Val Glu Trp Glu Ser Asn
    450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
                485                 490                 495

Trp Gln Gln Gly Asn Val Phe Ser Cys Ser Val Met His Glu Ala Leu
            500                 505                 510

His Asn His Tyr Thr Gln Lys Ser Leu Ser Leu Ser Pro Gly Lys
        515                 520                 525

<210> SEQ ID NO 12
<211> LENGTH: 288
<212> TYPE: PRT
<213> ORGANISM: Homo sapiens

<400> SEQUENCE: 12

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190
```

```
Lys Ala Thr Cys Leu Leu Gly Arg Ser Ile Gly Leu Ala Tyr Glu Gly
            195                 200                 205

Lys Cys Ile Lys Ala Lys Ser Cys Glu Asp Ile Gln Cys Thr Gly Gly
            210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
                260                 265                 270

Cys Ser Ser Gly Val Leu Leu Glu Val Lys His Ser Gly Ser Cys Asn
                275                 280                 285

<210> SEQ ID NO 13
<211> LENGTH: 594
<212> TYPE: PRT
<213> ORGANISM: Homo sapiens

<400> SEQUENCE: 13

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
        130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
            195                 200                 205

Lys Cys Ile Lys Ala Lys Ser Cys Glu Asp Ile Gln Cys Thr Gly Gly
            210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
                260                 265                 270

Cys Ser Ser Gly Val Leu Leu Glu Val Lys His Ser Gly Ser Cys Asn
```

```
                275                 280                 285
Ser Ile Ser Glu Asp Thr Glu Glu Glu Asp Glu Asp Gln Asp
    290                 295                 300

Tyr Ser Phe Pro Ile Ser Ser Ile Leu Glu Trp Gly Ala Pro Gly Gly
305                 310                 315                 320

Gly Gly Gly Ala Ala Ala Ala Gly Gly Gly Gly Gly Ala Pro
            325                 330                 335

Gly Gly Gly Gly Gly Ala Ala Ala Ala Gly Gly Gly Gly
        340                 345                 350

Ala Pro Gly Gly Gly Gly Ala Ala Ala Ala Gly Gly Gly Gly
            355                 360                 365

Gly Gly Ala Pro Gly Cys Lys Pro Cys Ile Cys Thr Val Pro Glu Val
        370                 375                 380

Ser Ser Val Phe Ile Phe Pro Pro Lys Pro Lys Asp Val Leu Thr Ile
385                 390                 395                 400

Thr Leu Thr Pro Lys Val Thr Cys Val Val Val Asp Ile Ser Lys Asp
                405                 410                 415

Asp Pro Glu Val Gln Phe Ser Trp Phe Val Asp Val Glu Val His
            420                 425                 430

Thr Ala Gln Thr Gln Pro Arg Glu Glu Gln Phe Asn Ser Thr Phe Arg
            435                 440                 445

Ser Val Ser Glu Leu Pro Ile Met His Gln Asp Trp Leu Asn Gly Lys
    450                 455                 460

Glu Phe Lys Cys Arg Val Asn Ser Ala Ala Phe Pro Ala Pro Ile Glu
465                 470                 475                 480

Lys Thr Ile Ser Lys Thr Lys Gly Arg Pro Lys Ala Pro Gln Val Tyr
                485                 490                 495

Thr Ile Pro Pro Pro Lys Glu Gln Met Ala Lys Asp Lys Val Ser Leu
            500                 505                 510

Thr Cys Met Ile Thr Asp Phe Phe Pro Glu Asp Ile Thr Val Glu Trp
            515                 520                 525

Gln Trp Asn Gly Gln Pro Ala Glu Asn Tyr Lys Asn Thr Gln Pro Ile
    530                 535                 540

Met Asp Thr Asp Gly Ser Tyr Phe Val Tyr Ser Lys Leu Asn Val Gln
545                 550                 555                 560

Lys Ser Asn Trp Glu Ala Gly Asn Thr Phe Thr Cys Ser Val Leu His
                565                 570                 575

Glu Gly Leu His Asn His His Thr Glu Lys Ser Leu Ser His Ser Pro
            580                 585                 590

Gly Lys

<210> SEQ ID NO 14
<211> LENGTH: 227
<212> TYPE: PRT
<213> ORGANISM: Homo sapiens

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
```

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 227
<212> TYPE: PRT
<213> ORGANISM: Homo sapiens

<400> SEQUENCE: 15

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

-continued

```
Asp Lys Ser Arg Trp Gln Gln Gly Asn Val Phe Ser Cys Ser Val Met
        195                 200                 205
His Glu Ala Leu Lys Phe His Tyr Thr Gln Lys Ser Leu Ser Leu Ser
    210                 215                 220
Pro Gly Lys
225
```

<210> SEQ ID NO 16
<211> LENGTH: 599
<212> TYPE: PRT
<213> ORGANISM: Homo sapiens

<400> SEQUENCE: 16

```
Gly Asn Cys Trp Leu Arg Gln Ala Lys Asn Gly Arg Cys Gln Val Leu
1               5                   10                  15
Tyr Lys Thr Glu Leu Ser Lys Glu Glu Cys Cys Ser Thr Gly Arg Leu
            20                  25                  30
Ser Thr Ser Trp Thr Glu Glu Asp Val Asn Asp Asn Thr Leu Phe Lys
        35                  40                  45
Trp Met Ile Phe Asn Gly Gly Ala Pro Asn Cys Ile Pro Cys Lys Glu
    50                  55                  60
Thr Cys Glu Asn Val Asp Cys Gly Pro Gly Lys Lys Cys Arg Met Asn
65                  70                  75                  80
Lys Lys Asn Lys Pro Arg Cys Val Cys Ala Pro Asp Cys Ser Asn Ile
                85                  90                  95
Thr Trp Lys Gly Pro Val Cys Gly Leu Asp Gly Lys Thr Tyr Arg Asn
            100                 105                 110
Glu Cys Ala Leu Leu Lys Ala Arg Cys Lys Glu Gln Pro Glu Leu Glu
        115                 120                 125
Val Gln Tyr Gln Gly Arg Cys Lys Lys Thr Cys Arg Asp Val Phe Cys
    130                 135                 140
Pro Gly Ser Ser Thr Cys Val Val Asp Gln Thr Asn Asn Ala Tyr Cys
145                 150                 155                 160
Val Thr Cys Asn Arg Ile Cys Pro Glu Pro Ala Ser Ser Glu Gln Tyr
                165                 170                 175
Leu Cys Gly Asn Asp Gly Val Thr Tyr Ser Ser Ala Cys His Leu Arg
            180                 185                 190
Lys Ala Thr Cys Leu Leu Gly Arg Ser Ile Gly Leu Ala Tyr Glu Gly
        195                 200                 205
Lys Cys Ile Lys Ala Lys Ser Cys Glu Asp Ile Gln Cys Thr Gly Gly
    210                 215                 220
Lys Lys Cys Leu Trp Asp Phe Lys Val Gly Arg Gly Arg Cys Ser Leu
225                 230                 235                 240
Cys Asp Glu Leu Cys Pro Asp Ser Lys Ser Asp Glu Pro Val Cys Ala
                245                 250                 255
Ser Asp Asn Ala Thr Tyr Ala Ser Glu Cys Ala Met Lys Glu Ala Ala
            260                 265                 270
Cys Ser Ser Gly Val Leu Leu Glu Val Lys His Ser Gly Ser Cys Asn
        275                 280                 285
Ser Ile Ser Glu Asp Thr Glu Glu Glu Glu Asp Glu Asp Gln Asp
    290                 295                 300
Tyr Ser Phe Pro Ile Ser Ser Ile Leu Glu Trp Gly Ala Pro Gly Gly
305                 310                 315                 320
Gly Gly Gly Ala Ala Ala Ala Gly Gly Gly Gly Gly Ala Pro
                325                 330                 335
```

Gly Gly Gly Gly Gly Ala Ala Ala Ala Gly Gly Gly Gly
            340                 345             350

Ala Pro Gly Gly Gly Gly Ala Ala Ala Gly Gly Gly Gly
        355                 360             365

Gly Gly Ala Pro Asp Lys Thr His Thr Cys Pro Pro Cys Pro Ala Pro
370                 375                 380

Glu Leu Leu Gly Gly Pro Ser Val Phe Leu Phe Pro Pro Lys Pro Lys
385                 390                 395                 400

Asp Thr Leu Met Ile Ser Arg Thr Pro Glu Val Thr Cys Val Val Val
                405                 410                 415

Asp Val Ser His Glu Asp Pro Glu Val Lys Phe Asn Trp Tyr Val Asp
            420                 425                 430

Gly Val Glu Val His Asn Ala Lys Thr Lys Pro Arg Glu Glu Gln Tyr
        435                 440                 445

Asn Ser Thr Tyr Arg Val Val Ser Val Leu Thr Val Leu His Gln Asp
    450                 455                 460

Trp Leu Asn Gly Lys Glu Tyr Lys Cys Lys Val Ser Asn Lys Ala Leu
465                 470                 475                 480

Pro Ala Pro Ile Glu Lys Thr Ile Ser Lys Ala Lys Gly Gln Pro Arg
                485                 490                 495

Glu Pro Gln Val Tyr Thr Leu Pro Pro Ser Arg Asp Glu Leu Thr Lys
            500                 505                 510

Asn Gln Val Ser Leu Thr Cys Leu Val Lys Gly Phe Tyr Pro Ser Asp
        515                 520                 525

Ile Ala Val Glu Trp Glu Ser Asn Gly Gln Pro Glu Asn Asn Tyr Lys
    530                 535                 540

Thr Thr Pro Pro Val Leu Asp Ser Asp Gly Ser Phe Phe Leu Tyr Ser
545                 550                 555                 560

Lys Leu Thr Val Asp Lys Ser Arg Trp Gln Gln Gly Asn Val Phe Ser
                565                 570                 575

Cys Ser Val Met His Glu Ala Leu His Asn His Tyr Thr Gln Lys Ser
            580                 585                 590

Leu Ser Leu Ser Pro Gly Lys
        595

<210> SEQ ID NO 17
<211> LENGTH: 599
<212> TYPE: PRT
<213> ORGANISM: Homo sapiens

<400> SEQUENCE: 17

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn

-continued

```
                100                 105                 110
Glu Cys Ala Leu Leu Lys Ala Arg Cys Lys Glu Gln Pro Glu Leu Glu
            115                 120                 125

Val Gln Tyr Gln Gly Arg Cys Lys Lys Thr Cys Arg Asp Val Phe Cys
130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
            195                 200                 205

Lys Cys Ile Lys Ala Lys Ser Cys Glu Asp Ile Gln Cys Thr Gly Gly
            210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
            275                 280                 285

Ser Ile Ser Glu Asp Thr Glu Glu Glu Glu Asp Glu Asp Gln Asp
            290                 295                 300

Tyr Ser Phe Pro Ile Ser Ser Ile Leu Glu Trp Gly Ala Pro Gly Gly
305                 310                 315                 320

Gly Gly Gly Ala Ala Ala Ala Gly Gly Gly Gly Ala Pro
                325                 330                 335

Gly Gly Gly Gly Gly Ala Ala Ala Ala Gly Gly Gly Gly Gly
            340                 345                 350

Ala Pro Gly Gly Gly Gly Ala Ala Ala Ala Gly Gly Gly Gly
            355                 360                 365

Gly Gly Ala Pro Asp Lys Thr His Thr Cys Pro Pro Cys Pro Ala Pro
            370                 375                 380

Glu Leu Leu Gly Gly Pro Ser Val Phe Leu Phe Pro Pro Lys Pro Lys
385                 390                 395                 400

Asp Thr Leu Met Ile Ser Arg Thr Pro Glu Val Thr Cys Val Val Val
                405                 410                 415

Asp Val Ser His Glu Asp Pro Glu Val Lys Phe Asn Trp Tyr Val Asp
            420                 425                 430

Gly Val Glu Val His Asn Ala Lys Thr Lys Pro Arg Glu Glu Gln Tyr
            435                 440                 445

Asn Ser Thr Tyr Arg Val Val Ser Val Leu Thr Val Leu His Gln Asp
            450                 455                 460

Trp Leu Asn Gly Lys Glu Tyr Lys Cys Lys Val Ser Asn Lys Ala Leu
465                 470                 475                 480

Pro Ala Pro Ile Glu Lys Thr Ile Ser Lys Ala Lys Gly Gln Pro Arg
                485                 490                 495

Glu Pro Gln Val Tyr Thr Leu Pro Pro Ser Arg Glu Glu Met Thr Lys
            500                 505                 510

Asn Gln Val Ser Leu Thr Cys Leu Val Lys Gly Phe Tyr Pro Ser Asp
            515                 520                 525
```

```
Ile Ala Val Glu Trp Glu Ser Asn Gly Gln Pro Glu Asn Asn Tyr Lys
        530                 535                 540

Thr Thr Pro Pro Val Leu Asp Ser Asp Gly Ser Phe Phe Leu Tyr Ser
545                 550                 555                 560

Lys Leu Thr Val Asp Lys Ser Arg Trp Gln Gln Gly Asn Val Phe Ser
                565                 570                 575

Cys Ser Val Met His Glu Ala Leu Lys Phe His Tyr Thr Gln Lys Ser
                580                 585                 590

Leu Ser Leu Ser Pro Gly Lys
        595

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Leu Glu Val Leu Phe Gln Gly Pro
1               5
```